(12) United States Patent
Chuntharapai et al.

(10) Patent No.: US 6,713,609 B1
(45) Date of Patent: *Mar. 30, 2004

(54) MONOCLONAL ANTIBODIES TO TYPE I INTERFERON RECEPTOR

(75) Inventors: Anan Chuntharapai, Colma, CA (US); Kyung Jin Kim, Los Altos, CA (US); Richard B. Love, San Francisco, CA (US); Ji Lu, Fremont, CA (US)

(73) Assignee: Genentech, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/056,461

(22) Filed: Apr. 7, 1998

Related U.S. Application Data

(63) Continuation-in-part of application No. 08/888,140, filed on Jul. 3, 1997, now abandoned.
(60) Provisional application No. 60/058,212, filed on Jul. 16, 1996.

(51) Int. Cl.[7] ............................ C07K 16/28; C12P 21/08

(52) U.S. Cl. ............................ 530/388.22; 530/388.1; 424/143.1; 435/70.21

(58) Field of Search .................. 530/388.1, 388.22; 424/143.1; 435/70.21

(56) References Cited

U.S. PATENT DOCUMENTS

| 5,460,811 A | 10/1995 | Goeddel et al. |
| 5,516,515 A | 5/1996 | Vellucci et al. |

FOREIGN PATENT DOCUMENTS

| EP | 0 563 487 | 10/1993 |
| WO | 93/20187 | 10/1993 |
| WO | 95/07716 | 3/1995 |
| WO | 97/41229 | 11/1997 |

OTHER PUBLICATIONS

Abramovich et al., "Differential Tyrosine Phosphorylation of the IFNAR Chain of the Type I Interferon Receptor and of an Associated Surface Protein in Response to IFN–α and IFB β," EMBO Journal, 13(24):5871–5877 (1994).
Abramovich et al., "Human IFN–α Receptor Detected by Two Monoclonal Antibodies," J. Interferon Research, 12(supp. 1):S217 (Sep. 9–Oct. 2, 1992 Annual Mtg., international Society for Interferon Res.) (1992).
Capon, et al., "Two Distinct Families of Human and Bovine Interferon –α Genes are Coordinately Expressed and Encode Functional Polypeptides," Molecular & Cellular Biology, 5:768–779 (1985).
Chuntharapai, et al., "Structure–Function Studies of Human Interferon –α Receptor II Using Mabs," FASEB Journal, (Abst. #1877), 10(6):A1325, (Apr. 30, 1996).
Colamonici, et al., "Study of the Structure of the IFN–α2 Receptor by Anti–IFNα2 Receptor Antibodies and Affinity Cross–Linking," j. Interferon Res., (Abst. 118–6, Annual Int. Society fo Interferon Res. Mtg., Nov. 14–18, 1990). 10(Suppl. 1):S158.
Colamonici, et al., "Identification of a Novel Subunit of the Type I Interferon Receptor Localized to Human Chromosome 21," Journal of Biological Chemistry, 268(15):10895–10899 (1993).
Colamonici , et al., "Characterization of three Monoclonal Antibodies that Recognized the Interferon α2 Receptor," Proc. Natl. Acad. Sci., 87:7230–7234 (1990).
Colamonici et al., "Multichain Structure of the IFN –α Receptor on Hematopietic Cells," J. Immunol., 148(7):2126–2132 (1992).
Goeddel et al., "The Structure of Eight Distinct Cloned Human Leukocyte Interferon cDNAs," Nature, 290:20–26 (1981).
Hauptmann et al., "A Novel Class of Human Type I Interferons," Nucleic Acids Research, 13(13):4739–4749 (1985).
Ling et al., "Human Type I Interferon Receptor, IFNAR, is a Heavily Glycosylated 120–130 kD Membrane Protein," J. Interferon & Cytokine Res., 15:56–61 (1995).
Lu et al., "Structure–Function Studies of IFN–αR Using Mabs Binding to Different Epitopes," 9th International Congress of Immunology, (Jul. 23–29, 1995) Abst. 713:121 (1996).
Novick et al., "Antibodies to IFN–α Receptor," J. Interferon Research, (Nov. 3–8, 1991 Annual Mtg., International Society for Interferon Research) 11 (Supp. 1): s203 (1991).
Novick et al., Monoclonal Antibodies to the Human IFN–α Receptor: Blocking of the Biological Activities of IFN–α and Purification of the Receptor,: J. Interferon Res., (Abst. P3–6, Nov. 14–18, 1988 Annual Mtg., International Society for Interferon Res.) 8(Supp. 1):s93 (1988).
Roselen et al., "Detection of Functional Interferon Alpha Receptors in Human Neuroendocrine Tumor Cell Lines Using a New Monoclonal Antibody," Eur. Cytokine Netw., 3(2):81–88 (1992).
Russell–Harde et al., "Baculovirus Expression of the Human Interferon α/β Receptor and Characterization Using Monoclonal Antibodies," J. Interferon Res., (Poster Presentation 2: Receptors, Abst. PW2–1, Annual Mtg. of ISICR on the Inte.) 13(Supp. 1) :s78 (1993).

(List continued on next page.)

*Primary Examiner*—Yvonne Eyler
*Assistant Examiner*—Micheal T Brannock
(74) *Attorney, Agent, or Firm*—Merchant & Gould P.C.

(57) ABSTRACT

Anti-IFNAR1 monoclonal antibodies with neutralizing activities against the anti-viral cytopathic effects of various type I interferons are provided.

18 Claims, 11 Drawing Sheets

(1 of 11 Drawing Sheet(s) Filed in Color)

OTHER PUBLICATIONS

Russell–Harde et al., "Reconstitution of a High Affinity Binding Site for Type Interferons," Journal of Biol. Chemistry, 270(44):26033–26036 (1995).

Sagawa et al., "Identification of the Monoclonal Antibody Receptor(s) for Interferon–alpha, –beta, or –gamma," Tissue Antigens, (4th International Conference on Human Leukocyte Differ. Antigens) 33(2):331 (1989).

Scott et al., "Production of Antibody to Human Interferon–Alpha Receptor Proteins," Hybridoma (abstract only) 5(1):81 (1986).

Taniguchi et al., "Construction and Identification of a Bacterial Plasmid Containing the Human Fibroblast Interferon Gene Sequence," Proc. Japan Acad., 55(Ser. B):464–469 (1979).

Taniguchi et al., "The Nucleotide Sequence of Human Fibroblast Interferon cDNA,"Gene, 10:11–15 (1980).

Uze et al., "Murine Tumor Cells Expressing the Gene for the Human Interferon $\alpha\beta$ Receptor Elicit Antibodies in Syngeneic Mice to the Active Form of the Receptor," European Journal of Immunology, 21:447–451 (1991).

Chuntharapai et al., "Structure–function studies of human interferon–$\alpha$ Receptor II Using Mabs" poster, presented at the 1996 Joint Meeting of the International Cytokine Society and hte International Society for Interferon and Cytokine Research (Oct. 6–10, 1996).

Lu et al., "Structure–Function Study of the Extracellular Domain of the Human IFN–$\alpha$ Receptor (nIFNAR1) Using Blocking Monoclonal Antibodies: The Role of Domains 1 and 2,", The Journal of Immunology, 160:1782–1788 (1998).

Cohen, "Ligand–Induced Association of the Type I Interferon Receptor Components," Mol. Cell. Biol. 15:4208 (1995).

Cohen, et al., "Cloning, Expression and Biological Activity of a New Variant of Human Interferon $\alpha$ Identified in Virus Induced Lymphoblastoid Cells," Dev. Biol. Standard, 60:111–122 (1995).

Croze et al., "The Human 'Type Interferon Receptor'", Journal of Biol. Chemistry, 271:33165–33168 (1996).

Domanski et al., "The Type–I Interferon Receptor. The Long and Short of it," Cytokine and Growth Factor Rev., 7:143–151 (1996).

Navarro et al., "Immunohistochemical Detection of the Type I Interferon Receptor in Human Fetal, Adult, and Neoplastic Tissues," Modern Pathol., 9:150–156 (1996).

Platanias et al., "Differences in Interferon $\alpha$ and $\beta$ Signaling," Journal of Biological Chemistry, 271:23630–23633 (1996).

Schellekens et al., "Factors inhibiting IFN activity," Biother., 8:199–204 (1996).

Tovey et al., "Role of the Type I Interferon in Allograft Rejection," J. Leukocyte Biol., 59:512–517 (1996).

Chuntharapai et al., "Determination of Residues Involved in Ligand Binding and Signal Transmission in the Human IFN–$\alpha$ Receptor 2," The Journal of Immunology, 163:766–773 (1999).

Benoit et al., "A monoclonal antibody to recombinant human IFN–$\alpha$ receptor inhibits biologic activity of several species of human IFN–$\alpha$, IFN–$\beta$, and IFN–omega" J. Immunol. 150(3):707–716 (1993).

Cleary et al., "Knockout and reconstitution of a functional human type I interferon receptor complex" Journal of Biological Chemistry 269(29):18747–18749 (1994).

Constantinescu et al., "Role of interferon $\alpha\beta$ receptor chain 1 in the structure and transmembrane signaling of the interferon $\alpha\beta$ receptor complex" Proc. Natl. Acad. Sci. 91:9602–9606 (1994).

Domanski et al., "Cloning and expression of a long form of the $\beta$ subunit of the interferon $\alpha\beta$ receptor that is required for signaling" Journal of Biological Chemistry 270(37):21606–21611 (1995).

Eid and Tovey J. Interferon Cytokine Res. 15:205–211 (1995).

Liebert, "Nomenclature of the Human Interferon Genes" J. Interferon Res., 13:443–444 (1993).

Muller et al., "Functional role of the type I and type II interferons in antiviral defense" Science 264:1918–1921 (1994).

Novick et al., "The human interferon $\alpha\beta$ receptor: characterization and molecular cloning" Cell 77:391–400 (1994).

Uze et al., "Genetic transfer of a functional human interferon $\alpha$ receptor into mouse cells: cloning and expression of its cDNA" Cell 60:225–234 (1990).

Weissmann and Weber Prog. Nucl. Acid. Res. Mol. Biol. 33:251 (1986).

"Nomenclature of the human interferon genes" J. Interferon Research, Mary Ann Liebert, Inc. vol. 13:443–444 (1993).

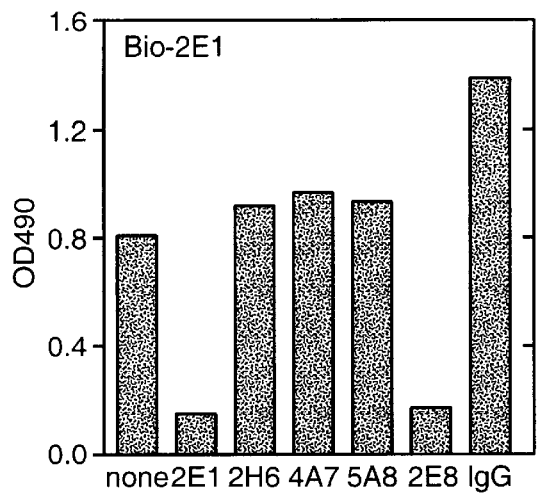
FIG._2A
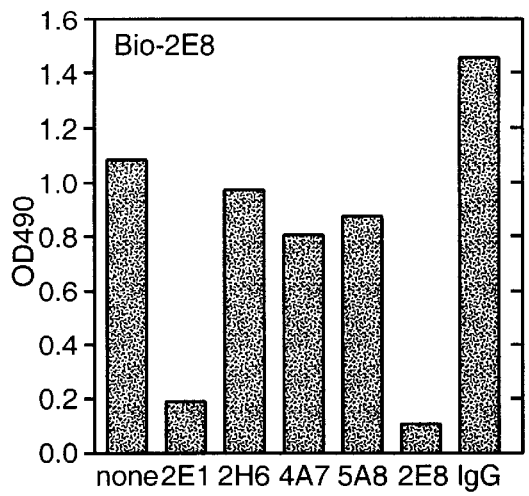
FIG._2B
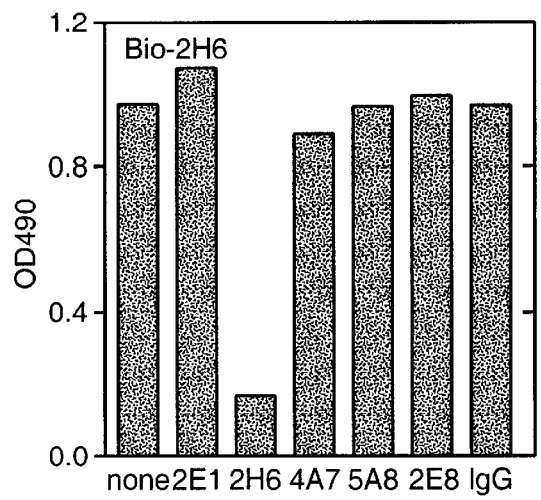
FIG._2C
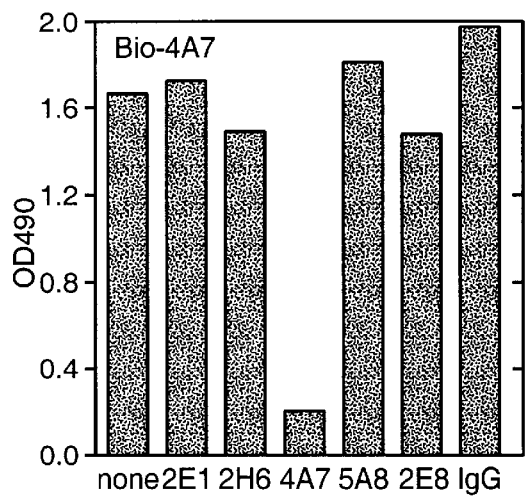
FIG._2D
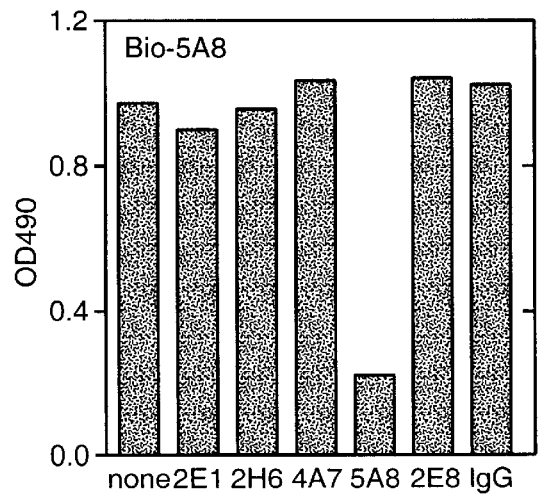
FIG._2E

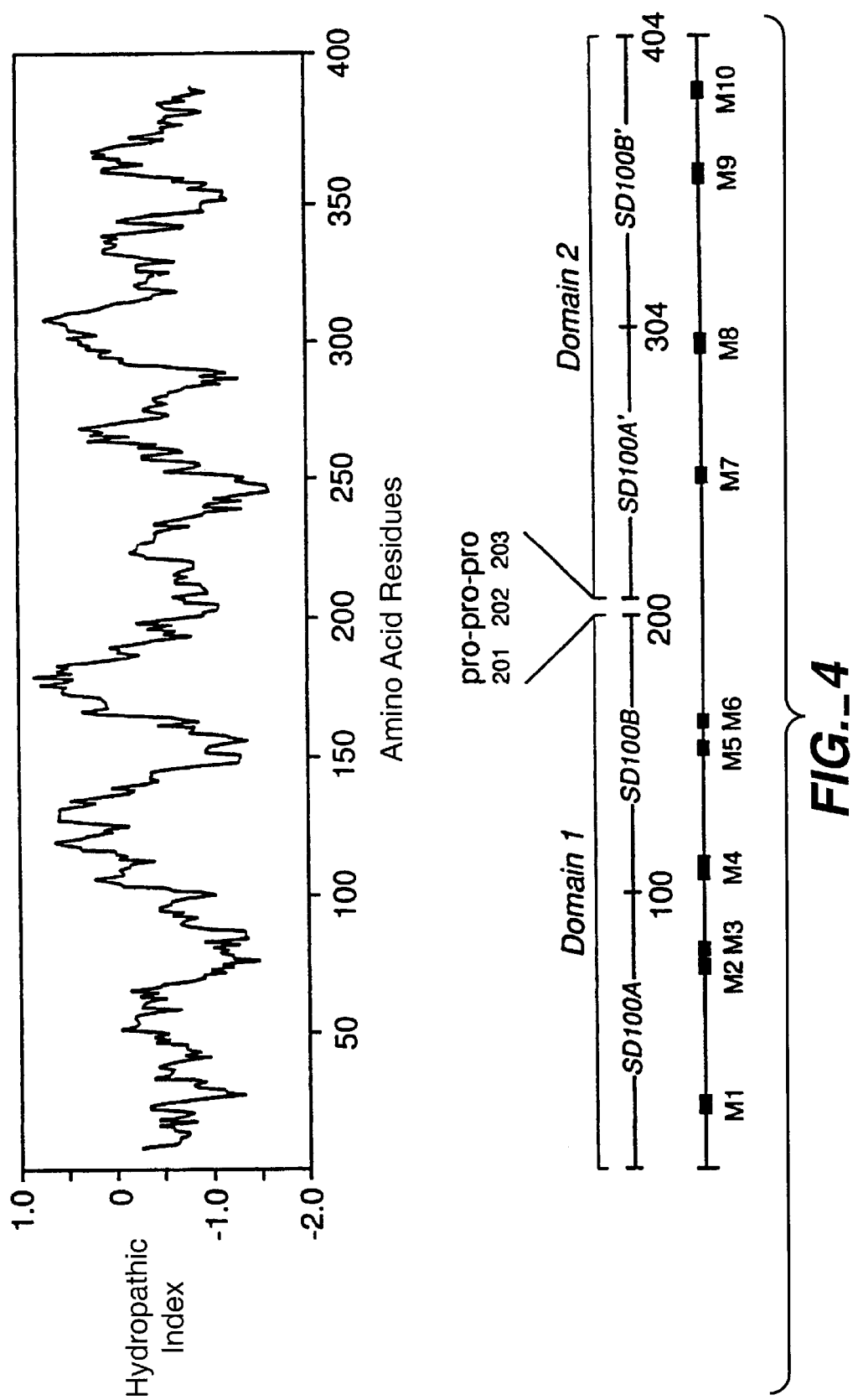
FIG._4

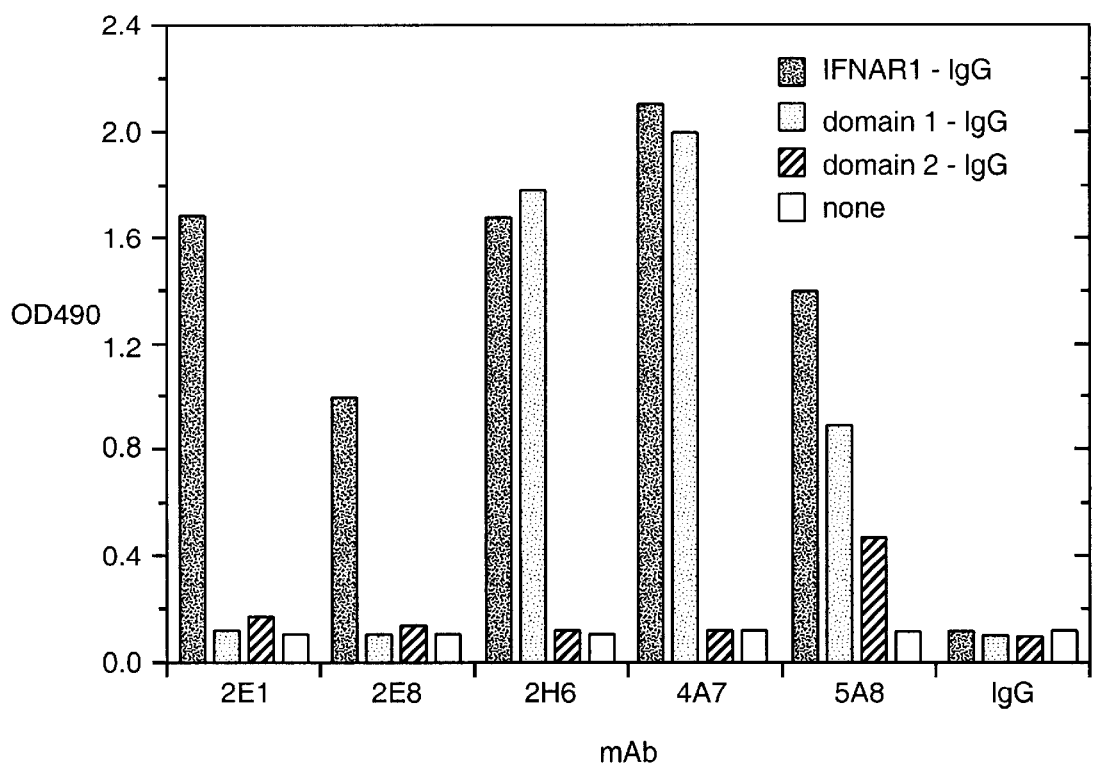
FIG._5

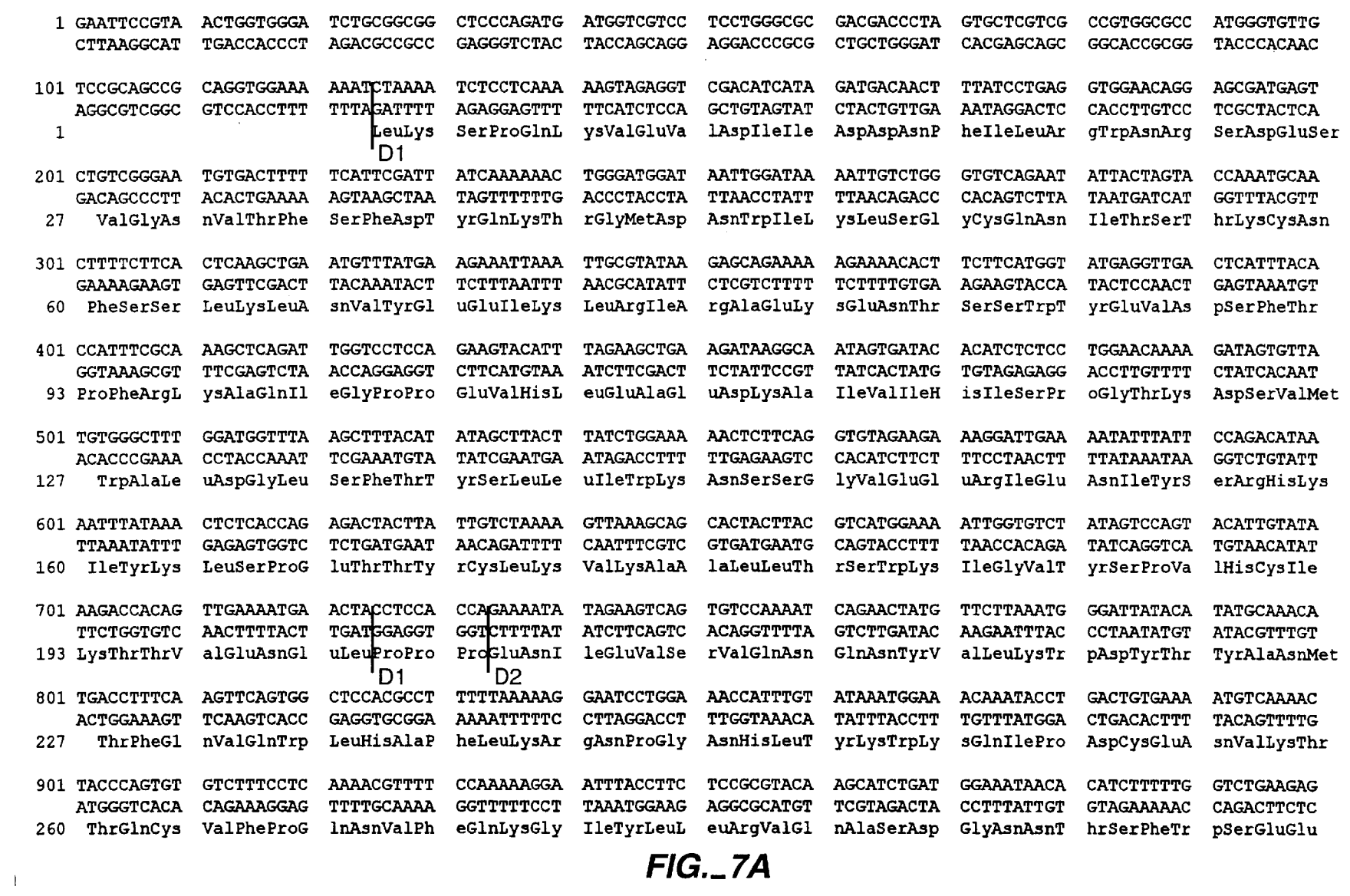

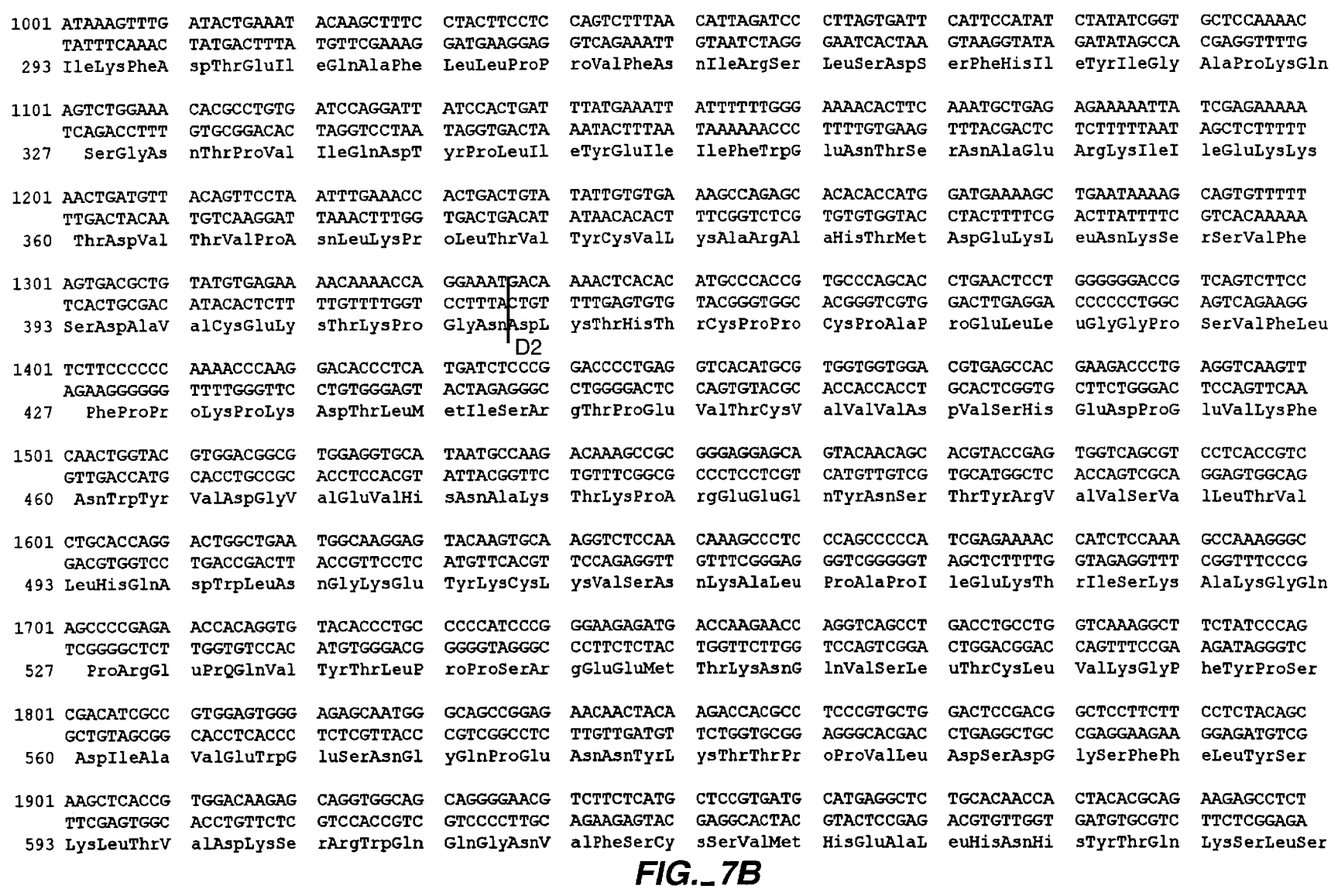

```
2001 CCCTGTCTCC GGGTAAATGA GTGCGACGGC CCTAGAGTCG ACCTGCAGAA GCTTAGAACC GAGGGGCCGC CATGCCCAA CTTGTTTATT GCAGCTTATA
     GGGACAGAGG CCCATTTACT CACGCTGCCG GGATCTCAGC TGGACGTCTT CGAATCTTGG CTCCCCGGCG GTACCGGGTT GAACAAATAA CGTCGAATAT
 627     LeuSerPr oGlyLysOP*

2101 ATGGTTACAA ATAAAGCAAT AGCATCACAA ATTTCACACA ACTGCGAGAA GCTTAGAACC ATTCTAGTTG TGGTTTGTCC AAACTCATCA ATGTATCTTA
     TACCAATGTT TATTTCGTTA TCGTAGTGTT TAAAGTGTGT TGACGCTCTT CGAATCTTGG TAAGATCAAC ACCAAACAGG TTTGAGTAGT TACATAGAAT

2201 TCATGTCTGG ATCGATCGGG AATTAATTCG GCGCAGCACC ATGGCCTGAA ATAACCTCTG AAAGAGGAAC TTGGTTAGGT ACCTTCTGAG GCGAAAGAA
     AGTACAGACC TAGCTAGCCC TTAATTAAGC CGCGTCGTGG TACCGGACTT TATTGGAGAC TTTCTCCTTG AACCAATCCA TGGAAGACTC CGCCTTTCTT

2301 CCAGTCTGTGG AATGTGTGTC AGTTAGGGTG TGGAAAGTCC CCAGGCTCCC CAGCAGGCAG AAGTATGCAA AGCATGCATC TCAATTAGTC AGCAACCAGG
     GGTCGACACC TTACACACAG TCAATCCAC ACCTTTCAGG GGTCCGAGGG GTCGTCCGTC TTCATACGTT TCGTACGTAG AGTTAATCAG TCGTTGGTCC

2401 TGTGGAAAGT CCCCAGGCTC CCAGCAGGCG AGAAGTATGC AAAGCATGCA TCTCAATTAG TCAGCAACCA TAGTCCGCC CCTAACTCCG AGCTATTCCA
     ACACCTTTCA GGGGTCCGAG GGTCGTCCGC TCTTCATACG TTTCGTACGT AGAGTTAATC AGTCGTTGGT ATCAGGGCGG GGATTGAGGC TCGATAAGT

2501 CCCTAACTCC GAGCCAGTTCC GCCCATTCTC CGCCCATTCTC CTGACTAATT TTTTTTATT ATGCAGAGCC CGAGGCCGCC TCGGCCTCTG TGGGAAAACC
     GGGATTGAGG CGGGTCAAGG CGGGTAGAAG GCGGGTAGAAG GACTGATTAA AAAAAAATAA TACGTCTCCG GCTCCGGCGG AGCCGGAGAC ACCCTTTTGG

2601 GAAGTAGTGA GGAGGCTTTT TTGGAGGCCT AAAAAGCTGT TAACAGCTTG GCACTGGCCG TCGTTTTACA ACTCGTGAC TGGGAAAACC AACAGTTGCG
     CTTCATCACT CCTCCGAAAA AACCTCCGGA TTTTTCGACA ATTGTCGAAC CGTGACCGGC AGCAAAATGT TGCAGCACTG ACCCTTTTGG TTGTCAACGC

2701 CTGGCCTTAC CCAACTTAAT CGCCCTTGCAG CACATCCCCC CTTCGCCAGC TGGCGTAATA GCGAAGAGGC CCGACACCGAT CGCCCTTCCC TACGCGCCCT
     GACCGGAATG GGTTGAATTA GCGGAACGTC GTGTAGGGGG GAAGCGTCG ACCGGATTAT CGCTTCTCCG GGCGTGGCTA GCGGGAAGGG ATGCGCGGGA

2801 TAGCCTGAAT GGCGAATGGC GCCTGATGCG GTATTTTCTC CTTACGCATC TGTGCGGTAT TTCACACCGC ATACGTCAAA GCAACCATAG TCTTCCCTTC
     ATCGGACTTA CCGCTTACCG CGGACTACGC CATAAAAGAG GAATGCGTAG ACACGCCATA AAGTGTGGCG TATGCAGTTT CGTTGGTATC AGAAGGGAAG

2901 GTAGCGGCGC ATTAAGCGCG GCGGGTGTGG TGGTTACGCG CAGCGTGACC GCTACACTTG CCAGCGCCCT AGCGCCCGCT CCTTTCGCTT CCCCAAAAAA
     CATCGCCGCG TAATTCGCGC CGCCCACACC ACCAATGCGC GTCGCACTGG CGATGTGAAC GGTCGCGGGA TCGCGGGCGA GGAAAGCGAA GGGGTTTTTT

3001 CTTTCTCGCC ACGTTCGCCG GCTTTCCCCG TCAAGCTCTA AATCGGGGGC TCCCTTTAGG GTTCCGATTT AGTGCTTTAC GGCACCCTGA CCCAAAAAA
     GAAAGAGCGG TGCAAGCGGC CGAAAGGGGC AGTTCGAGAT TTAGCCCCCG AGGGAAATCC CAAGGCTAAA TCACGAAATG CCGTGGAGCT GGGTTTTTT

3101 CTTGATTTGG GTGATGGTTC ACGTAGTGGG CCATCGCCCT GATAGACGGT TTTTCGCCCT TTGACGTTGG AGTCCACGTT CTTTAATAGT GGACTCTTGT
     GAACTAAACC CACTACCAAG TGCATCACCC GGTAGCGGGA CTATCTGCCA AAAGCGGGAA AACTGCAACT TCAGGTGCAA GAAATTATCA CCTGAGAACA

3201 TCCAAACTGG AACAACACTC AACCCTATCT CGGGCTATTC TTTTGATTTA TAAGGGATTT TGCCGATTTC GGCCTATTGG TTAAAAAATG AGCTGATTTA
     AGGTTTGACC TTGTTGTGAG TTGGGATAGA GCCCGATAAG AAAACTAAAT ATTCCCTAAA ACGGGCTAAAG CCGGATAACC AATTTTTTAC TCGACTAAAT
```

*FIG._7C*

```
3301 ACAAAAATTT AACGCGAATT TTAACAAAAT ATTAACGTTT ACAATTTTAT GGTGCACTCT CAGTACAATC TGCTCTGATG CCGCATAGTT AAGCCAACTC
     TGTTTTTAAA TTGCGCTTAA AATTGTTTTA TAATTGCAAA TGTTAAAATA CCACGTGAGA GTCATGTTAG ACGAGACTAC GGCGTATCAA TTCGGTTGAG

3401 CGTTATCGCT ACGTGACTGG GTCATGGCTG CGCCCCGACA CCCGCCAACA CCCGCTGACG CGCCCTGACG GGCTTGTCTG CTCCCGGCAT CCGCTTACAG
     GCGATAGCGA TGCACTGACC CAGTACCGAC GCGGGGCTGT GGGCGGTTGT GGGCGACTGC GCGGGACTGC CCGAACAGAC GAGGGCCGTA GGCGAATGTC

3501 ACAAGCTGTG ACCGTCTCCG GGAGCTGCAT GTGTCAGAGG TTTTCACCGT CATCACCGAA ACGCGCGAGG CAGTATTCTT GAAGACGAAA GGGCCTCGTG
     TGTTCGACAC TGGCAGAGGC CCTCGACGTA CACAGTCTCC AAAAGTGGCA GTAGTGGCTT TGCGCGCTCC GTCATAAGAA CTTCTGCTTT CCCGGAGCAC

3601 ATACGCCTAT TTTTATAGGT TAATGTCATG ATAATAATGG TTTCTTAGAC GTCAGGTGCG ACTTTTCGGG GAAATGTGCG CGGAACCCCT ATTTGTTTAT
     TATGCGGATA AAAATATCCA ATTACAGTAC TATTATTACC AAAGAATCTG CAGTCCACCG TGAAAAGCCC CTTTACACGC GCCTTGGGGA TAAACAAATA

3701 TTTTCTAAAT ACATTCAAAT ATGTATCCGC TCATGAGACA ATAACCCTGA TAAAATGCTTC AATAATATTG AAAAAGGAAG AGTATGAGTA TTCAACATTT
     AAAAGATTTA TGTAAGTTTA TACATAGGCG AGTACTCTGT TATTGGGACT ATTTACGAAG TTATTATAAC TTTTTCCTTC TCATACTCAT AAGTTGTAAA

3801 CCGTGTCGCC CTTATTCCCT TTTTTGCGCT ATTTTGCCTT CCTGTTTTTG CTCACCCAGA AACGCTGGTG AAAGTAAAAG ATGCTGAAGA TCAGTTGGGT
     GGCACAGCGG GAATAAGGGA AAAAACGCGA TAAAACGGAA GGACAAAAAC GAGTGGGTCT TTGCGACCAC TTTCATTTTC TACGACTTCT AGTCAACCCA

3901 GCACGAGTGG GTTACATGAC ACTGGATCTC AACAGCGGTA AGATCCTTGA GAGTTTTCGC CCCGAAGAAC GTTTTCCAAT GATGAGCACT TTTAAAGTTC
     CGTGCTCACC CAATGTAGCT TGACCTAGAG TTGTCGCCAT TCTAGGAACT CTCAAAAGCG GGGCTTCTTG CAAAAGGTTA CTACTCGTGA AAATTTCAAG

4001 TGCTATGTGG CCGGGTATTA TCCCGTGATG AGAGCAACTC GGTCGCCGCA TACACTATTC TCAGAATGAC TTGGTTGAGT ACTTACTCTA ACTCACCAGT
     ACGATACACC GCCCATAAT AGGGCACTAC TCTCGTTGAG CCAGCGGCGT ATGTGATAAG AGTCTTACTG AACCAACTCA TGAATGAGAT TGAGTGGTCA

4101 CACAGAAAAG CATCTTACGG ATGGCATGAC AGTAAGAGAA TTATGCAGTG CTGCCATAAC CATGAGTGAT AACACTGCGG CCAACTTACT TCTGACAACG
     GTGTCTTTTC GTAGAATGCC TACCGTACTG TCATTCTCTT AATACGTCAC GACGGTATTG GTACTCACTA TTGTGACGCC GGTTGAATGA AGACTGTTGC

4201 ATCGGAGGAC CGAAGGAGCT AACCGCTTTT TTGCACAACA TGGGGGATCA TGTAACTCGC CTTGATCGTT GGGAACCGGA GCTGAATGAA GCCATACCAA
     TAGCCTCCTG GCTTCCTCGA TTGGCGAAAA ACCGTGTTGT ACCCCCTAGT ACATTGAGCG GAACTAGCAA CCCTTGGCCT CGACTACTT CGGTATGGTT

4301 ACGACGAGCG TGACACCACG ATGCCAGCAG CAATGGCAAC AACGTTGCGC AAACTATTAA CTGGGGAACT ACTTACTCTA GCTTCCCGGC AACAATTAAT
     TGCTGCTCGC ACTGTGGTGC TACGGTCGTC GTTACCGTTG TTGCAACGCG TTTGATAATT GACCCCTTGA TGAATGAGAT CGAAGGGCCG TTGTTAATTA

4401 AGACTGGATG GAGGCGGATA AAGTTGCAGG ACCACTTCTG CGCTCGGCCC TTCCGGCTGG CTGGTTTATT GCTGATAAAT CTGGAGCCGG TGAGCTGGG
     TCTGACCTAC CTCCGCCTAT TTCAACGTCC TGGTGAAGAC GCGAGCCGGG AAGGCCGACC GACCAAATAA CGACTATTTA GACCTCGGCC ACTCGACCCC

4501 TCTTCGCGGTA TCATTGCAGC ACTGGGGCCA GATGGTAAGC CCTCCCGTAT CGTAGTTATC TACAGACGGG GGAGTCAGGC AACTATGGAT GAACGAAATA
     AGAGGCCAT AGTAACGTCG TGACCCCGGT CTACCATTCG GGAGGGCATA GCATCAATAG ATGTGCTGCC CCTCAGTCCG TTGATACCTA CTTGCTTTAT

4601 GACAGATCGC TGAGATAGGT GCCTCACTGA TTAAGCATTG GTAACTGTCA GACCAAGTTT ACTCATATAT ACTTAGATT GATTAAAAC TTCATTTTA
     CTGTCTAGCG ACTCTATCCA CGGAGTGACT AATTCGTAAC CATTGACAGT CTGGTTCAAA TGAGTATATA TGAATCTAA CTAAATTTTG AAGTAAAAT
```

FIG._7D

```
4701 ATTTAAAAGG ATCTAGGTGA AGATCCTTTT TGATAATCTC ATGACCAAAA TCCCTTAACG TGAGTTTTCG TTCCACTGAG CGTCAGACCC CGTAGAAAAG
     TAAATTTTCC TAGATCCACT TCTAGGAAAA ACTATTAGAG TACTGGTTTT AGGGAATTGC ACTCAAAAGC AAGGTGACTC GCAGTCTGGG GCATCTTTTC

4801 ATCAAAGGAT CTTCTTGAGA TCCTTTTTTT CTGCGCGTAA TCTGCTGCTT GCAAACAAAA AAACCACCGC TACCAGCGGT GGTTTGTTTG CCGGATCAAG
     TAGTTCCTA  GAAGAACTCT AGGAAAAAAA GACGCGCATT AGACGACGAA CGTTTGTTTT TTTGGTGGCG ATGGTCGCCA CCAAACAAAC GGCCTAGTTC

4901 AGCTACCAAC TCTTTTTCCG AAGGTAACTG GCTTCAGCAG AGCGCAGATA CCAAATACTG TCCTTCTAGT GTAGCCGTAG TTAGGCCACC ACTTCAAGAA
     TCGATGGTTG AGAAAAAGGC TTCCATTGAC CGAAGTCGTC TCGCGTCTAT GGTTTATGAC AGGAAGATCA CATCGGCATC AATCCGGTGG TGAAGTTCTT

5001 CTCTGTAGCA CCGCCTACAT ACCTCGCTCT GCTAATCCTG TTACCAGTGG CTGCTGCCAG TGGCGATAAG TCGTGTCTTA CCGGGTTGGA CTCAAGACGA
     GAGACATCGT GGCGGATGTA TGGAGCGAGA CGATTAGGAC AATGGTCACC GACGACGGTC ACCGCTATTC AGCACAGAAT GGCCCAACCT GAGTTCTGCT

5101 TAGTTACCGG ATAAGGCGCA GCGGTCGGGC TGAACGGGGG GTTCGTGCAC ACAGCCCAGC TTGGAGCGAA CGACCTACAC TTAGGCCACC TACCTACAGC
     ATCAATGCCC TATTCCGCGT CGCCAGCCCG ACTTGCCCCC CAAGCACGTG TGTCGGGTCG AACCTCGCTT GCTGACTCT  ATGGATGTCG

5201 GTGAGCATTG AGAAAGCGCC ACGCTTCCCG AAGGGAGAAA TATCCGGTAA GGCGGACAGG GCGCCAGGGT CGGAACAGGA GAGCGCACGA GGGAGCTTCC
     CACTCGTAAC TCTTTCGCGG TGCGAAGGGC TTCCCTCTTT ATAGGCCATT CCGCCTGTCC CGCCGTCCCA GCCTTGTCCT CTCGCGTGCT CCCTCGAAGG

5301 AGGGGGAAAC GCCTGGTATC TTTATAGTCC TGTCGGGTTT CGCCACCTCT GACTTGAGCG TCGATTTTTG CAGGGGGGCG GAGCCTATGG
     TCCCCCTTTG CGGACCATAG AAATATCAGG ACAGCCCAAA GCGGTGGAGA CTGAACTCGC AGCTAAAAAC GTCCCCCGC  CTCGGATACC

5401 AAAAACGCCA GCAACGCGGC CTTTTTACGG TTCCTGGCCT TTTGCTGGCC TTTTGCTCAC ATGTTCTTTC CTGGTTATC  CCCTGATTCT GTGGATAACC
     TTTTTGCGGT CGTTGCGCCG GAAAAATGCC AAGGACCGGA AAACGACCGG AAAACGAGTG TACAAGAAAG GACGCAATAG GGGACTAAGA CACCTATTGG

5501 GTATTACCGC CTTTGAGTGA GCTGATACCG CTCGCCGCAG CCGAACGACC GAGCGCAGCG AGTCAGTGAG CGAGGAAGCG GAAGAGCGCC CAATACGCAA
     CATAATGGCG GAAACTCACT CGACTATGGC GAGCGGCGTC GGCTTGCTGG CTCGCGTCGC TCAGTCACTC GCTCCTTCGC CTTCTCGCGG GTTATGCGTT

5601 ACCGCCTCTC CCCGCGCGTT GGCCGATTCA TTAATCCAGC TGGCACGACA GGTTTCCCGA CTGGAAAGCG GGCAGTGAGC GCAACGCAAT TAATGTGAGT
     TGGCGGAGAG GGGCGCGCAA CCGGCTAAGT AATTAGGTCG ACCGTGCTGT CCAAAGGGCT GACCTTTCGC CGTCACTCG  CGTTGCGTTA ATTACACTCA

5701 TACCTCACTC ATTAGGCACC CCAGGCTTTA CACTTTATGC TTCCGGCTCG TATGTTGTGT GGAATTGTGA GCGGATAACA ATTTCACACA GGAAACAGCT
     ATGGAGTGAG TAATCCGTGG GGTCCGAAAT GTGAAATACG AAGGCCGAGC ACACAACACA CCTTAACACT CGCCTATTGT TAAAGTGTGT CCTTTGTCGA

5801 ATGACCATGA TTACGAATTA ATTCGAGCTC GATTATTGAC TAGTTATTAA TAGTAATCAA TTACGGGGTC ATTAGTTCAT AGCCCATATA
     TACTGGTACT AATGCTTAAT TAAGCTCGAG CTAATAACTG ATCAATAATT ATCATTAGTT AATGCCCCAG TAATCAAGTA TCGGGTATAT

5901 TGGAGTTCCG CGTTACATAA CTTACGGTAA ATGGCCCGCC TGGCTGACCG CCCAACGACC CCCGCCCATT GACGTCAATG ATGACGTATG TTCCCATAGT
     ACCTCAAGGC GCAATGTATT GAATGCCATT TACCGGGCGG ACCGACTGGC GGGTTGCTGG GGGCGGGTAA CTGCAGTTAC TGCAGTATCT AAGGGTATCA

6001 AACGCCAATA GGGACTTTCC ATTGACGTCA ATGGGTGGAG TATTTACGGT AAACTGCCCA CTTGGCAGTA CATCAAGTGT ATCATATGCC AAGTACGCCC
     TTGCGGTTAT CCCTGAAAGG TAACTGCAGT TACCCACCTC ATAAATGCCA TTTGACGGGT GAACCGTCAT GTAGTTCACA TAGTATACGG TTCATGCGGG
```

FIG. _7E

```
6101  CCTATTGACG  TCAATGACGG  TAAATGGCCC  GCCTGGCATT  ATGCCCAGTA  CATGACCTTA  TGGGACTTTC  CTACTTGGCA  GTACATCTAC  GTATTAGTCA
      GGATAACTGC  AGTTACTGCC  ATTTACCGGG  CGGACCGTAA  TACGGGTCAT  GTACTGGAAT  ACCCTGAAAG  GATGAACCGT  CATGTAGATG  CATAATCAGT

6201  TCGCTATTAC  CATGGTGATG  CGGTTTTGGC  AGTACATCAA  TGGGCGTGGA  TAGCGGTTTG  ACTCACGGGG  ATTTCCAAGT  CTCCACCCCA  TTGACGTCAA
      AGCGATAATG  GTACCACTAC  GCCAAAACCG  TCATGTAGTT  ACCCGCACCT  ATCGCCAAAC  TGAGTGCCCC  TAAAGGTTCA  GAGGTGGGGT  AACTGCAGTT

6301  TGGGAGTTTG  TTTTGGCACC  AAAATCAACG  GGACTTTCCA  AAATGTCGTA  ACAACTCCGC  CCCATTGACG  CAAATGGGCG  GTAGGCGTGT  ACGGTGGGAG
      ACCCTCAAAC  AAAACCGTGG  TTTTAGTTGC  CCTGAAAGGT  TTTACAGCAT  TGTTGAGGCG  GGGTAACTGC  GTTTACCCGC  CATCCGCACA  TGCCACCCTC

6401  GTCTATATAA  GCAGAGCTCG  TTTAGTGAAC  CGTCAGATCG  CCTGGAGACG  CCATCCACGC  TGTTTTGACC  TCCATAGAAG  ACACCGGGAC  CGATCCAGCC
      CAGATATATT  CGTCTCGAGC  AAATCACTTG  GCAGTCTAGC  GGACCTCTGC  GGTAGGTGCG  ACAAAACTGG  AGGTATCTTC  TGTGGCCCTG  GCTAGGTCGG

6501  TCCGCGGCCG  GGAACGGTGC  ATTGGAACGC  GGATTCCCCG  TGCCAAGAGT  GACGTAAGTA  CCGCCTATAG  AGTCTATAGG  CCCACCCCCT  TGGCTCGTTA
      AGGCGCCGGC  CCTTGCCACG  TAACCTTGCG  CCTAAGGGGC  ACGGTTCTCA  CTGCATTCAT  GGCGGATATC  TCAGATATCC  GGGTGGGGGA  ACCGAGCAAT

6601  GAACGCGGCT  ACAATTAATA  CATAACCTTA  TGTATCATAC  ACATACGATT  TAGGTGACAC  TATAGAATAA  CATCCACTTT  GCCTTTCTCT  CCACAGGTGT
      CTTGCGCCGA  TGTTAATTAT  GTATTGGAAT  ACATAGTATG  TGTATGCTAA  ATCCACTGTG  ATATCTTATT  CGGAGTGAAA  CGGAAAGAGA  GGTGTCCACA

6701  CCACTCCCAG  GTCCAACTGC  AGGCCATGGC  GGCCATCGAT  T
      GGTGAGGGTC  CAGGTTGACG  TCCGGTACCG  CCGGTAGCTA  A
```

FIG._7F

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 7 amino acids
      (B) TYPE: Amino Acid
      (D) TOPOLOGY: Linear (xi) SEQUENCE DESCRIPTION: SEQ ID NO:1:

```
Arg Trp Asn Arg Ser Asp Glu
 1               5       7

(2) INFORMATION FOR SEQ ID NO:2:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:2:

Ala Trp Asn Ala Ser Ala Ala
 1               5       7

(2) INFORMATION FOR SEQ ID NO:3:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:3:

Glu Glu Ile Lys Leu Arg
 1               5   6

(2) INFORMATION FOR SEQ ID NO:4:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:4:

Ala Ala Ile Ala Leu Ala
 1               5   6

(2) INFORMATION FOR SEQ ID NO:5:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:5:

Arg Ala Glu Lys Glu
 1               5

(2) INFORMATION FOR SEQ ID NO:6:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:6:

Ala Ala Ala Ala Ala
 1               5

(2) INFORMATION FOR SEQ ID NO:7:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO:7:

Glu Val His Leu Glu Ala Glu Asp Lys
```

```
              1               5               9
```

(2) INFORMATION FOR SEQ ID NO:8:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO:8:

```
Ala Val Ala Leu Ala Ala Ala Ala Ala
 1               5               9
```

(2) INFORMATION FOR SEQ ID NO:9:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:9:

```
Glu Glu Arg Ile Glu
 1               5
```

(2) INFORMATION FOR SEQ ID NO:10:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:10:

```
Ala Ala Ala Ile Ala
 1               5
```

(2) INFORMATION FOR SEQ ID NO:11:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:11:

```
Arg His Lys Ile Tyr Lys
 1               5   6
```

(2) INFORMATION FOR SEQ ID NO:12:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:12:

```
Ala Ala Ala Ile Tyr Ala
 1               5   6
```

(2) INFORMATION FOR SEQ ID NO:13:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:13:

```
His Leu Tyr Lys Trp Lys
 1               5   6
```

(2) INFORMATION FOR SEQ ID NO:14:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:14:

```
Ala Leu Tyr Ala Trp Ala
 1           5   6
```

(2) INFORMATION FOR SEQ ID NO:15:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:15:

```
Glu Glu Ile Lys Phe Asp Thr Glu
 1           5               8
```

(2) INFORMATION FOR SEQ ID NO:16:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:16:

```
Ala Ala Ile Ala Phe Ala Thr Ala
 1           5               8
```

(2) INFORMATION FOR SEQ ID NO:17:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:17:

```
Glu Arg Lys Ile Ile Glu Lys Lys
 1           5               8
```

(2) INFORMATION FOR SEQ ID NO:18:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:18:

```
Ala Ala Ala Ile Ile Ala Ala Ala
 1           5               8
```

(2) INFORMATION FOR SEQ ID NO:19:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:19:

```
Asp Glu Lys Leu Asn Lys
 1           5   6
```

(2) INFORMATION FOR SEQ ID NO:20:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:20:

```
Ala Ala Ala Leu Asn Ala
 1           5   6
```

(2) INFORMATION FOR SEQ ID NO:21:

(i) SEQUENCE CHARACTERISTICS:
        (A) LENGTH: 6741 base pairs
        (B) TYPE: Nucleic Acid
        (C) STRANDEDNESS: Double
        (D) TOPOLOGY: Linear (xi) SEQUENCE DESCRIPTION: SEQ ID NO:21:

```
GAATTCCGTA ACTGGTGGGA TCTGCGGCGG CTCCCAGATG ATGGTCGTCC         50

TCCTGGGCGC GACGACCCTA GTGCTCGTCG CCGTGGCGCC ATGGGTGTTG         100

TCCGCAGCCG CAGGTGGAAA AAATCTAAAA TCTCCTCAAA AAGTAGAGGT         150

CGACATCATA GATGACAACT TTATCCTGAG GTGGAACAGG AGCGATGAGT         200

CTGTCGGGAA TGTGACTTTT TCATTCGATT ATCAAAAAAC TGGGATGGAT         250

AATTGGATAA AATTGTCTGG GTGTCAGAAT ATTACTAGTA CCAAATGCAA         300

CTTTTCTTCA CTCAAGCTGA ATGTTTATGA AGAAATTAAA TTGCGTATAA         350

GAGCAGAAAA AGAAAACACT TCTTCATGGT ATGAGGTTGA CTCATTTACA         400

CCATTTCGCA AAGCTCAGAT TGGTCCTCCA GAAGTACATT TAGAAGCTGA         450

AGATAAGGCA ATAGTGATAC ACATCTCTCC TGGAACAAAA GATAGTGTTA         500

TGTGGGCTTT GGATGGTTTA AGCTTTACAT ATAGCTTACT TATCTGGAAA         550

AACTCTTCAG GTGTAGAAGA AAGGATTGAA AATATTTATT CCAGACATAA         600

AATTTATAAA CTCTCACCAG AGACTACTTA TTGTCTAAAA GTTAAAGCAG         650

CACTACTTAC GTCATGGAAA ATTGGTGTCT ATAGTCCAGT ACATTGTATA         700

AAGACCACAG TTGAAAATGA ACTACCTCCA CCAGAAAATA TAGAAGTCAG         750

TGTCCAAAAT CAGAACTATG TTCTTAAATG GGATTATACA TATGCAAACA         800

TGACCTTTCA AGTTCAGTGG CTCCACGCCT TTTTAAAAAG GAATCCTGGA         850

AACCATTTGT ATAAATGGAA ACAAATACCT GACTGTGAAA ATGTCAAAAC         900

TACCCAGTGT GTCTTTCCTC AAAACGTTTT CCAAAAAGGA ATTTACCTTC         950

TCCGCGTACA AGCATCTGAT GGAAATAACA CATCTTTTTG GTCTGAAGAG         1000

ATAAAGTTTG ATACTGAAAT ACAAGCTTTC CTACTTCCTC CAGTCTTTAA         1050

CATTAGATCC CTTAGTGATT CATTCCATAT CTATATCGGT GCTCCAAAAC         1100

AGTCTGGAAA CACGCCTGTG ATCCAGGATT ATCCACTGAT TTATGAAATT         1150

ATTTTTTGGG AAAACACTTC AAATGCTGAG AGAAAAATTA TCGAGAAAAA         1200

AACTGATGTT ACAGTTCCTA ATTTGAAACC ACTGACTGTA TATTGTGTGA         1250

AAGCCAGAGC ACACACCATG GATGAAAAGC TGAATAAAAG CAGTGTTTTT         1300

AGTGACGCTG TATGTGAGAA AACAAAACCA GGAAATGACA AAACTCACAC         1350

ATGCCCACCG TGCCCAGCAC CTGAACTCCT GGGGGGACCG TCAGTCTTCC         1400
```

```
TCTTCCCCCC AAAACCCAAG GACACCCTCA TGATCTCCCG GACCCCTGAG         1450

GTCACATGCG TGGTGGTGGA CGTGAGCCAC GAAGACCCTG AGGTCAAGTT         1500

CAACTGGTAC GTGGACGGCG TGGAGGTGCA TAATGCCAAG ACAAAGCCGC         1550

GGGAGGAGCA GTACAACAGC ACGTACCGAG TGGTCAGCGT CCTCACCGTC         1600

CTGCACCAGG ACTGGCTGAA TGGCAAGGAG TACAAGTGCA AGGTCTCCAA         1650

CAAAGCCCTC CCAGCCCCCA TCGAGAAAAC CATCTCCAAA GCCAAAGGGC         1700

AGCCCCGAGA ACCACAGGTG TACACCCTGC CCCCATCCCG GGAAGAGATG         1750

ACCAAGAACC AGGTCAGCCT GACCTGCCTG GTCAAAGGCT TCTATCCCAG         1800

CGACATCGCC GTGGAGTGGG AGAGCAATGG GCAGCCGGAG AACAACTACA         1850

AGACCACGCC TCCCGTGCTG GACTCCGACG GCTCCTTCTT CCTCTACAGC         1900

AAGCTCACCG TGGACAAGAG CAGGTGGCAG CAGGGGAACG TCTTCTCATG         1950

CTCCGTGATG CATGAGGCTC TGCACAACCA CTACACGCAG AAGAGCCTCT         2000

CCCTGTCTCC GGGTAAATGA GTGCGACGGC CCTAGAGTCG ACCTGCAGAA         2050

GCTTAGAACC GAGGGGCCGC CATGGCCCAA CTTGTTTATT GCAGCTTATA         2100

ATGGTTACAA ATAAAGCAAT AGCATCACAA ATTTCACAAA TAAAGCATTT         2150

TTTTCACTGC ATTCTAGTTG TGGTTTGTCC AAACTCATCA ATGTATCTTA         2200

TCATGTCTGG ATCGATCGGG AATTAATTCG GCGCAGCACC ATGGCCTGAA         2250

ATAACCTCTG AAAGAGGAAC TTGGTTAGGT ACCTTCTGAG GCGGAAAGAA         2300

CCAGCTGTGG AATGTGTGTC AGTTAGGGTG TGGAAAGTCC CCAGGCTCCC         2350

CAGCAGGCAG AAGTATGCAA AGCATGCATC TCAATTAGTC AGCAACCAGG         2400

TGTGGAAAGT CCCCAGGCTC CCCAGCAGGC AGAAGTATGC AAAGCATGCA         2450

TCTCAATTAG TCAGCAACCA TAGTCCCGCC CCTAACTCCG CCCATCCCGC         2500

CCCTAACTCC GCCCAGTTCC GCCCATTCTC CGCCCCATGG CTGACTAATT         2550

TTTTTTATTT ATGCAGAGGC CGAGGCCGCC TCGGCCTCTG AGCTATTCCA         2600

GAAGTAGTGA GGAGGCTTTT TTGGAGGCCT AGGCTTTTGC AAAAAGCTGT         2650

TAACAGCTTG GCACTGGCCG TCGTTTTACA ACGTCGTGAC TGGGAAAACC         2700

CTGGCGTTAC CCAACTTAAT CGCCTTGCAG CACATCCCCC CTTCGCCAGC         2750

TGGCGTAATA GCGAAGAGGC CCGCACCGAT CGCCCTTCCC AACAGTTGCG         2800

TAGCCTGAAT GGCGAATGGC GCCTGATGCG GTATTTTCTC CTTACGCATC         2850

TGTGCGGTAT TTCACACCGC ATACGTCAAA GCAACCATAG TACGCGCCCT         2900

GTAGCGGCGC ATTAAGCGCG GCGGGTGTGG TGGTTACGCG CAGCGTGACC         2950

GCTACACTTG CCAGCGCCCT AGCGCCCGCT CCTTTCGCTT TCTTCCCTTC         3000

CTTTCTCGCC ACGTTCGCCG GCTTTCCCCG TCAAGCTCTA AATCGGGGGC         3050

TCCCTTTAGG GTTCCGATTT AGTGCTTTAC GGCACCTCGA CCCCAAAAAA         3100

CTTGATTTGG GTGATGGTTC ACGTAGTGGG CCATCGCCCT GATAGACGGT         3150

TTTTCGCCCT TTGACGTTGG AGTCCACGTT CTTTAATAGT GGACTCTTGT         3200

TCCAAACTGG AACAACACTC AACCCTATCT CGGGCTATTC TTTTGATTTA         3250

TAAGGGATTT TGCCGATTTC GGCCTATTGG TTAAAAAATG AGCTGATTTA         3300

ACAAAAATTT AACGCGAATT TTAACAAAAT ATTAACGTTT ACAATTTTAT         3350
```

| | |
|---|---|
| GGTGCACTCT CAGTACAATC TGCTCTGATG CCGCATAGTT AAGCCAACTC | 3400 |
| CGCTATCGCT ACGTGACTGG GTCATGGCTG CGCCCCGACA CCCGCCAACA | 3450 |
| CCCGCTGACG CGCCCTGACG GGCTTGTCTG CTCCCGGCAT CCGCTTACAG | 3500 |
| ACAAGCTGTG ACCGTCTCCG GGAGCTGCAT GTGTCAGAGG TTTTCACCGT | 3550 |
| CATCACCGAA ACGCGCGAGG CAGTATTCTT GAAGACGAAA GGGCCTCGTG | 3600 |
| ATACGCCTAT TTTTATAGGT TAATGTCATG ATAATAATGG TTTCTTAGAC | 3650 |
| GTCAGGTGGC ACTTTTCGGG GAAATGTGCG CGGAACCCCT ATTTGTTTAT | 3700 |
| TTTTCTAAAT ACATTCAAAT ATGTATCCGC TCATGAGACA ATAACCCTGA | 3750 |
| TAAATGCTTC AATAATATTG AAAAAGGAAG AGTATGAGTA TTCAACATTT | 3800 |
| CCGTGTCGCC CTTATTCCCT TTTTTGCGGC ATTTTGCCTT CCTGTTTTTG | 3850 |
| CTCACCCAGA AACGCTGGTG AAAGTAAAAG ATGCTGAAGA TCAGTTGGGT | 3900 |
| GCACGAGTGG GTTACATCGA ACTGGATCTC AACAGCGGTA AGATCCTTGA | 3950 |
| GAGTTTTCGC CCCGAAGAAC GTTTTCCAAT GATGAGCACT TTTAAAGTTC | 4000 |
| TGCTATGTGG CGCGGTATTA TCCCGTGATG ACGCCGGGCA AGAGCAACTC | 4050 |
| GGTCGCCGCA TACACTATTC TCAGAATGAC TTGGTTGAGT ACTCACCAGT | 4100 |
| CACAGAAAAG CATCTTACGG ATGGCATGAC AGTAAGAGAA TTATGCAGTG | 4150 |
| CTGCCATAAC CATGAGTGAT AACACTGCGG CCAACTTACT TCTGACAACG | 4200 |
| ATCGGAGGAC CGAAGGAGCT AACCGCTTTT TTGCACAACA TGGGGGATCA | 4250 |
| TGTAACTCGC CTTGATCGTT GGGAACCGGA GCTGAATGAA GCCATACCAA | 4300 |
| ACGACGAGCG TGACACCACG ATGCCAGCAG CAATGGCAAC AACGTTGCGC | 4350 |
| AAACTATTAA CTGGCGAACT ACTTACTCTA GCTTCCCGGC AACAATTAAT | 4400 |
| AGACTGGATG GAGGCGGATA AAGTTGCAGG ACCACTTCTG CGCTCGGCCC | 4450 |
| TTCCGGCTGG CTGGTTTATT GCTGATAAAT CTGGAGCCGG TGAGCGTGGG | 4500 |
| TCTCGCGGTA TCATTGCAGC ACTGGGGCCA GATGGTAAGC CCTCCCGTAT | 4550 |
| CGTAGTTATC TACACGACGG GGAGTCAGGC AACTATGGAT GAACGAAATA | 4600 |
| GACAGATCGC TGAGATAGGT GCCTCACTGA TTAAGCATTG GTAACTGTCA | 4650 |
| GACCAAGTTT ACTCATATAT ACTTTAGATT GATTTAAAAC TTCATTTTTA | 4700 |
| ATTTAAAAGG ATCTAGGTGA AGATCCTTTT TGATAATCTC ATGACCAAAA | 4750 |
| TCCCTTAACG TGAGTTTTCG TTCCACTGAG CGTCAGACCC CGTAGAAAAG | 4800 |
| ATCAAAGGAT CTTCTTGAGA TCCTTTTTTT CTGCGCGTAA TCTGCTGCTT | 4850 |
| GCAAACAAAA AAACCACCGC TACCAGCGGT GGTTTGTTTG CCGGATCAAG | 4900 |
| AGCTACCAAC TCTTTTTCCG AAGGTAACTG GCTTCAGCAG AGCGCAGATA | 4950 |
| CCAAATACTG TCCTTCTAGT GTAGCCGTAG TTAGGCCACC ACTTCAAGAA | 5000 |
| CTCTGTAGCA CCGCCTACAT ACCTCGCTCT GCTAATCCTG TTACCAGTGG | 5050 |
| CTGCTGCCAG TGGCGATAAG TCGTGTCTTA CCGGGTTGGA CTCAAGACGA | 5100 |
| TAGTTACCGG ATAAGGCGCA GCGGTCGGGC TGAACGGGGG GTTCGTGCAC | 5150 |
| ACAGCCCAGC TTGGAGCGAA CGACCTACAC CGAACTGAGA TACCTACAGC | 5200 |
| GTGAGCATTG AGAAAGCGCC ACGCTTCCCG AAGGGAGAAA GGCGGACAGG | 5250 |
| TATCCGGTAA GCGGCAGGGT CGGAACAGGA GAGCGCACGA GGGAGCTTCC | 5300 |
| AGGGGGAAAC GCCTGGTATC TTTATAGTCC TGTCGGGTTT CGCCACCTCT | 5350 |

```
GACTTGAGCG TCGATTTTTG TGATGCTCGT CAGGGGGGCG GAGCCTATGG         5400

AAAAACGCCA GCAACGCGGC CTTTTTACGG TTCCTGGCCT TTTGCTGGCC         5450

TTTTGCTCAC ATGTTCTTTC CTGCGTTATC CCCTGATTCT GTGGATAACC         5500

GTATTACCGC CTTTGAGTGA GCTGATACCG CTCGCCGCAG CCGAACGACC         5550

GAGCGCAGCG AGTCAGTGAG CGAGGAAGCG GAAGAGCGCC CAATACGCAA         5600

ACCGCCTCTC CCCGCGCGTT GGCCGATTCA TTAATCCAGC TGGCACGACA         5650

GGTTTCCCGA CTGGAAAGCG GGCAGTGAGC GCAACGCAAT TAATGTGAGT         5700

TACCTCACTC ATTAGGCACC CCAGGCTTTA CACTTTATGC TTCCGGCTCG         5750

TATGTTGTGT GGAATTGTGA GCGGATAACA ATTTCACACA GGAAACAGCT         5800

ATGACCATGA TTACGAATTA ATTCGAGCTC GCCCGACATT GATTATTGAC         5850

TAGTTATTAA TAGTAATCAA TTACGGGGTC ATTAGTTCAT AGCCCATATA         5900

TGGAGTTCCG CGTTACATAA CTTACGGTAA ATGGCCCGCC TGGCTGACCG         5950

CCCAACGACC CCCGCCCATT GACGTCAATA ATGACGTATG TTCCCATAGT         6000

AACGCCAATA GGGACTTTCC ATTGACGTCA ATGGGTGGAG TATTTACGGT         6050

AAACTGCCCA CTTGGCAGTA CATCAAGTGT ATCATATGCC AAGTACGCCC         6100

CCTATTGACG TCAATGACGG TAAATGGCCC GCCTGGCATT ATGCCCAGTA         6150

CATGACCTTA TGGGACTTTC CTACTTGGCA GTACATCTAC GTATTAGTCA         6200

TCGCTATTAC CATGGTGATG CGGTTTTGGC AGTACATCAA TGGGCGTGGA         6250

TAGCGGTTTG ACTCACGGGG ATTTCCAAGT CTCCACCCCA TTGACGTCAA         6300

TGGGAGTTTG TTTTGGCACC AAAATCAACG GGACTTTCCA AAATGTCGTA         6350

ACAACTCCGC CCCATTGACG CAAATGGGCG GTAGGCGTGT ACGGTGGGAG         6400

GTCTATATAA GCAGAGCTCG TTTAGTGAAC CGTCAGATCG CCTGGAGACG         6450

CCATCCACGC TGTTTTGACC TCCATAGAAG ACACCGGGAC CGATCCAGCC         6500

TCCGCGGCCG GGAACGGTGC ATTGGAACGC GGATTCCCCG TGCCAAGAGT         6550

GACGTAAGTA CCGCCTATAG AGTCTATAGG CCCACCCCCT TGGCTCGTTA         6600

GAACGCGGCT ACAATTAATA CATAACCTTA TGTATCATAC ACATACGATT         6650

TAGGTGACAC TATAGAATAA CATCCACTTT GCCTTTCTCT CCACAGGTGT         6700

CCACTCCCAG GTCCAACTGC AGGCCATGGC GGCCATCGAT T                 6741

(2) INFORMATION FOR SEQ ID NO:22:

(i) SEQUENCE CHARACTERISTICS:
        (A) LENGTH: 631 amino acids
        (B) TYPE: Amino Acid
        (D) TOPOLOGY: Linear (xi) SEQUENCE DESCRIPTION: SEQ ID NO:22:

Leu Lys Ser Pro Gln Lys Val Glu Val Asp Ile Ile Asp Asp Asn
 1               5                  10                  15

Phe Ile Leu Arg Trp Asn Arg Ser Asp Glu Ser Val Gly Asn Val
                20                  25                  30

Thr Phe Ser Phe Asp Tyr Gln Lys Thr Gly Met Asp Asn Trp Ile
                35                  40                  45

Lys Leu Ser Gly Cys Gln Asn Ile Thr Ser Thr Lys Cys Asn Phe
                50                  55                  60
```

-continued

```
Ser Ser Leu Lys Leu Asn Val Tyr Glu Glu Ile Lys Leu Arg Ile
                65                  70                  75

Arg Ala Glu Lys Glu Asn Thr Ser Ser Trp Tyr Glu Val Asp Ser
            80                  85                  90

Phe Thr Pro Phe Arg Lys Ala Gln Ile Gly Pro Pro Glu Val His
                95                  100                 105

Leu Glu Ala Glu Asp Lys Ala Ile Val Ile His Ile Ser Pro Gly
            110                 115                 120

Thr Lys Asp Ser Val Met Trp Ala Leu Asp Gly Leu Ser Phe Thr
                125                 130                 135

Tyr Ser Leu Leu Ile Trp Lys Asn Ser Ser Gly Val Glu Glu Arg
            140                 145                 150

Ile Glu Asn Ile Tyr Ser Arg His Lys Ile Tyr Lys Leu Ser Pro
                155                 160                 165

Glu Thr Thr Tyr Cys Leu Lys Val Lys Ala Ala Leu Leu Thr Ser
            170                 175                 180

Trp Lys Ile Gly Val Tyr Ser Pro Val His Cys Ile Lys Thr Thr
                185                 190                 195

Val Glu Asn Glu Leu Pro Pro Pro Glu Asn Ile Glu Val Ser Val
            200                 205                 210

Gln Asn Gln Asn Tyr Val Leu Lys Trp Asp Tyr Thr Tyr Ala Asn
                215                 220                 225

Met Thr Phe Gln Val Gln Trp Leu His Ala Phe Leu Lys Arg Asn
            230                 235                 240

Pro Gly Asn His Leu Tyr Lys Trp Lys Gln Ile Pro Asp Cys Glu
                245                 250                 255

Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn
                275                 280                 285

Thr Ser Phe Trp Ser Glu Glu Ile Lys Phe Asp Thr Glu Ile Gln
            290                 295                 300

Ala Phe Leu Leu Pro Pro Val Phe Asn Ile Arg Ser Leu Ser Asp
                305                 310                 315

Ser Phe His Ile Tyr Ile Gly Ala Pro Lys Gln Ser Gly Asn Thr
            320                 325                 330

Pro Val Ile Gln Asp Tyr Pro Leu Ile Tyr Glu Ile Ile Phe Trp
                335                 340                 345

Glu Asn Thr Ser Asn Ala Glu Arg Lys Ile Ile Glu Lys Lys Thr
            350                 355                 360

Asp Val Thr Val Pro Asn Leu Lys Pro Leu Thr Val Tyr Cys Val
                365                 370                 375

Lys Ala Arg Ala His Thr Met Asp Glu Lys Leu Asn Lys Ser Ser
            380                 385                 390

Val Phe Ser Asp Ala Val Cys Glu Lys Thr Lys Pro Gly Asn Asp
                395                 400                 405

Lys Thr His Thr Cys Pro Pro Cys Pro Ala Pro Glu Leu Leu Gly
            410                 415                 420

Gly Pro Ser Val Phe Leu Phe Pro Pro Lys Pro Lys Asp Thr Leu
                425                 430                 435

Met Ile Ser Arg Thr Pro Glu Val Thr Cys Val Val Val Asp Val
            440                 445                 450

Ser His Glu Asp Pro Glu Val Lys Phe Asn Trp Tyr Val Asp Gly
```

-continued

```
                    455                 460                 465
Val Glu Val His Asn Ala Lys Thr Lys Pro Arg Glu Gln Tyr
                470                 475                 480
Asn Ser Thr Tyr Arg Val Val Ser Val Leu Thr Val Leu His Gln
                485                 490                 495
Asp Trp Leu Asn Gly Lys Glu Tyr Lys Cys Lys Val Ser Asn Lys
                500                 505                 510
Ala Leu Pro Ala Pro Ile Glu Lys Thr Ile Ser Lys Ala Lys Gly
                515                 520                 525
Gln Pro Arg Glu Pro Gln Val Tyr Thr Leu Pro Pro Ser Arg Glu
                530                 535                 540
Glu Met Thr Lys Asn Gln Val Ser Leu Thr Cys Leu Val Lys Gly
                545                 550                 555
Phe Tyr Pro Ser Asp Ile Ala Val Glu Trp Glu Ser Asn Gly Gln
                560                 565                 570
Pro Glu Asn Asn Tyr Lys Thr Thr Pro Pro Val Leu Asp Ser Asp
                575                 580                 585
Gly Ser Phe Phe Leu Tyr Ser Lys Leu Thr Val Asp Lys Ser Arg
                590                 595                 600
Trp Gln Gln Gly Asn Val Phe Ser Cys Ser Val Met His Glu Ala
                605                 610                 615
Leu His Asn His Tyr Thr Gln Lys Ser Leu Ser Leu Ser Pro Gly
                620                 625                 630
Lys
631
```

MONOCLONAL ANTIBODIES TO TYPE I INTERFERON RECEPTOR

This is a continuation-in-part of non-provisional application U.S. Ser. No. 08/888,140 filed Jul. 3, 1997, now abandoned which claims priority under 35 U.S.C. §119(e) to provisional application U.S. Ser. No. 60/058,212 filed Jul. 16, 1996, which non-provisional application is incorporated herein by reference, and to which non-provisional application priority is claimed under 35 U.S.C. §120.

FIELD OF THE INVENTION

This invention relates to the field of anti-type I interferon receptor antibodies, and more particularly to anti-type I interferon receptor antibodies that neutralize the anti-viral cytopathic effects of various type I interferons.

BACKGROUND OF THE INVENTION

The type 1 interferons (IFNS) are cytokines that have pleiotropic effects on a wide variety of cell types. IFNs are best known for their anti-viral activity, but they also have anti-bacterial, anti-protozoal, immunomodulatory, and cell-growth regulatory functions. The type 1 interferons include interferon-α (IFN-α) and interferon-β (IFN-β). Human IFN-α (hIFN-α) is a heterogeneous family with at least 23 polypeptides while there is only one IFN-β polypeptide (*J. Interferon Res.*, 13: 443–444 (1993)). The hIFN-α subtypes show more than 70% amino acid sequence homology, and there is approximately 25% amino acid identity with hIFN-β. The hIFNs-α and hIFN-β share a common receptor.

Three components of the hIFN-α receptor complex have recently been cloned. The cDNA for the first hIFN-α receptor (hIFNAR1) encodes a 63 kD receptor protein (reported in Uze et al., *Cell*, 60: 225–234 (1990)). This receptor undergoes extensive glycosylation, which causes it to migrate in gel electrophoresis as a much larger 135 kD protein. The second interferon receptor, hIFNAR2 (hIFN-αβR long), is a 115 kD protein which mediates a functional signaling complex when associated with hIFNAR1 (reported in Domanski et al., *J. Biol. Chem.*, 270: 21606–21611 (1995)). The third hIFN-α receptor, an IFN-α/β receptor (hIFN-αβR short), is a 55 kD protein that can bind to type 1 hIFNs but cannot form a functional complex when associated with hIFNAR1 (reported in Novick et al., *Cell*, 77: 391–400 (1994)). This IFN-α/β receptor appears to be an alternatively spliced variant of hIFNAR2.

The unprocessed hIFNAR1 expression product is composed of 557 amino acids including an extracellular domain (ECD) of 409 residues, a transmembrane domain of 21 residues, and an intracellular domain of 100 residues as shown in FIG. 5 on page 229 of Uze et al., supra. The ECD of IFNAR1 is composed of two domains, domain 1 and domain 2, which are separated by a three-proline motif. There is 19% sequence identity and 50% sequence homology between domains 1 and 2 (Uze et al., supra). Each domain (D200) is composed of approximately 200 residues and can be further subdivided into two homologous subdomains (SD100) of approximately 100 amino acids.

Cytokine receptors have been categorized into two classes based on the distribution of cysteine residues. The class 1 cytokine receptor family includes receptors for human growth hormone (hGHR), erythropoietin, IL-3 and IL-4, while the class 2 cytokine receptor family includes the IFNγ receptor, tissue factor, CRF2-4 and IL-10 receptors. Sequence analysis of the hIFN-α receptors shows that they are related to the class 2 cytokine receptor family.

Through the use of IFNAR1 gene knockout mice, IFNAR1 has been shown to be essential for the response to all type 1 IFNs (Muller et al., *Science*, 264: 1918–1921 (1994); Cleary et al., *J. Biol. Chem.*, 269: 18747–18749 (1994)) and for the mediation of species-specific IFN signal transduction (Constantinescu et al., *Proc. Natl. Acad. Sci. USA*, 91: 9602–9606 (1994)).

Benoit et al., *J. Immunol.*, 150: 707–716 (1993) reported an anti-IFNAR1 mAb, 64G12, that was found to inhibit the binding of IFN-α2 (IFN-αA) and IFN-α8 (IFN-αB) to Daudi cells and to inhibit the antiviral activity of IFN-α2, IFN-β and IFN-ω (IFN-α$_{II}$1) on Daudi cells. Benoit et al. also reported that 64G12 recognizes an epitope present in domain 1 of IFNAR1. Eid and Tovey, *J. Interferon Cytokine Res.*, 15: 205–211 (1995) reported that 64G12 cannot immunoprecipitate cross-linked IFN-α2-receptor complexes from Daudi cells.

SUMMARY OF THE INVENTION

In one aspect, the invention provides an anti-IFNAR1 monoclonal antibody that inhibits the anti-viral activity of a first type I interferon and does not inhibit the anti-viral activity of a second type I interferon.

In another aspect, the invention provides an anti-IFNAR1 monoclonal antibody that inhibits anti-viral activity of a first type I interferon and does not inhibit the anti-viral activity of IFN-α2.

In still another aspect, the invention provides an anti-IFNAR1 monoclonal antibody that inhibits anti-viral activity of a first type I interferon and does not inhibit the anti-viral activity of IFN-α8.

In yet another aspect, the invention provides an anti-IFNAR1 monoclonal antibody that inhibits anti-viral activity of a first type I interferon and does not inhibit the anti-viral activity of IFN-α$_{II}$1.

In a further aspect, the invention provides an anti-IFNAR1 monoclonal antibody that inhibits anti-viral activity of a first type I interferon and does not inhibit the anti-viral activity of IFN-β.

In an additional aspect, the invention provides an anti-IFNAR1 monoclonal antibody that inhibits the anti-viral activity of a first type I interferon and does not inhibit the anti-viral activity of a second type I interferon selected from the group consisting of IFN-α2, IFN-α8, IFN-α$_{II}$1, and IFN-β.

The invention also encompasses an anti-IFNAR1 monoclonal antibody that binds to one or more amino acids in situ in the sequence of amino acids 244–249 of IFNAR1, and binds to one or more amino acids in situ in the sequence of amino acids 291–298 of IFNAR1.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A–E are graphs depicting epitope mapping for mAbs 2E1, 2E8, 2H6, 4A7 and 5A8, respectively, as determined by competitive binding ELISA. IFNAR1 (ECD)-IgG captured by goat anti-human IgG was incubated with predetermined concentrations of biotinylated (Bio)-mAb in the presence of 500–1,000 fold excess of unlabeled mAbs. The level of Bio-mAb bound was detected by the addition of horse radish peroxidase (HRP)-streptavidin.

FIG. 4 is a graph depicting a hydropathy profile and the location of certain alanine-substituted mutants of hIFNAR1.

FIG. 5 is a graph depicting mAb binding to IFNAR1 ECD-IgG (closed columns), IFNAR1 domain 1-IgG (shaded columns), IFNAR1 domain 2-IgG (diagonally hatched columns), and to a control with no antigen (open columns) as determined by ELISA. Microtiter wells coated with goat anti-human IgG were incubated with culture supernatants containing 2 mg/ml of each immunoadhesin followed by the addition of 10 mg/ml of mAbs. The mAb bound to the immunoadhesin was detected by HRP-goat anti-mouse IgG.

FIGS. 7A–7F (hereinafter collectively referred to as FIG. 7) depict the DNA sequence (SEQ ID NO. 21) and amino acid sequence (SEQ ID NO. 22) of the IFNAR1 ECD-IgG coding insert in pRK5 hIFNAR1-IgG clone 53.65. The DNA sequence encoding the leader peptide amino acid sequence (corresponding to amino acids 1–29 in FIG. 5 on page 229 of Uze et al., Cell, 60: 225–234 (1990)) of IFNAR1 is shown as bases 38–124 of SEQ ID NO. 21 in FIG. 7. The leader peptide amino acid sequence is omitted from FIG. 7 in order to present the mature IFNAR1 ECD sequence as amino acids 1–404 of the IFNAR1 ECD-IgG fusion protein sequence (SEQ ID NO. 22). Unless otherwise indicated, the amino acid numbering scheme for IFNAR1 ECD shown in FIG. 7 is used throughout the application.

METHODS OF CARRYING OUT THE INVENTION

A. Definitions

Figure 1:
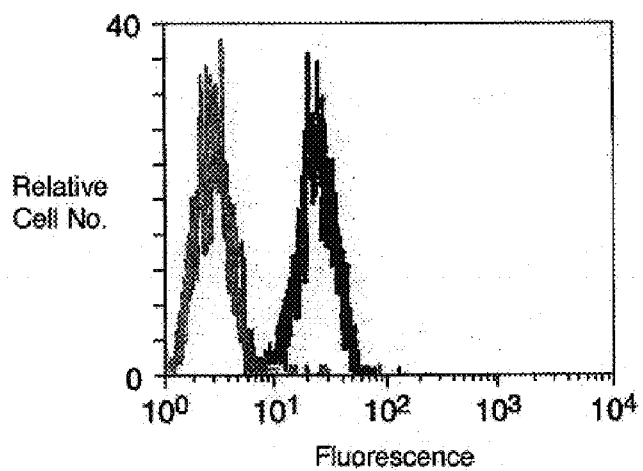
FIG. 1 is a graph depicting mAb 2E1 binding to U266 human myeloma cell line as determined by FACS analysis. U266 cells were incubated with hybridoma culture supernatant and then contacted with FITC-goat anti-mouse IgG.

As used herein, the terms "type I interferon" and "human type I interferon" are defined as all species of native human interferon which fall within the human interferon-α, interferon-ω and interferon-β classes and which bind to a common cellular receptor. Natural human interferon-α comprises 23 or more closely related proteins encoded by distinct genes with a high degree of structural homology (Weissmann and Weber, Prog. Nucl. Acid. Res. Mol. Biol., 33: 251 (1986); J. Interferon Res., 13: 443–444 (1993)). The human IFN-α locus comprises two subfamilies. The first subfamily consists of at least 14 functional, non-allelic genes, including genes encoding IFN-αA (IFN-α2), IFN-αB (IFN-α8), IFN-αC (IFN-α10), IFN-αD (IFN-α1), IFN-αE (IFN-α22), IFN-αF (IFN-α21), IFN-αG (IFN-α5), and IFN-αH (IFN-α14), and pseudogenes having at least 80% homology. The second subfamily, $α_{II}$ or ω, contains at least 5 pseudogenes and 1 functional gene (denoted herein as "IFN-$α_{II}$1" or "IFN-ω") which exhibits 70% homology with the IFN-α genes (Weissmann and Weber (1986)). The human IFN-β is encoded by a single copy gene.

As used herein, the terms "first human interferon-α (hIFN-α) receptor", "hIFNAR1", "IFNAR1", and "Uze chain" are defined as the 557 amino acid receptor protein cloned by Uze et al., Cell, 60: 225–234 (1990), including an extracellular domain of 409 residues, a transmembrane domain of 21 residues, and an intracellular domain of 100 residues, as shown in FIG. 5 on page 229 of Uze et al. Also encompassed by the foregoing terms are fragments of IFNAR1 that contain the extracellular domain (ECD) (or fragments of the ECD) of IFNAR1.

As used herein, the term "anti-IFNAR1 antibody" is defined as an antibody that is capable of binding to IFNAR1.

"Polymerase chain reaction" or "PCR" refers to a procedure or technique in which minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol. 51:263 (1987); Erlich, ed., PCR Technology (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment that contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be signed to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are well known.

The term "antibody" specifically covers monoclonal antibodies, including antibody fragment clones.

"Antibody fragments" comprise a portion of an intact antibody, generally the antigen binding or variable region of the intact antibody. Examples of antibody fragments include Fab, Fab', $F(ab')_2$, and Fv fragments; diabodies; single-chain antibody molecules, including single-chain Fv (scFv) molecules; and multispecific antibodies formed from antibody fragments.

The term "monoclonal antibody" as used herein refers to an antibody (or antibody fragment) obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816, 567). The "monoclonal antibodies" also include clones of antigen-recognition and binding-site containing antibody fragments (Fv clones) isolated from phage antibody libraries using the techniques described in Clackson et al., *Nature*, 352:624–628 (1991) and Marks et al., *J. Mol. Biol.*, 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in anti;bodies derived from another species or belonging to another antibody class or subclass, as well as fragments of such antibodies, so long as they exhibit the desired biological activity (U.S. Pat. No. 4,816,567 to Cabilly et al.; Morrison et al., *Proc. Natl. Acad. Sci. USA*, 81:6851–6855 (1984)).

"Humanized" forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues that are found neither in the recipient antibody nor in the imported CDR or framework sequences.

These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522–525 (1986); Reichmann et al., *Nature*, 332:323–329 (1988); and Presta, *Curr. Op. Struct. Biol.*, 2:593–596 (1992). The humanized antibody includes a Primatized™ antibody wherein the antigen-binding region of the antibody is derived from an antibody produced by immunizing macaque monkeys with the antigen of interest.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in *The Pharmacology of Monoclonal Antibodies*, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

As used herein, the terms "each member of the group consisting of" and "each of" are synonymous.

As used herein, the terms "any member of the group consisting of" and "any of" are synonymous.

B. General Methods

In general, the invention provides anti-IFNAR1 antibodies that are useful for treatment of immune-mediated disorders in which a partial or total blockade of type I interferon activity is desired. In one embodiment, the anti-IFNAR1 antibodies of the invention are used to treat autoimmune disorders, such as type I and type II diabetes, systemic lupus erythematosis (SLE), and rheumatoid arthritis. In another embodiment, the anti-IFNAR1 antibodies provided herein are used to treat graft rejection or graft versus host disease. The unique properties of the anti-IFNAR1 antibodies of the invention make them particularly useful for effecting target levels of immunosuppression in a patient. For patients requiring acute intervention, the anti-IFNAR1 antibodies provided herein which cause broad spectrum ablation of type I interferon activity can be used to effect the largest possible compromise of an undesired immune response. For patients requiring maintenance immunosuppression, the anti-IFNAR1 antibodies provided herein which block the activity of one or more (but not all) species of type I interferon can be used to effect partial compromise of the patient's immune system in order to reduce the risk of undesirable immune responses while leaving some components of the patient's type I interferon-mediated immunity intact in order to avoid infection.

In another aspect, the anti-IFNAR1 antibodies of the invention find utility as reagents for detection and isolation of IFNAR1, such as detection of IFNAR1 expression in various cell types and tissues, including the determination of IFNAR1 receptor density and distribution in cell populations, and cell sorting based on IFNAR1 expression. In yet another aspect, the present anti-IFNAR1 antibodies are useful for the development of IFNAR1 antagonists with type I interferon inhibition activity patterns similar to those of the subject antibodies. The anti-IFNAR1 antibodies of the invention can be used in competition binding assays with IFNAR1 to screen for small molecule antagonists of IFNAR1 that will exhibit similar pharmacological effects in blocking the activities of type I interferons to IFNAR1.

I. Methods of Making Synthetic Anti-IFNAR1 Fv Clones

The anti-IFNAR1 antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired ligand. Clones expressing Fv fragments capable of binding to the desired ligand are adsorbed to the ligand and thus separated from the non-binding clones in the library. The binding clones are then eluted from the ligand, and can be further enriched by additional cycles of ligand adsorption/elution. Any of the anti-IFNAR1 antibodies of the invention can be obtained by designing a suitable ligand screening procedure to select for the phage clone of interest followed by construction of a full length anti-IFNAR1 antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda MD (1991), vols. 1–3.

1. Construction of Phage Libraries

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433–455 (1994). As used herein, scFv encoding phage clones and Fab encoding phage clones are collectively referred to as "Fv phage clones" or "Fv clones".

The naive repertoire of an animal (the repertoire before antigen challenge) provides it with antibodies that can bind with moderate affinity ($K_a$ of about $10^6$ to $10^7$ $M^{-1}$) to essentially any non-self molecule. The sequence diversity of antibody binding sites is not encoded directly in the germline but is assembled in a combinatorial manner from V gene segments. In human heavy chains, the first two hypervariable loops (H1 and H2) are drawn from less than 50 VH gene segments, which are combined with D segments and JH segments to create the third hypervariable loop (H3). In human light chains, the first two hypervariable loops (L1 and L2) and much of the third (L3) are drawn from less than approximately 30 V$\lambda$ and less than approximately 30 V$\kappa$ segments to complete the third hypervariable loop (L3).

Each combinatorial rearrangement of V-gene segments in stem cells gives rise to a B cell that expresses a single VH-VL combination. Immunizations triggers any B cell making a VH-VL combination that binds the immunogen to proliferate (clonal expansion) and to secrete the corresponding antibody. These naive antibodies are then matured to high affinity ($Ka \geq 10^9$ $M^{-1}$) by a process of mutagenesis and selection known as affinity maturation. It is after this point that cells are normally removed to prepare hybridomas and generate high-affinity monoclonal antibodies.

At three stages of this process, repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433–455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725–734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381–388 (1992).

Phage display mimics the B cell. Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581–597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133–4137 (1991). When antibody fragments are fused to the N-terminus of pIII, the phage is infective. However, if the N-terminal domain of pIII is excised and fusions made to the second domain, the phage is not infective, and wild type pIII must be provided by helper phage.

The pIII fusion and other proteins of the phage can be encoded entirely within the same phage replicon, or on different replicons. When two replicons are used, the pIII fusion is encoded on a phagemid, a plasmid containing a phage origin of replication. Phagemids can be packaged into phage particles by "rescue" with a helper phage such as M13KO7 that provides all the phage proteins, including pIII, but due to a defective origin is itself poorly packaged in competitions with the phagemids as described in Vieira and Messing, *Meth. Enzymol.*, 153: 3–11 (1987). In a preferred method, the phage display system is designed such that the recombinant phage can be grown in host cells under conditions permitting no more than a minor amount of phage particles to display more than one copy of the Fv-coat protein fusion on the surface of the particle as described in Bass et al., *Proteins*, 8: 309–314 (1990) and in WO 92/09690 (PCT/US91/09133 published Jun. 11, 1992).

In general, nucleic acids encoding antibody gene fragments are obtained from immune cells harvested from humans or animals. If a library biased in favor of anti-IFNAR1 clones is desired, the subject is immunized with IFNAR1 to generate an antibody response, and spleen cells and/or circulating B cells other peripheral blood lymphocytes (PBLs) are recovered for library construction. In a preferred embodiment, a human antibody gene fragment library biased in favor of anti-human IFNAR1 clones is obtained by generating an anti-human IFNAR1 antibody response in transgenic mice carrying a functional human immunoglobulin gene array (and lacking a functional endogenous antibody production system) such that IFNAR1 immunization gives rise to B cells producing human antibodies against IFNAR1. The generation of human antibody-producing transgenic mice is described in Section B(III)(b) below.

Additional enrichment for anti-IFNAR1 reactive cell populations can be obtained by using a suitable screening procedure to isolate B cells expressing IFNAR1-specific membrane bound antibody, e.g., by cell separation with IFNAR1 affinity chromatography or adsorption of cells to fluorochrome-labelled IFNAR1 followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which IFNAR1 is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3'ends of rearranged VH and VL genes as described in Orlandi et al., *Proc. Natl. Acad. Sci*. (*USA*), 86: 3833–3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544–546

(1989). However, for amplifying from cDNA, back primers can also be based in the leader exon as described in Jones et al., *Biotechnol.*, 9: 88–89 (1991), and forward primers within the constant region as described in Sastry et al., *Proc. Natl. Acad. Sci. (USA)*, 86: 5728–5732 (1989). To maximize complementarity, degeneracy can be incorporated in the primers as described in Orlandi et al. (1989) or Sastry et al. (1989). Preferably, the library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581–597 (1991) or as described in the method of Orum et al., *Nucleic Acids Res.*, 21: 4491–4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624–628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776–798 (1992)), and mapped (reported in Matsuda et al., *Nature Genet.*, 3: 88–94 (1993); these cloned segments (including all the major conformations of the H1 and H2 loop) can be used to generate diverse VH gene repertoires with PCR primers encoding H3 loops of diverse sequence and length as described in Hooge, boom and Winter, *J. Mol. Biol.*, 227: 381–388 (1992). VH repertoires can also be made with ail the sequence diversity focussed in a long H3 loop of a single length as described in Barbas et al., *Proc. Natl. Acad. Sci. USA*, 89: 4457–4461 (1992). Human Vκ and Vλ segments have been cloned and sequenced (reported in Williams and Winter, *Eur. J. Immunol.*, 23: 1456–1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381–388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119–126 (1993), or in vivo by combinatorial infection, e.g., the loxP system described in Waterhouse et al., *Nucl. Acids Res.*, 21: 2265–2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_a$ of about $10^8$).

Alternatively, the repertoires may be cloned sequentially into the same vector, e.g. as described in Barbas et al., *Proc. Natl. Acad Sci. USA*, 88: 7978–7982 (1991), or assembled together by PCR and then cloned, e.g. as described in Clackson et al., *Nature*, 352: 624–628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831–3837 (1992).

The antibodies produced by naive libraries (either natural or synthetic) can be of moderate affinity ($K_a$ of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique*, 1: 11–15 (1989)) in the method of Hawkins et al., *J. Mol. Biol.*, 226: 889–896 (1992) or in the method of Gram et al., *Proc. Natl. Acad. Sci USA*, 89: 3576–3580 (1992). Additionally, affinity maturation can be performed by randomly mutating one or more CDRs, e.g. using PCR with primers carrying random sequence spanning the CDR of interest, in selected individual Fv clones and screening for higher affinity clones. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779–783 (1992). This technique allows the production of antibodies and antibody fragments with affinities in the $10^{-9}$ M range.

2. Panning Phage Display Libraries for Anti-IFNAR1 Clones a. Synthesis of IFNAR1 and IFNAR1 Ligands Nucleic acid sequence encoding the IFNAR1s used herein can be designed using the amino acid sequence of the desired region of IFNAR1, e.g. the extracellular domain spanning amino acids 28 to 434 of FIG. 2 of WO 93/20187 (PCT/EP93/00770 published Oct. 14, 1993). Alternatively, the cDNA sequence of FIG. 2 of WO 93/20187 can be used. In addition, nucleic acid encoding an immunoglobulin G (IgG)-IFNAR1 extracellular domain fusion protein can be obtained from the amino acid or cDNA sequence shown in FIG. 8 below. Likewise, nucleic acid sequence encoding the human type i interferons used herein can be designed using published amino acid and nucleic acid sequences, e.g. see the *J. Interferon Res.*, 13: 443–444 (1993) compilation of references containing genomic and cDNA sequences for various type I interferons, and the references cited therein. For the IFN-α2, IFNα8, IFN-α10, IFN-α1, IFN-α22, IFN-α21, IFN-α5, and IFN-α14 amino acid sequences or cDNA sequences, see FIGS. 3 and 4 on pages 23–24 of Goeddel et al., *Nature*, 290: 20–26 (198 1). For cDNA encoding the amino acid sequence of IFN-$\alpha_{II}1$ (IFN-ω)), see Capon et al., *Mol. Cell. Biol.*, 5: 768–779 (1985) and Hauptmann and Swetly, *Nucleic Acids Res.*, 13: 4739–4749 (1985). For cDNA encoding the amino acid sequence of IFN-β, see Taniguchi et al., *Proc. Jpn. Acad Ser. B*, 55: 464–469 (1979); Taniguchi et al., *Gene*, 10: 11–15 (1980); and U.S. Pat. No. 5,460,811 to Goeddel and Crea. DNAs encoding the IFNAR1s or type I interferons of interest can be prepared by a variety of methods known in the art. These methods include, but are not limited to, chemical synthesis by any of the methods described in Engels et al., *Agnew. Chem. Int. Ed. Engl.*, 28: 716–734 (1989), such as the triester, phosphite, phosphoramidite and H-phosphonate methods. In one embodiment, codons preferred by the expression host cell are used in the design of the IFNAR1 or type I interferon-encoding DNA. Alternatively, DNA encoding the IFNAR1 or type I interferon can be isolated from a genomic or cDNA library.

For production of the mutant IFNAR1s used herein, DNA sequence encoding wild type IFNAR1 can be altered to encode the desired IFNAR1 mutant by using recombinant DNA techniques, such as site specific mutagenesis (Kunkel et al., *Methods Enzymol.* 204:125–139 (1991); Carter, P., et al., *Nucl. Acids. Res.* 13:4331 (1986); Zoller, M. J. et al., *Nucl. Acids Res.* 10:6487 (1982)), cassette mutagenesis (Wells, J. A., et al., *Gene* 34:315 (1985)), restriction selection mutagenesis (Wells, J. A., et al., *Philos. Trans, R. Soc. London SerA* 317: 415 (1986)), and the like.

Following construction of the DNA molecule encoding the IFNAR1 or type I interferon of interest, the DNA molecule is operably linked to an expression control sequence in an expression vector, such as a plasmid, wherein the control sequence is recognized by a host cell transformed with the vector. In general, plasmid vectors contain replication and control sequences that are derived from species compatible with the host cell. The vector ordinarily carries a replication site, as well as sequences which encode proteins that are capable of providing phenotypic selection in transformed cells.

For expression in prokaryotic hosts, suitable vectors include pBR322 (ATCC No. 37,017), phGH107 (ATCC No. 40,011), pBO475, pS0132, pRIT5, any vector in the pRIT20 or pRIT30 series (Nilsson and Abrahmsen, *Meth. Enzymol.*, 185: 144–161 (1990)), pRIT2T, pKK233-2, pDR540 and pPL-lambda. Prokaryotic host cells containing the expression vectors suitable for use herein include *E. coli* K12 strain 294 (ATCC NO. 31446), *E coli* strain JM101 (Messing et al., *Nucl. Acid Res.*, 9: 309 (1981)), *E. coli* strain B, *E. coli* strain $\chi$776 (ATCC No. 31537), *E. coli* c600 (Appleyard, *Genetics*, 39: 440 (1954)), *E. coli* W3110 (F-, gamma-, prototrophic, ATCC No. 27325), *E. coli* strain 27C7 (W3110, tonA, phoA E15, (argF-lac)169, ptr3, degP41, ompT, kan') (U.S. Pat. No. 5,288,931, ATCC No. 55,244), *Bacillus subtilis, Salmonella typhimurium, Serratia marcesans*, and Pseudomonas species.

In addition to prokaryotes, eukaryotic organisms, such as yeasts, or cells derived from multicellular organisms can be used as host cells. For expression in yeast host cells, such as common baker's yeast or *Saccharomyces cerevisiae*, suitable vectors include episomally replicating vectors based on the 2-micron plasmid, integration vectors, and yeast artificial chromosome (YAC) vectors. For expression in insect host cells, such as Sf9 cells, suitable vectors include baculoviral vectors. For expression in plant host cells, particularly dicotyledonous plant hosts, such as tobacco, suitable expression vectors include vectors derived from the Ti plasmid of *Agrobacterium tumefaciens.*

However, interest has been greatest in vertebrate host cells. Examples of useful mammalian host cells include monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59 (1977)); baby hamster kidney cells (BHK, ATCC CCL 10); Chinese hamster ovary cells/-DHFR (CHO, Urlaub and Chasin, *Proc. Natl. Acad. Sci. USA*, 77: 4216 (1980)); mouse sertoli cells (TM4, Mather, *Biol. Reprod.*, 23: 243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL5 1); TRI cells (Mather et al., *Annals N.Y. Acad Sci.*, 383: 44–68 (1982)); MRC 5 cells; FS4 cells; and a human hepatoma cell line (Hep G2). For expression in mammalian host cells, useful vectors include vectors derived from SV40, vectors derived from cytomegalovirus such as the pRK vectors, including pRK5 and pRK7 (Suva et al., *Science*, 237: 893–896 (1987), EP 307,247 (Mar. 15, 1989), EP 278,776 (Aug. 17, 1988)) vectors derived from vaccinia viruses or other pox viruses, and retroviral vectors such as vectors derived from Moloney's murine leukemia virus (MoMLV).

Optionally, the DNA encoding the IFNAR1 or type I interferon of interest is operably linked to a secretory leader sequence resulting in secretion of the expression product by the host cell into the culture medium. Examples of secretory leader sequences include stII, ecotin, lamB, herpes GD, lpp, alkaline phosphatase, invertase, and alpha factor. Also suitable for use herein is the 36 amino acid leader sequence of protein A (Abrahmsen et al., *EMBO J.*, 4: 3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning* (2nd ed.), Cold Spring Harbor Laboratory, NY (1989), is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published 29 June 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad Sci.* (*USA*), 76: 3829 (1979). However, other methods for introducing DNA into cells such as by nuclear injection, electroporation, or by protoplast fusion may also be used.

Prokaryotic host cells used to produce the IFNAR1 or type I interferon of interest can be cultured as described generally in Sambrook et al., supra.

The mammalian host cells used to produce the IFNAR1 or type I interferon of interest can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace, *Meth. Enz.*, 58: 44 (1979), Barnes and Sato,

*Anal. Biochem.*, 102: 255 (1980), U.S. Pat. Nos. 4,767,704; 4,657,866; 4,927,762; or 4,560,655; WO 90/03430; WO 87/00195; U.S. Pat. No. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

In an intracellular expression system or periplasmic space secretion system, the recombinantly expressed IFNAR1 or type I interferon protein can be recovered from the culture cells by disrupting the host cell membrane/cell wall (e.g. by osmotic shock or solubilizing the host cell membrane in detergent). Alternatively, in an extracellular secretion system, the recombinant protein can be recovered from the culture medium. As a first step, the culture medium or lysate is centrifuged to remove any particulate cell debris. The membrane and soluble protein fractions are then separated. Usually, the IFNAR1 or type I interferon is purified from the soluble protein fraction. If the IFNAR1 is expressed as a membrane bound species, the membrane bound peptide can be recovered from the membrane fraction by solubilization with detergents. The crude peptide extract can then be further purified by suitable procedures such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins and ligand affinity using IFNAR1 (for type I interferon purification) or type I interferons or anti-IFNAR1 antibodies (for IFNAR1 purification) immobilized on a matrix.

Many of the human type I interferons used herein can be obtained from commercial sources, e.g. human IFN-β is available from Sigma (St. Louis, Mo.).

b. Immobilization of IFNAR1

The purified IFNAR1 can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Attachment of the IFNAR1 protein to the matrix can be accomplished by the methods described in *Methods in Enzymology*, vol. 44 (1976). A commonly employed technique for attaching protein ligands to polysaccharide matrices, e.g. agarose, dextran or cellulose, involves activation of the carrier with cyanogen halides and subsequent coupling of the peptide ligand's primary aliphatic or aromatic amines to the activated matrix.

Alternatively, IFNAR1 can be used to coat the wells of adsorption plates, expressed on host cells affixed to adsorption plates or used in cell sorting, or conjugated to biotin for capture with streptavidin-coated beads, or used in any other art-known method for panning phage display libraries.

c. Panning Procedures

The phage library samples are contacted with immobilized IFNAR1 under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad Sci USA*, 88: 7978–7982 (1991), or by alkali, e.g. as described in Marks et al., *J. Mol. Biol.*, 222: 581–597 (1991), or by IFNAR1 antigen or type I interferon ligand competition, e.g. in a procedure similar to the antigen competition method of Clackson et al., *Nature*, 352: 624–628 (1991). Phages can be enriched 20–1000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but also favors rebinding of phage that has dissociated. The selection of antibodies with slow dissociation kinetics (and good binding affinities) can be promoted by use of long washes and monovalent phage display as described in Bass et al., *Proteins*, 8: 309–314 (1990) and in WO 92/09690, and a low coating density of antigen as described in Marks et al., *Biotechnol.*, 10: 779–783 (1992).

It is possible to select between phage antibodies of different affinities, even with affinities that differ slightly, for IFNAR1. However, random mutation of a selected antibody (e.g. as performed in some of the affinity maturation techniques described above) is likely to give rise to many mutants, most binding to antigen, and a few with higher affinity. With limiting IFNAR1, rare high affinity phage could be competed out. To retain all the higher affinity mutants, phages can be incubated with excess biotinylated IFNAR1, but with the biotinylated IFNAR1 at a concentration of lower molarity than the target molar affinity constant for IFNAR1. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

3. Activity Selection of Anti-IFNAR1 Clones

In one embodiment, the invention provides anti-IFNAR1 antibodies which bind to specific determinant(s) on IFNAR1 and/or which do not bind other specific determinant(s) on IFNAR1. Fv clones corresponding to such anti-IFNAR1 antibodies can be conveniently selected by adsorbing library clones to immobilized IFNAR1 mutants containing Ala substitutions at the specific determinants of interest. If clones which do not bind the selected IFNAR1 determinant (s) are desired, then the clones which adsorb to the IFNAR1 mutant are recovered, e.g. by eluting the adsorbed clones with wild type IFNAR1. The separation occurs because of the difference in the affinities of the desired and undesired clones for the IFNAR1 mutant. Since the IFNAR1 determinant(s) bound by the desired clones do not include the amino acid(s) at the Ala-substituted position(s) in the IFNAR1 mutant, the desired clones will bind to the immobilized, mutant IFNAR1 whereas the undesired clones will not. Accordingly, the adsorption of library clones to immobilized, mutant IFNAR1 will yield a population of clones bound to solid phase that is enriched for the property of not being able to bind to the selected IFNAR1 determinant(s). The desired clones will exhibit similar or approximately the same binding activities with the corresponding Ala-substituted IFNAR1 mutant and wild type IFNAR1.

If clones which bind to the selected IFNAR1 determinant(s) are desired, then library clones which fail to adsorb to immobilized, mutant IFNAR1 are recovered (i.e. collected from the column flow-through fractions), the recovered clones are adsorbed to immobilized, wild type IFNAR1, and then the adsorbed clones are recovered, e.g. by elution with excess wild type IFNAR1. The first adsorption step removes clones that bind to IFNAR1 but do not bind to the selected determinant(s), and the second adsorption step removes clones that do not bind to IFNAR1 at all, leaving a population of clones enriched for binding to the selected IFNAR1 determinant(s). The desired clone will exhibit binding activity with wild type IFNAR1 that is greater than the clone's binding activity with the corresponding Ala-substituted IFNAR1 mutant (i.e. a binding level with wild type IFNAR1 that is above the background binding level with mutant IFNAR1). Optionally, the desired clone will exhibit binding activity with the corresponding Ala-substituted IFNAR1 mutant that is less than about 50%, or less than about 30%, or less than about 20%, or less than about 10%, or less than about 7%, or less than about 6%, or less than about 5%, or less than about 4%, or less than about 3%, or less than about 2%, or less than about 1%, or about 0% of the clone's binding activity with wild type IFNAR1.

Optionally, clones that bind or do not bind to selected IFNAR1 determinants can be further enriched by repeating the selection procedures described herein one or more times.

Also provided herein are anti-IFNAR1 antibodies and Fv clones which bind to one or more amino acids in situ in the sequence of amino acids 103–111 of IFNAR1 and which do not bind to one or more amino acids in situ in the sequence of amino acids 244–249 of IFNAR1. These Fv clones can be selected by (1) isolating anti-IFNAR1 clones from a phage library as described in Section B(I)(2) above, and optionally amplifying the isolated population of phage clones by growing up the population in a suitable bacterial host; (2) adsorbing the anti-IFNAR1 phage clones to immobilized mutant IFNAR1 containing Ala substitutions at amino acid positions 244–249 in order to separate desired clones from clones that require wild type amino acids at positions 244–249 for binding to IFNAR1; (3) eluting the adsorbed clones with an excess of IFNAR1; (4) contacting the eluted clones with immobilized, mutant IFNAR1 containing Ala substitutions at amino acid positions 103–111 in order to adsorb undesired clones which bind to determinants on IFNAR1 that do not overlap with amino acid positions 103–111; and (5) recovering the clones which fail to adsorb to the immobilized, mutant IFNAR1 from the flow-through fractions in step (4).

Additionally provided herein are anti-IFNAR1 antibodies and Fv clones which bind to one or more amino acids in situ in the sequence of amino acids 103–111 of IFNAR1 and which do not bind to amino acid 249 of IFNAR1 in situ.

These Fv clones can be selected by (1) isolating anti-IFNAR1 clones from a phage library as described in Section B(I)(2) above, and optionally amplifying the isolated population of phage clones by growing up the population in a suitable bacterial host; (2) adsorbing anti-IFNAR1 phage clones to immobilized mutant IFNAR1 containing an Ala substitution at amino acid position 249 in order to separate desired clones from clones that require the wild type amino acid at position 249 for binding to IFNAR1; (3) eluting the adsorbed clones with an excess of IFNAR1; (4) contacting the eluted clones with immobilized, mutant IFNAR1 containing Ala substitutions at amino acid positions 103–111 in order to adsorb undesired clones which bind to determinants on IFNAR1 that do not overlap with amino acid positions 103–111; and (5) recovering the clones which fail to adsorb to the immobilized, mutant IFNAR1 from the flow-through fractions in step (4).

Also encompassed herein are anti-IFNAR1 antibodies and Fv clones which bind to one or more amino acids in situ in the sequence of amino acids 103–111 of IFNAR1, and which bind to amino acids 291 and 296 of IFNAR1 in situ, and which do not bind to amino acid 249 of IFNAR1 in situ. These Fv clones can be selected by (1) isolating anti-IFNAR1 clones from a phage library as described in Section B(I)(2) above, and optionally amplifying the isolated population of phage clones by growing up the population in a suitable bacterial host; (2) adsorbing anti-IFNAR1 phage clones to immobilized mutant IFNAR1 containing an Ala substitution at amino acid position 249 in order to separate desired clones from clones that require the wild type amino acid at position 249 for binding to IFNAR1; (3) eluting the adsorbed clones with excess IFNAR1; (4) contacting the eluted clones with immobilized, mutant IFNAR1 containing Ala substitutions at amino acid positions 103–111 in order to adsorb undesired clones which bind to determinants on IFNAR1 that do not overlap with amino acid positions 103–111; (5) recovering the clones that fail to adsorb to immobilized, mutant IFNAR1 from the flow-through fractions in step (4); (6) contacting the recovered clones with immobilized, mutant IFNAR1 containing Ala substitutions at amino acids 291 and 296 in order to adsorb undesired clones which bind to determinants on IFNAR1 that do not overlap with amino acid positions 291 and 296; and (7) recovering the clones which fail to adsorb to immobilized, mutant IFNAR1 from the flow-through fractions in step (6).

Also provided herein are anti-IFNAR1 antibodies and Fv clones that bind to one or more amino acids in situ in the sequence of amino acids 244–249 of IFNAR1. These Fv clones can be selected by (1) isolating anti-IFNAR1 clones from a phage library as described in Section B(I)(2) above, and optionally amplifying the isolated population of phage clones by growing up the population in a suitable bacterial host; (2) adsorbing the anti-IFNAR1 clones to immobilized IFNAR1; (3) subjecting the adsorbed clones to elution with a mutant IFNAR1 containing Ala substitutions at amino acid positions 244–249 in order to elute the undesired clones which bind determinants on IFNAR1 that do not overlap with amino acids at positions 244–249 on IFNAR1; and (4) recovering the remaining adsorbed clones by elution with excess IFNAR1.

Additionally provided herein are anti-IFNAR1 antibodies and Fv clones that bind to one or more amino acids in situ in the sequence of amino acids 291–298 of IFNAR1. These Fv clones can be selected by (1) isolating anti-IFNAR1 clones from a phage library as described in Section B(1)(2) above, and optionally amplifying the isolated population of phage clones by growing up the population in a suitable bacterial host; (1) adsorbing the anti-IFNAR1 clones to immobilized IFNAR1; (3) subjecting the adsorbed clones to elution with a mutant IFNAR1 containing Ala substitutions at amino acid positions 291–298 in order to elute undesired clones which bind determinants on IFNAR1 that do not overlap with amino acid positions 291–298 on IFNAR1; and (4) recovering the remaining adsorbed clones by elution with excess IFNAR1.

The invention also provides anti-IFNAR1 antibodies and Fv clones which bind to one or more amino acids in situ in the sequence of amino acids 244–249 of IFNAR1 and bind to one or more amino acids in situ in the sequence of amino acids 291–298 of IFNAR1. Fv clones corresponding to such anti-IFNAR1 antibodies can be selected by (:) isolating anti-IFNAR1 clones from a phage library as described in Section B(I)(2) above, and optionally amplifying the isolated population of phage clones by growing up the population in a suitable bacterial host; (2) adsorbing the resulting clones to immobilized IFNAR1; (3) subjecting the adsorbed anti-IFNAR1 clones to elution with a cocktail of excess mutant IFNAR1 containing Ala substitutions at amino acids positions 244–249 and excess mutant IFNAR1 containing Ala substitutions at amino acid positions 291–298, or subjecting the adsorbed clones to consecutive elutions with each of the IFNAR1 mutants, in order to elute undesired clones which bind to determinants on IFNAR1 that do not overlap with both amino acid positions 244–249 and amino acid positions 291–298 on IFNAR1; and (4) recovering the remaining adsorbed clones by elution with excess IFNAR1.

In another embodiment, the invention provides anti-IFNAR1 antibodies and Fv clones that bind to amino acid 249 of IFNAR1. Fv clones corresponding to such anti-IFNAR1 antibodies can be selected by (1) isolating anti-IFNAR1 clones from a phage library as described in Section B(I)(2) above, and optionally amplifying the isolated population of phage clones by growing up the anti-IFNAR1 population in a suitable bacterial host; (2) adsorbing the resulting anti-IFNAR1 clones to immobilized IFNAR1; (3) subjecting the adsorbed clones to elution with mutant IFNAR1 containing an Ala substitution at amino acid position 249 of IFNAR1 in order to elute undesired clones which bind determinants on IFNAR1 that do not overlap with amino acid position 249 on IFNAR1; and (4) recovering the remaining adsorbed clones by elution with excess IFNAR1.

In another embodiment, the invention provides anti-IFNAR1 antibodies and Fv clones that bind to amino acid 291 of IFNAR1I. Fv clones corresponding to such anti-IFNAR1 antibodies can be selected by (1) isolating anti-IFNAR1 clones from a phage library as described in Section B(I)(2) above, and optionally amplifying the isolated population of phage clones by growing up the anti-IFNAR1 population in a suitable bacterial host; (2) adsorbing the resulting anti-IFNAR1 clones to immobilized IFNAR1; (3) subjecting the adsorbed clones to elution with mutant IFNAR1 containing an Ala substitution at amino acid position 291 of IFNAR1 in order to elute undesired clones which bind determinants on IFNAR1 that do not overlap with amino acid position 291 on IFNAR1; and (4) recovering the remaining adsorbed clones by elution with excess IFNAR1.

In another embodiment, the invention provides anti-IFNAR1 antibodies and Fv clones that bind to amino acid 296 of IFNAR1. Fv clones corresponding to such anti-IFNAR1 antibodies can be selected by (1) isolating anti-IFNAR1 clones from a phage library as described in Section B(I)(2) above, and optionally amplifying the isolated population of phage clones by growing up the anti-IFNAR1 population in a suitable bacterial host; (2) adsorbing the resulting anti-IFNAR1 clones to immobilized IFNAR1; (3) subjecting the adsorbed clones to elution with mutant IFNAR1 containing an Ala substitution at amino acid, position 296 of IFNAR1 in order to elute undesired clones which bind determinants on IFNAR1 that do not overlap with amino acid position 296 on IFNAR1; and (4) recovering the remaining adsorbed clones by elution with excess IFNAR1.

The invention further provides anti-IFNAR1 antibodies and Fv clones that bind to amino acids 249, 291 and 296 of IFNAR1 in situ. Fv clones corresponding to such anti-IFNAR1 antibodies can be selected by (1) isolating anti-IFNAR1 clones from a phage library as described in Section B(I)(2) above, and optionally amplifying the isolated population of phage clones by growing up the population in a suitable bacterial host; (2) adsorbing the resulting anti-IFNAR1 clones to immobilized IFNAR1; (3) subjecting the adsorbed clones to elution with a cocktail of excess mutant IFNAR1 containing an Ala substitution at amino acid position 249, excess mutant IFNAR1 containing an Ala substitution at amino acid position 291, and excess mutant IFNAR1 containing an Ala substitution at amino acid position 296, or subjecting the adsorbed clones to consecutive elutions with each of the IFNAR1 mutants, in order to elute undesired clones which bind to determinants on IFNAR1 which do not overlap with amino acids 249, 291 or 296 of IFNAR1 in situ; and (4) recovering the remaining adsorbed clones by elution with excess IFNAR1.

In another embodiment, the invention provides any of the anti-IFNAR1 antibodies described above that additionally binds to a conformational epitope on IFNAR1. Fv clones corresponding to such anti-IFNAR1 antibodies can be selected according to the procedures described above modified to include the additional step of screening clones for binding to denatured IFNAR1, e.g., by layering clone suspensions on plates coated with denatured IFNAR1, and collecting non-binding clones from the plate washes. It will be appreciated that the denatured IFNAR1-coated plate adsorption step can be performed before or after the other selection procedures for the Fv clone of interest, or can be performed at any point in such selection procedures that is immediately preceded by the elution of the clones of interest from a particular adsorbent.

Also provided herein are anti-IFNAR1 Fv clones that bind to the amino acid sequence of amino acids 103–111 of IFNAR1 in situ, do not bind to the amino acid sequence of amino acids 244–249 of IFNAR1 in situ, and bind to a conformational epitope of IFNAR1.

Additionally provided herein are anti-IFNAR1 Fv clones that bind to the amino acid sequence of amino acids 103–111 of IFNAR1 in situ, do not bind to amino acid 249 of IFNAR1 in situ, and bind to a conformational epitope of IFNAR1.

Further encompassed herein are anti-IFNAR1 Fv clones that bind to the amino acid sequence of amino acids 103–111 of IFNAR1 in situ, bind to amino acids 291 and 296 of IFNAR1 in situ, do not bind to amino acid 249 of IFNAR1 in situ, and bind to a conformational epitope of IFNAR1.

Also included herein are any of the anti-IFN antibodies described above that additionally bind to a conformational epitope formed by domain 1 and domain 2 of IFNAR1. Fv clones corresponding to such anti-IFNAR1 antibodies can be selected according to the procedures described above modified to include selection steps that exclude clones that bind to a peptide consisting of the amino acid sequence of domain 1 (amino acids 1–200 of IFNAR1) or bind to a peptide consisting of the amino acid sequence of domain 2

(amino acids 204–404). In one embodiment, the clones of interest are selected by layering a clone suspension on plates coated with domain 1 peptide, recovering the non-binding clones from the plate washes, layering a suspension of the recovered clones on plates coated with domain 2 peptide, and recovering the non-binding clones. In another embodiment, the clones of interest are selected by adsorbing clones to immobilized IFNAR1, subjecting the adsorbed clones to elution with a cocktail of excess domain 1 peptide and excess domain 2 peptide (or alternatively subjecting the adsorbed clones to serial elutions with the individual peptides), discarding the eluted clones, and recovering the clones that remain bound to adsorbent. The domain 1 peptide and domain 2 peptide binding selection step can be performed before or after the other selection procedures for the Fv clone of interest, or can be performed at any point in such selection procedures immediately preceding which the clones of interest are either (1) eluted from a particular adsorbent (e.g. if peptide-coated plates are used for selection) or (2) adsorbed to immobilized IFNAR1 (e.g. if elution with a peptide cocktail is used for selection).

Also provided herein are anti-IFNAR1 Fv clones that bind to the amino acid sequence of amino acids 103–111 of IFNAR1 in situ, do not bind to the amino acid sequence of amino acids 244–249 of IFNAR1 in situ, do not bind to a peptide consisting of the amino acid sequence of domain 1 (amino acids 1–200 of IFNAR1), and do not bind to a peptide consisting of the amino acid sequence of domain 2 (amino acids 204–404 of IFNAR1).

Additionally provided herein are anti-IFNAR1 Fv clones that bind to the amino acid sequence of amino acids 103–111 of IFNAR1 in situ, do not bind to amino acid 249 of IFNAR1 in situ, do not bind to a peptide consisting of the amino acid sequence of domain 1 (amino acids 1–200 of IFNAR1), and do not bind to a peptide consisting of the amino acid sequence of domain 2 (amino acids 204–404 of IFNAR1).

Further encompassed herein are anti-IFNAR1 Fv clones that bind to the amino acid sequence of amino acids 103–111 of IFNAR1 in situ, bind to amino acids 291 and 296 of IFNAR1 in situ, do not bind to amino acid 249 of IFNAR1 in situ, do not bind to a peptide consisting of the amino acid sequence of domain 1 (amino acids 1–200 of IFNAR1), and do not bind to a peptide consisting of the amino acid sequence of domain 2 (amino acids 204–404 of IFNAR1).

In yet another embodiment, the invention provides anti-IFNAR1 Fv clones that bind to one or more of amino acids 244–249 of IFNAR1 in situ, bind to one or more of amino acids 291–298 of IFNAR1 in situ, and bind to a conformational epitope of IFNAR1.

In still another embodiment, the invention provides anti-IFNAR1 Fv clones that bind to amino acids 249, 291 and 296 of IFNAR1 in situ, and bind to a conformational epitope of IFNAR1.

Further provided herein are anti-IFNAR1 Fv clones that bind to one or more of amino acids 244–249 of IFNAR1 in situ, bind to one or more of amino acids 291–298 of IFNAR1 in situ, do not bind to a peptide consisting of the amino acid sequence of domain 1 (amino acids 1–200) of IFNAR1, and do not bind to a peptide consisting of the amino acid sequence of domain 2 (amino acids 204–404) of IFNAR1.

Additionally provided herein are anti-IFNAR1 Fv clones that bind to amino acids 249, 291 and 296 of IFNAR1 in situ, do not bind to a peptide consisting of the amino acid sequence of domain I (amino acids 1–200) of IFNAR1, and do not bind to a peptide consisting of the amino acid sequence of domain 2 (amino acids 204–404) of IFNAR1.

II. Methods of Making Anti-IFNAR1 Hybridomas

The anti-IFNAR1 antibodies of the invention are preferably monoclonal. Also encompassed within the scope of the invention are Fab, Fab', Fab'-SH and $F(ab')_2$ fragments of the anti-IFNAR1 antibodies provided herein. These antibody fragments can be created by traditional means, such as enzymatic digestion, or may be generated by recombinant techniques. Such antibody fragments may be chimeric or humanized. These fragments are useful for the diagnostic and therapeutic,purposes set forth below.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-IFNAR1 monoclonal antibodies of the invention can be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to IFNAR1 generally are raised in animals by multiple subcutaneous (sc) or intraperitoneal (ip) injections of IFNAR1 and an adjuvant. In one embodiment, animals are immunized with a derivative of IFNAR1 that contains the extracellular domain (ECD) of IFNAR1 fused to the Fc portion of an immunoglobulin heavy chain. In a preferred embodiment, animals are immunized with an IFNAR1-IgG1 fusion protein as described in the Example below. Animals ordinarily are immunized against immunogenic conjugates or derivatives of IFNAR1 with monophosphoryl lipid A (MPL)/trehalose dicrynomycolate (TDM) (Ribi Immunochem. Research, Inc., Hamilton, Mont.) and the solution is injected intradermally at multiple sites. Two weeks later the animals are boosted. 7 to 14 days later animals are bled and the serum is assayed for anti-IFNAR1 titer. Animals are boosted until titer plateaus.

Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against IFNAR1. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies:Principles and Practice*, pp.59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Anti-IFNAR1 antibodies of the invention possessing the unique properties described in Section I above can be obtained by screening anti-IFNAR1 hybridoma clones for the desired properties by any convenient method. For example, if an anti-IFNAR1 monoclonal antibody that binds or does not bind to a particular IFNAR1 determinant(s) is desired, the candidate antibody can be screened for the presence or absence of differential affinity to wild type IFNAR1 and to mutant IFNAR1 that contains Ala substitution(s) at the determinant(s) of interest as described above. In one aspect, the candidate antibody can be tested for binding to wild type IFNAR1 and mutant IFNAR1 in an immunoprecipitation or immunoadsorption assay. For example, a capture ELISA can be used wherein plates are coated with a given density of wild type IFNAR1 or an equal density of mutant IFNAR1, the coated plates are contacted with equal concentrations of the candidate antibody, and the bound antibody is detected enzymatically, e.g. by contacting the bound antibody with HRP-conjugated anti-Ig antibody or biotinylated anti-Ig antibody, developing the bound anti-Ig antibody with streptavidin-HRP and/or hydrogen peroxide, and detecting the HRP color reaction by spectrophotometry at 490 nm with an ELISA plate reader. The candidate antibody that binds to the particular IFNAR1 determinant(s) of interest will exhibit binding activity with wild type IFNAR1 that is greater than the candidate antibody's binding activity with the corresponding Ala-substituted IFNAR1 mutant (i.e. a binding level with wild type IFNAR1 that is above the background binding level with mutant IFNAR1). Optionally, the candidate antibody that binds to the particular IFNAR1 determinant(s) of interest will exhibit binding activity with the corresponding Ala-substituted IFNAR1 mutant that is less than about 50%, or less than about 30%, or less than about 20%. or less than about 10%, or less than about 7%, or less than about 6%, or less than about 5%, or less than about 4%, or less than about 3%, or less than about 2%, or less than about 1%, or about 0% of the antibody's binding activity with wild type IFNAR1, e.g. as determined by dividing the HRP color reaction optical density observed for capture ELISA with IFNAR1 mutant adsorbent by the HRP color reaction optical density observed for capture ELISA with wild type IFNAR1 adsorbent. The candidate antibody that does not bind to the particular IFNAR1 determinant(s) of interest will exhibit similar or approximately the same binding activities with the corresponding Ala-substituted IFNAR1 mutant and wild type IFNAR1.

An anti-IFNAR1 monoclonal antibody that (1) binds to a conformational epitope on IFNAR1 or (2) does not bind to a peptide consisting of the amino acid sequence of domain 1 or domain 2 of IFNAR1 as provided herein can be detected by screening for failure to bind to completely denatured IFNAR1, or failure to bind to domain 1 peptide or domain 2 peptide, as desired, in an immunoblot system, e.g. using the candidate antibody to probe a Western blot of denaturing gel electrophoresed IFNAR1 or domain 1 or domain 2 peptides. Alternatively, the candidate antibody's inability to bind to completely denatured IFNAR1, domain 1 peptide or domain 2 peptide can be determined by immunoprecipitation or immunoadsorption techniques, e.g. a capture ELISA wherein plates are coated with the denatured IFNAR1, domain 1 peptide or domain 2 peptide, the coated plates are contacted with a solution of the candidate antibody, and the bound antibody is detected enzymatically, e.g. contacting the bound antibody with HRP-conjugated anti-Ig antibody and developing the HRP color reaction.

In another embodiment, the invention provides anti-IFNAR1 monoclonal antibodies that inhibit the anti-viral activity of a first type I interferon and do not inhibit the anti-viral activity of a second type I interferon. The anti-IFNAR1 antibodies of the invention can be obtained by screening candidate anti-IFNAR1 antibodies in any convenient type I interferon viral infectivity inhibition assay. Such assays are well known in the art, and include, for example, type I interferon-induced inhibition of encephalomyocarditis virus (EMC) infectivity in A549 cells as described in *Current Protocols in Immunology*, Coligan, J. E., Kruisbeek, A. M., Margulies, D. H., Shevach, E. M., and Strober, W., eds, Greene Publishing Associates and Wiley-Interscience, (1992), vol 1, unit 6.9.1. In another example, the assay uses type I interferon-induced inhibition of vesicular stomatitis virus (VSV) infectivity in Daudi cells as described by Dron and Tovey, *J. Gen. Virol.*, 64: 2641–2647 (1983). Generally, cells are seeded in attached cell culture plates, grown for 1 day, and then incubated for an additional day in the presence of various concentrations of a selected type I interferon and in the presence or absence of an excess of the candidate IFNAR1 antibody or a control antibody. Cells are challenged with virus, incubated for an additional day, and then viral activity is quantitated by detection of remaining viable cells (e.g. by cell staining) or by lysing cells, collecting culture supernatants and titering the virus concentrations present in the supernatants. The candidate antibody that inhibits the anti-viral activity of a selected type I interferon will inhibit more anti-viral activity than the baseline level of anti-viral activity inhibition measured in the presence of an equivalent concentration of control antibody. Optionally, the candidate antibody that inhibits the anti-viral activity of a selected type I interferon will inhibit at least about 50%, or at least about 70%, or at least about 80%, or at least about 90%, or at least about 95%, or at least about 99%, or about 100% of the activity of the type I interferon in the anti-viral activity assay as compared to baseline activity measured in the presence of an equivalent concentration of control antibody. The candidate antibody that does not inhibit the anti-viral activity of a selected type I interferon will exhibit similar or approximately the same level of anti-viral activity inhibition as control antibody.

In another embodiment, each type I interferon species used in the viral infectivity assay is titrated to a concentration that provides the same level of inhibition of viral activity as that induced by a preselected number of units of an IFN-α standard. This concentration serves to provide the normalized units of the subject type I interferon species. In order to assess the ability of an anti-IFNAR1 antibody to inhibit the anti-viral activity of various type I interferons, the effective concentration (EC50) of anti-(FNAR1 antibody for inhibiting 50% of a particular type I interferon's anti-viral activity (at the concentration titrated to provide the normalized units of activity) is determined for each type I interferon to be tested. In another embodiment, each type I interferon to be tested is normalized to at least at or about 1 unit/ml, or at or about 1 unit/ml to at or about 1,000 units/ml, or at or about 1 unit/ml to at or about 100 units/ml, of human IFN-α2. In yet another embodiment, each type I interferon to be tested is normalized to 10 units/ml of the NIH reference standard for recombinant human IFN-α2 (IFN-αA).

In still another embodiment, the candidate anti-IFNAR1 antibody that does not inhibit the anti-viral activity of a selected type I interferon will exhibit no effect at a concentration of up to at or about 1 μg/ml, or up to at or about 10 μg/ml, or up to at or about 20 μg/ml, or up to at or about 30 μg/ml, or up to at or about 50 μg/ml, or up to at or about 75 μg/ml, or up to at or about 100 μg/ml, against the anti-viral activity of the selected type I interferon in the A549 cell EMC viral infectivity assay described in *Current Protocols in Immunology*, Coligan, J. E., Kruisbeek, A. M., Margulies, D. H., Shevach, E. M., and Strober, W., eds, Greene Publishing Associates and Wiley-Interscience, (1992), vol. 2, unit 6.9.1, wherein the selected type I interferon is normalized to 10 units/ml of NIH reference standard for recombinant human IFN-α2 (IFN-αA).

In another embodiment, the candidate anti-IFNAR1 antibody that inhibits the anti-viral activity of a first type I interferon and does not inhibit the anti-viral activity of a second type I interferon will (1) exhibit an EC50 of up to at or about 1 μg/ml, or up to at or about 3 μg/ml, or up to at or about 6 μg/ml, or up to at or about 10 μg/ml, or up to at or about 20 μg/ml, or up to at or about 30 μg/ml, or up to at or about 40 μg/ml, or up to at or about 50 μg/ml, or up to at or about 75 μg/ml, or up to at or about 100 μg/ml, against the anti-viral activity of the first type I interferon in an A549 cell EMC viral infectivity assay, such as the A549 cell EMC viral infectivity assay described in *Current Protocols in Immunology*, supra, and (2) exhibit no effect at a concentration of up to at or about 30 μg/ml, or up to at or about 40 μg/ml, or up to at or about 50 μg/ml, or up to at or about 75 μg/ml, or up to at or about 100 μg/ml, against the anti-viral activity of the second type I interferon in the A549 cell EMC viral infectivity assay, wherein in the A549 cell EMC viral infectivity assay the first and second type I interferons are normalized to 10 units/ml of NIH reference standard for recombinant IFN-α2 (IFN-αA).

In yet another embodiment, the candidate anti-IFNAR1 antibody that inhibits the anti-viral activity of a first type I interferon and does not inhibit the anti-viral activity of a second type I interferon will (1) exhibit an EC50 of up to at or about 20 μg/ml against the anti-viral activity of the first type I interferon in an A549 cell EMC viral infectivity assay, such as the A549 cell EMC viral infectivity assay described in *Current Protocols in Immunology*, supra, and (2) exhibit no effect at a concentration of 30 μg/ml against the anti-viral activity of the second type I interferon in the A549 cell EMC viral infectivity assay, wherein in the A549 cell EMC viral infectivity assay the first and second type I interferons are normalized to 10 units/ml of NIH reference standard for recombinant IFN-α2 (IFN-αA).

In yet another embodiment, the candidate anti-IFNAR1 antibody that inhibits the anti-viral activity of a first type I interferon and does not inhibit the anti-viral activity of a second type I interferon will (1) exhibit an EC50 of up to at or about 10 μg/ml against the anti-viral activity of the first type I interferon in an A549 cell EMC viral infectivity assay, such as the A549 cell EMC viral infectivity assay described in *Current Protocols in Immunology*, supra, and (2) exhibit no effect at a concentration of 30 μg/ml against the anti-viral activity of the second type I interferon in the A549 cell EMC viral infectivity assay, wherein in the A549 cell EMC viral infectivity assay the first and second type I interferons are normalized to 10 units/ml of NIH reference standard for recombinant IFN-α2 (IFN-αA).

In yet another embodiment, the candidate anti-IFNAR1 antibody that inhibits the anti-viral activity of a first type I interferon and does not inhibit the anti-viral activity of a second type I interferon will (1) exhibit an EC50 of up to at or about 6 μg/ml against the anti-viral activity of the first type I interferon in an A549 cell EMC viral infectivity assay, such as the A549 cell EMC viral infectivity assay described in *Current Protocols in Immunology*, supra, and (2) exhibit no effect at a concentration of 30 μg/ml against the anti-viral activity of the second type >interferon in the A549 cell EMC viral infectivity assay, wherein in the A549 cell EMC viral infectivity assay the first and second type I interferons are normalized to I0 units/ml of NIH reference standard for recombinant IFN-α2 (IFN-αA).

In yet another embodiment, the candidate anti-IFNAR1 antibody that inhibits the anti-viral activity of a first type I interferon and does not inhibit the anti-viral activity of a second type I interferon will (1) exhibit an EC50 of up to at or about 3 μg/ml against the anti-viral activity of the first type I interferon in an A549 cell EMC viral infectivity assay, such as the A549 cell EMC viral infectivity assay described in *Current Protocols in Immunology*, supra, and (2) exhibit no effect at a concentration of 30 μg/ml against the anti-viral activity of the second type I interferon in the A549 cell EMC viral infectivity assay, wherein in the A549 cell EMC viral infectivity assay the first and second type I interferons are normalized to 10 units/ml of NIH reference standard for recombinant IFN-α2 (IFN-αA).

In yet another embodiment, the candidate anti-IFNAR1 antibody that inhibits the anti-viral activity of a first type I interferon and does not inhibit the anti-viral activity of a second type I interferon will (1) exhibit an EC50 of up to at or about 1 μg/ml against the anti-viral activity of the first type I interferon in an A549 cell EMC viral infectivity assay, such as the A549 cell EMC viral infectivity assay described in *Current Protocols in Immunology*, supra, and (2) exhibit no effect at a concentration of 30 μg/ml against the anti-viral activity of the second type I interferon in the A549 cell EMC viral infectivity assay, wherein in the A549 cell EMC viral infectivity assay the first and second type I interferons are normalized to 10 units/ml of NIH reference standard for recombinant IFN-α2 (IFN-αA).

In another aspect, the invention provides an anti-IFNAR1 antibody that inhibits the anti-viral activity of a first type I interferon selected from the group consisting of IFNα2, IFN-α8, and IFN-α5 and does not inhibit the anti-viral activity of a second type I interferon.

Also provided herein is an anti-IFNAR1 antibody that inhibits the anti-viral activity of a first type I interferon and does not inhibit the anti-viral activity of a second type T interferon selected from the group consisting of IFN-α2, IFN-α8, IFN-α$_{II}$1, and IFN-β.

In yet another embodiment, the anti-IFNAR1 inhibits the anti-viral activity of a first type I interferon and does not inhibit the anti-viral activity of a second type I interferon selected from the group consisting of IFN-α1, IFN-α21, and IFN-β.

Additionally provided herein is an anti-IFNAR1 antibody that inhibits the anti-viral activity of a first type I interferon selected from the group consisting of IFN-α2, IFN-α8, and IFN-α5 and does not inhibit the anti-viral activity of a second type I interferon selected from the group consisting of IFN-α1, IFN-21, and IFN-β.

Further provided herein is anti-IFNAR1 antibody that inhibits the anti-viral activity of a first type I interferon selected from the group consisting of IFN-α2, IFN-α1, IFN-α21, and IFN-β.

Also encompassed herein is an anti-IFNAR1 antibody that inhibits the anti-viral activity of a first type I interferon and does not inhibit the anti-viral activity of a second type I interferon selected from the group consisting of IFN-α8 and IFN-α5.

Further encompassed herein is an anti-IFNAR1 antibody that inhibits the anti-viral activity of a first type I interferon selected from the group consisting of IFN-α2, IFN-α1, IFN-α21, and IFN-β and does not inhibit the anti-viral activity of a second type I interferon selected from the group consisting of IFN-α8 and IFN-α5.

The invention further provides an anti-IFNAR1 antibody that inhibits the anti-viral activity of more than one selected type I interferon and does not inhibit the anti-viral activity of another selected type I interferon.

In one embodiment, the invention provides an anti-IFNAR1 antibody that inhibits the anti-viral activity of IFN-α2, IFN-α8, and IFN-α5 and does not inhibit the anti-viral activity of another type I interferon. In another embodiment, the invention provides an anti-IFNAR1 antibody that inhibits the anti-viral activity of IFN-α2, IFN-α8 and IFN-α5 and does not inhibit the anti-viral activity of another type I interferon selected from the group consisting of IFN-α1, IFN-α21, and IFN-β.

In another embodiment, the invention provides an anti-IFNAR1 antibody that inhibits the anti-viral activity of IFN-α2, IFN-α8, IFN-α1 and IFN-α5 and does not inhibit the anti-viral activity of IFN-β.

In another embodiment, the invention provides an anti-IFNAR1 antibody that inhibits the anti-viral activity of IFN-α2, IFN-α8, IFN-α1 and IFN-α5 and does not inhibit the anti-viral activity of IFN-β, wherein (1) the antibody exhibits an EC50 of up to at or about 1 μg/ml, or up to at or about 3 μg/ml, or up to at or about 6 μg/ml, or up to at or about 10 μg/ml, or up to at or about 20 μg/ml, or up to at or about 30 μg/ml, or up to at or about 40 μg/ml, or up to at or about 50 μg/ml, or up to at or about 75 μg/ml, or up to at or about 100 μg/ml, against the anti-viral activities of IFN-α2, IFN-α8, IFN-α1 and IFN-α5 in an A549 cell EMC viral infectivity assay, such as the A549 cell EMC viral infectivity assay described in Current Protocols in Immunology, supra, and (2) the antibody exhibits no effect at a concentration of up to at or about 30 μg/ml, or up to at or about 40 μg/ml, or up to at or about 50 μg/ml, or up to at or about 75 μg/ml, or up to at or about 100 μg/ml, against the anti-viral activity of the IFN-β in the A549 cell EMC viral infectivity assay, and wherein in the A549 cell EMC viral infectivity assay each type I interferon is normalized to 10 units/ml of NIH reference standard for recombinant IFN-α2 (IFN-αA).

In another embodiment, the invention provides an anti-IFNAR1 antibody that inhibits the anti-viral activity of IFN-α2, IFN-α8, IFN-α1 and IFN-α5 and does not inhibit the anti-viral activity of IFN-β, wherein (1) the antibody exhibits an EC50 of up to at or about 10 μg/ml against the anti-viral activity of IFN-α1 in an A549 cell EMC viral infectivity assay, such as the A549 cell EMC viral infectivity assay described in Current Protocols in Immunology, supra, (2) the antibody exhibits an EC50 of up to at or about 10 μg/ml against the anti-viral activity of IFN-α2 in the A549 cell EMC viral infectivity assay, (3) the antibody exhibits an EC50 of up to at or about 6 μg/ml against the anti-viral activity of IFN-α5 in the A549 cell EMC viral infectivity assay, (4) the antibody exhibits an EC50 of up to at or about 3 μg/ml against the anti-viral activity of IFN-α8 in the A549 cell EMC viral infectivity assay, and (5) the antibody exhibits no effect at a concentration of up to at or about 30 μg/ml against the anti-viral activity of the IFN-β in the A549 cell EMC viral infectivity assay, and wherein in the A549 cell EMC viral infectivity assay each type I interferon is normalized to I0 units/ml of NIH reference standard for recombinant IFN-α2 (IFN-αA).

In another embodiment, the invention provides an anti-IFNAR1 antibody that inhibits the anti-viral activity of IFN-α2, IFN-α8, IFN-α1 and IFN-α5 and does not inhibit the anti-viral activity of IFN-β, wherein (1) the antibody exhibits an EC50 of up to at or about 3 μg/ml against the anti-viral activity of IFN-α1 in an A549 cell EMC viral infectivity assay, such as the A549 cell EMC viral infectivity assay described in Current Protocols in Immunology, supra, (2) the antibody exhibits an EC50 of up to at or about 1 μg/ml against the anti-viral activity of IFN-α2 in the A549 cell EMC viral infectivity assay, (3) the antibody exhibits an EC50 of up to at or about 1 μg/ml against the anti-viral activity of IFN-α5 in the A549 cell EMC viral infectivity assay, (4) the antibody exhibits an EC50 of up to at or about 1 μg/ml against the anti-viral activity of IFN-α8 in the A549 cell EMC viral infectivity assay, and (5) the antibody exhibits no effect at a concentration of up to at or about 30 μg/ml against the anti-viral activity of the IFN-β in the A549 cell EMC viral infectivity assay, and wherein in the A549 cell EMC viral infectivity assay each type I interferon is normalized to 10 units/ml of NIH reference standard for recombinant IFN-α2 (IFN-αA).

In yet another embodiment, the invention provides an anti-IFNAR1 antibody that inhibits the anti-viral activity of IFN-α2, IFN-α1, IFN-α21, and IFN-β and does not inhibit the anti-viral activity of another type I interferon. In still another embodiment, the invention provides an anti-IFNAR1 antibody that inhibits the anti-viral activity of IFN-α2, IFN-α1, IFN-α21, and IFN-β and does not inhibit the anti-viral activity of another type I interferon selected from the group consisting of IFN-α8 and IFN-α21.

In a further embodiment, the invention provides an anti-IFNAR1 antibody that inhibits the anti-viral activity of IFN-α1 and IFN-β and does not inhibit the anti-viral activity of another type I interferon. In an additional embodiment, the invention provides an anti-IFNAR1 antibody that inhibits the anti-viral activity of IFN-α1 and IFN-β and does not inhibit the anti-viral activity of another type I interferon selected from the group consisting of IFN-α2, IFN-α8, IFN-α21 and IFN-α5.

The invention additionally provides an anti-IFNAR1 antibody that inhibits the anti-viral activity of a first type I interferon and that does not inhibit the anti-viral activity of more than one other type I interferon.

In one embodiment, the invention provides an anti-IFNAR1 that inhibits the anti-viral activity of a first type I interferon and does not inhibit the anti-viral activity of any type I interferon in the group consisting of IFN-α1, IFN-α21, and IFN-β. In another embodiment, the invention provides an anti-IFNAR1 antibody that inhibits the anti-viral activity of a first type I interferon and does not inhibit the anti-viral activity of any type I interferon in the group consisting of IFN-α8 and IFN-α5. In yet another embodiment, the invention provides an anti-IFNAR1 antibody that inhibits the anti-viral activity of a first type I interferon and does not inhibit the anti-viral activity of any type I interferon in the group consisting of IFN-α2, IFN-α8, IFN-α21 and IFN-α21.

Further provided herein is an anti-IFNAR1 antibody that inhibits the anti-viral activity of at least two species of type I interferon and that does not inhibit the anti-viral activity of at least two more species of type I interferon.

In another embodiment, the invention provides an anti-IFNAR1 antibody that inhibits the anti-viral activity of IFN-α2, IFN-α8, and IFN-α5 does not inhibit the anti-viral activity of any type I interferon in the group consisting of IFN-α1, IFN-α21, and IFN-β.

In yet another embodiment, the invention provides an anti-IFNAR1 antibody that inhibits the anti-viral activity of IFN-α2, IFN-α1, IFN-α21, and IFN-β and does not inhibit the anti-viral activity of any type I interferon in the group consisting of IFN-α8 and IFN-α5.

In still another embodiment, the invention provides an anti-IFNAR1 antibody that inhibits the anti-viral activity of IFN-α1 and IFN-β and does not inhibit the anti-viral activity of any type I interferon in the group consisting of IFN-α2, IFN-α8, IFN-α21, and IFN-α5.

In other embodiments, the invention provides anti-IFNAR1 antibodies which possess combinations of the type I interferon anti-viral inhibiting and/or non-inhibiting properties and the IFNAR1 determinant binding and/or non-binding properties described herein. Anti-IFNAR1 antibodies corresponding to these embodiments can be obtained by using combinations of the type I anti-viral activity inhibitions assays described above for selection of antibodies with unique type I interferon inhibiting/non-inhibiting properties and immunoprecipitation or immunoadsorption screening procedures for selection of antibodies with unique IFNAR1 determinant binding/non-binding properties.

For example, the invention provides an anti-IFNAR1 antibody that inhibits the anti-viral activity of a first type I interferon and does not inhibit the anti-viral activity of a second type I interferon, binds to one or more amino acids in situ in the sequence of amino acids 103–111 of IFNAR1, and does not bind to one or more amino acids in situ in the sequence of amino acids 244–249 of IFNAR1.

In a preferred embodiment, the invention provides an anti-IFNAR1 antibody that inhibits the anti-viral activity of a first type I interferon selected from the group consisting of IFN-α2, IFN-α8, and IFN-α5 and does not inhibit the anti-viral activity of a second type I interferon, binds to one or more amino acids in situ in the sequence of amino acids 103–11 1 of IFNAR1, and does not bind to one or more amino acids in situ in the sequence of amino acids 244–249 of IFNAR1.

In another preferred embodiment, the invention provides an anti-IFNAR1 antibody that inhibits the anti-viral activity of a first type I interferon and does not inhibit the anti-viral activity of a second type I interferon selected from the group consisting of IFN-α1, IFN-α21, and IFN-β, binds to one or more amino acids in situ in the sequence of amino acids 103–111 of IFNAR1, and does not bind to one or more amino acids in situ in the sequence of amino acids 244–249 of IFNAR1.

In yet another preferred embodiment, the invention provides an anti-IFNAR1 antibody that inhibits the anti-viral activity of more than one selected type I interferon, does not inhibit the anti-viral activity of another selected type I interferon to IFNAR1, binds to one or more amino acids in situ in the sequence of amino acids 103–111 of IFNAR1, and does not bind to one or more amino acids in situ in the sequence of amino acids 244–249 of IFNAR1.

In one preferred embodiment, the invention provides an anti-IFNAR1 antibody that inhibits the anti-viral activity of IFN-α2, IFN-α8, and IFN-α5, does not inhibit the anti-viral activity of another selected type I interferon to IFNAR1, binds to one or more amino acids in situ in the sequence of amino acids 103–111 of IFNAR1, and does not bind to one or more amino acids in situ in the sequence of amino acids 244–249 of IFNAR1. In another preferred embodiment, the invention provides an anti-IFNAR1 antibody that inhibits the anti-viral activity of IFN-α2, IFN-α8 and IFN-α5, does not inhibit the anti-viral activity of another type I interferon selected from the group consisting of IFN-α1, IFN-α21, and IFN-β, binds to one or more amino acids in situ in the sequence of amino acids 103–111 of IFNAR1, and does not bind to one or more amino acids in situ in the sequence of amino acids 244–249 of IFNAR1.

In yet another preferred embodiment, the invention provides an anti-IFNAR1 antibody that inhibits the anti-viral activity of IFN-α1 and IFN-β, does not inhibit the anti-viral activity of another selected type I interferon to IFNAR1, binds to one or more amino acids in situ in the sequence of amino acids 103–111 of IFNAR1, and does not bind to one or more amino acids in situ in the sequence of amino acids 244–249 of IFNAR1. In still another preferred embodiment, the invention provides an anti-IFNAR1 antibody that inhibits the anti-viral activity of IFN-α1 and IFN-β, does not inhibit the anti-viral activity of another type I interferon selected from the group consisting of IFN-α2, IFN-α8, IFN-α21 and IFN-α5, binds to one or more amino acids in situ in the sequence of amino acids 103–111 of IFNAR1, and does not bind to one or more amino acids in situ in the sequence of amino acids 244–249 of IFNAR1.

Additionally preferred is an anti-IFNAR1 antibody that inhibits the anti-viral activity of a selected type I interferon to IFNAR1, does not inhibit the anti-viral activity of more than one other type I interferon to IFNAR1, binds to one or more amino acids in situ in the sequence of amino acids 103–111 of IFNAR1, and does not bind to one or more amino acids in situ in the sequence of amino acids 244–249 of IFNAR1.

In another preferred embodiment, the invention provides an anti-IFNAR1 antibody that inhibits the anti-viral activity of a selected type I interferon, does not inhibit the anti-viral activity of any type I interferon in the group consisting of IFN-α1, IFN-α21, and IFN-β, binds to one or more amino acids in situ in the sequence of amino acids 103–111 of IFNAR1, and does not bind to one or more amino acids in situ in the sequence of amino acids 244–249 of IFNAR1. In yet another preferred embodiment, the invention provides an anti-IFNAR1 antibody that inhibits the anti-viral activity of a selected type I interferon, does not inhibit the anti-viral activity of any type I interferon in the group consisting of IFN-α2, IFN-α8, IFN-α21, IFN-α5, binds to one or more amino acids in situ in the sequence of amino acids 103–111 of IFNAR1, and does not bind to one or more amino acids in situ in the sequence of amino acids 244–249 of IFNAR1.

Further preferred embodiments include an anti-IFNAR1 antibody that inhibits the anti-viral activity of at least two species of type I interferon, does not inhibit the anti-viral activity of at least two more species of type I interferon, binds to one or more amino acids in situ in the sequence of amino acids 103–111 of IFNAR1, and does not bind to one or more amino acids in situ in the sequence of amino acids 244–249 of IFNAR1.

In another preferred embodiment, the invention provides an anti-IFNAR1 antibody that inhibits the anti-viral activity of IFN-α2, IFN-α8 and IFN-α5, does not inhibit the anti-viral activity of any type I interferon in the group consisting of IFN-α1, IFN-α21 and IFN-β, binds to one or more amino acids in situ in the sequence of amino acids 103–111 of IFNAR1, and does not bind to one or more amino acids in situ in the sequence of amino acids 244–249 of IFNAR1.

In yet another preferred embodiment, the invention provides an anti-IFNAR1 antibody that inhibits the anti-viral activity of IFN-α1 and IFN-β, does not inhibit the anti-viral activity of any type I interferon in the group consisting of IFN-αA, IFN-αB, IFN-αF, and IFN-αG, binds to one or more amino acids in situ in the sequence of amino acids 103–111 of IFNAR1, and does not bind to one or more amino acids in situ in the sequence of amino acids 244–249 of IFNAR1.

In a further preferred embodiment, the invention provides anti-IFNAR1 antibodies that inhibit the anti-viral activity of a first type I interferon, do not inhibit the anti-viral activity of a second type I interferon and IFNAR1, bind to one or more amino acids in situ in the sequence of amino acids 103–111 of IFNAR1, and do not bind to amino acid 249 of IFNAR1.

In a preferred embodiment, the invention provides an anti-IFNAR1 antibody that inhibits the anti-viral activity of a first type I interferon selected from the group consisting of IFN-αA, IFN-α8, and IFN-α5, do not inhibit the anti-viral activity of a second type I interferon and IFNAR1, bind to one or more amino acids in situ in the sequence of amino acids 103–111 of IFNAR1, and do not bind to amino acid 249 of IFNAR1.

In another preferred embodiment, the invention provides an anti-IFNAR1 antibody that inhibits the anti-viral activity of a first type I interferon, does not inhibit the anti-viral activity of a second type I interferon selected from the group consisting of IFN-α1, IFN-α21, and IFN-β, bind to one or more amino acids in situ in the sequence of amino acids 103–111 of IFNAR1, and do not bind to amino acid 249 of IFNAR1.

In yet another preferred embodiment, the invention provides an anti-IFNAR1 antibody that inhibits the anti-viral activity of more than one selected type I interferon, does not inhibit the anti-viral activity of another selected type I interferon, binds to one or more amino acids in situ in the sequence of amino acids 103–111 of IFNAR1, and does not bind to amino acid 249 of IFNAR1 in situ.

In one preferred embodiment, the invention provides an anti-IFNAR1 antibody that inhibits the anti-viral activity of IFN-α2, IFN-α8, and IFN-α5, does not inhibit the anti-viral activity of another selected type I interferon, binds to one or more amino acids in situ in the sequence of amino acids 103–111 of IFNAR1, and does not bind to amino acid 249 of IFNAR1 in situ. In another preferred embodiment, the invention provides an anti-IFNAR1 antibody that inhibits the anti-viral activity of IFN-α2, IFN-α8 and IFN-α5, does not inhibit the anti-viral activity of another type I interferon selected from the group consisting of IFN-α1, IFN-α21, and IFN-β, binds to one or more amino acids in situ in the sequence of amino acids 103–111 of IFNAR1, and does not bind to amino acid 249 of IFNAR1 in situ.

In yet another preferred embodiment, the invention provides an anti-IFNAR1 antibody that inhibits the anti-viral activity of IFN-α1 and IFN-β, does not inhibit the anti-viral activity of another selected type I interferon, binds to one or more amino acids in situ in the sequence of amino acids 103–111 of IFNAR1, and does not bind to amino acid 249 of IFNAR1 in situ. In still another preferred embodiment, the invention provides an anti-IFNAR1 antibody that inhibits the anti-viral activity of IFN-α1 and IFN-β, does not inhibit the anti-viral activity of another type I interferon selected from the group consisting of IFN-α2, IFN-α8, IFN-α21 and IFN-α5, binds to one or more amino acids in situ in the sequence of amino acids 103–111 of IFNAR1, and does not bind to amino acid 249 of IFNAR1 in situ.

Additionally preferred is an anti-IFNAR1 antibody that inhibits the anti-viral activity of a first type I interferon, does not inhibit the anti-viral activity of more than one other type I interferon to IFNAR1, binds to one or more amino acids in situ in the sequence of amino acids 103–111 of IFNAR1, and does not bind to amino acid 249 of IFNAR1 in situ. In another preferred embodiment, the invention provides an anti-IFNAR1 Fv antibody that inhibits the anti-viral activity of a first type I interferon, does not inhibit the anti-viral activity of any type I interferon in the group consisting of IFN-α1, IFN-α21, IFN-β, binds to one or more amino acids in situ in the sequence of amino acids 103–111 of IFNAR1, and does not bind to amino acid 249 of IFNAR1 in situ.

Further preferred embodiments include anti-IFNAR1 antibodies that inhibit the anti-viral activity of at least two species of type I interferon, do not inhibit the anti-viral activity of at least two more species of type I interferon, bind to one or more amino acids in situ in the sequence of amino acids 103–111 of IFNAR1, and do not bind to amino acid 249 of IFNAR1 in situ. In yet another preferred embodiment, the invention provides an anti-IFNAR1 antibody that inhibits the anti-viral activity of IFN-α2, IFN-α8, and IFN-α5, does not inhibit the anti-viral activity of any type I interferon in the group consisting of IFN-α1, IFN-α21, IFN-β, bind to one or more amino acids in situ in the sequence of amino acids 103–111 of IFNAR1, and do not bind to amino acid 249 of IFNAR1 in situ. In a further embodiment, the invention provides an anti-IFNAR1 antibody that inhibits the anti-viral activity of IFN-α1 and IFN-β, does not inhibit the anti-viral activity of any type I interferon in the group consisting of IFN-α2, IFN-α8, IFN-α21, and IFN-α5, binds to one or more amino acids in situ in the sequence of amino acids 103–111 of IFNAR1, and does not bind to amino acid 249 of IFNAR1 in situ.

In another preferred embodiment, the invention provides anti-IFNAR1 antibodies that inhibit the anti-viral activity of a first type I interferon and IFNAR1, do not inhibit the anti-viral activity of a second type I interferon and IFNAR1, bind to one or more amino acids in situ in the sequence of amino acids 103–111 of IFNAR1, bind to amino acids 291 and 296 of IFNAR1, and do not bind to amino acid 249 of IFNAR1.

In one preferred embodiment, the anti-IFNAR1 antibody inhibits the anti-viral activity of a first type I interferon selected from the group consisting of IFN-α2, IFN-α8, and IFN-α5, does not inhibit the anti-viral activity of a second type I interferon, binds to one or more amino acids in situ in the sequence of amino acids 103–111 of IFNAR1, binds to amino acids 291 and 296 of IFNAR1, and does not bind to amino acid 249 of IFNAR1.

In another preferred embodiment, the anti-IFNAR1 antibody inhibits the anti-viral activity of a first type I interferon, does not inhibit the anti-viral activity of a second type I interferon selected from the group consisting of IFN-α1, IFN-α21, and IFN-β, binds to one or more amino acids in situ in the sequence of amino acids 103–111 of IFNAR1, binds to amino acids 291 and 296 of IFNAR1, and does not bind to amino acid 249 of IFNAR1.

In yet another preferred embodiment, the invention provides anti-IFNAR1 antibodies that inhibit the anti-viral activity of more than one selected type I interferon to IFNAR1, do not inhibit the anti-viral activity of another selected type I interferon to IFNAR1, bind to one or more amino acids in situ in the sequence of amino acids 103–111 of IFNAR1, bind to amino acids 291 and 296 of IFNAR1 in situ, and do not bind to amino acid 249 of IFNAR1 in situ. In one preferred embodiment, the invention provides an anti-IFNAR1 antibody that inhibits the anti-viral activity of IFN-α2, IFN-α8, and IFN-α5, do not inhibit the anti-viral activity of another selected type I interferon to IFNAR1, bind to one or more amino acids in situ in the sequence of amino acids 103–111 of IFNAR1, bind to amino acids 291 and 296 of IFNAR1 in situ, and do not bind to amino acid 249 of IFNAR1 in situ. In still another preferred embodiment, the invention provides an anti-IFNAR1 antibody that inhibits the anti-viral activity of IFN-α2, IFN-α8 and IFN-α5, does not inhibit the anti-viral activity of another type I interferon selected from the group consisting of IFN-α1, IFN-α21, and IFN-β, binds to one or more amino acids in situ in the sequence of amino acids 103–111 of IFNAR1, binds to amino acids 291 and 296 of IFNAR1 in situ, and do not bind to amino acid 249 of IFNAR1 in situ.

Additionally preferred are anti-IFNAR1 antibodies that inhibit the anti-viral activity of a selected type I interferon, do not inhibit the anti-viral activity of more than one other type I interferon, bind to one or more amino acids in situ in the sequence of amino acids 103–111 of IFNAR1, bind to amino acids 291 and 296 of IFNAR1 in situ, and do not bind to amino acid 249 of IFNAR1 in situ. Also preferred are anti-IFNAR1 antibodies that inhibit the anti-viral activity of a selected type I interferon, do not inhibit the anti-viral activity of any type I interferon in the group consisting of IFN-IFN-α1, IFN-α21, and IFN-β, bind to one or more amino acids in situ in the sequence of amino acids 103–111 of IFNAR1, bind to amino acids 291 and 296 of IFNAR1 in situ, and do not bind to amino acid 249 of IFNAR1 in situ.

Further preferred embodiments include anti-IFNAR1 antibodies that inhibit the anti-viral activity of at least two species of type I interferon, do not inhibit the anti-viral activity of at least two more species of type I interferon, bind to one or more amino acids in situ in the sequence of amino acids 103–111 of IFNAR1, bind to amino acids 291 and 296 in situ, and do not bind to amino acid 249 of IFNAR1 in situ. In yet another preferred embodiment, the invention provides an anti-IFNAR1 antibody that inhibits the anti-viral activity of IFN-α2, IFN-α8, and IFN-α5, does not inhibit the anti-viral activity of any type I interferon in the group consisting of IFN-α1, IFN-α21, and IFN-β, bind to one or more amino acids in situ in the sequence of amino acids 103–20 111 of IFNAR1, bind to amino acids 291 and 296 in situ, and do not bind to amino acid 249 of IFNAR1 in situ.

The invention additionally provides anti-IFNAR1 antibodies which inhibit the anti-viral activity of IFN-α2, IFN-α8, and IFN-α5, which do not block the anti-viral activity of IFN-β, and which bind to one or more amino acids in situ in the sequence of amino acids 244–249 of IFNAR1 and bind to one or more amino acids in situ in the sequence of amino acids 291–298 of IFNAR1. Thus, the invention includes an anti-IFNAR1 antibody (1) which possesses any pattern of IFN-β-non-inhibiting and IFN-α2, IFN-α8, and IFN-α5-inhibiting activity described above (2) which binds to one or more amino acids in situ in the sequence of amino acids 244–249 of IFNAR1 and (3) which binds to one or more amino acids in situ in the sequence of amino acids 291–298 of IFNAR1.

The invention also provides anti-IFNAR1 antibodies which inhibit the anti-viral activity of IFN-α2, IFN-α8, IFN-α1, and IFN-α5, which do not block the anti-viral activity of IFN-β, and which bind to one or more amino acids in situ in the sequence of amino acids 244–249 of IFNAR1 and bind to one or more amino acids in situ in the sequence of amino acids 291–298 of IFNAR1. Thus, the invention includes an anti-IFNAR1 antibody (1) which possesses any pattern of IFN-β-non-inhibiting and IFN-α2-, IFN-α8-, IFN-α1-, and IFN-α5-inhibiting activity described above (2) which binds to one or more amino acids in situ in the sequence of amino acids 244–249 of IFNAR1 and (3) which binds to one or more amino acids in situ in the sequence of amino acids 291–298 of IFNAR1.

The invention also encompasses anti-IFNAR1 antibodies which inhibit the anti-viral activity of IFN-α2, IFN-α8, and IFN-α5, which do not inhibit the anti-viral activity of IFN-β, and which bind to amino acids 249, 291 and 296 of IFNAR1 in situ. Thus, the invention includes an anti-IFNAR1 antibody (1) which possesses any pattern of IFN-β-non-inhibiting and IFN-α2-, IFN-α8-, and IFN-α5-inhibiting activity described above and (2) which binds to amino acids 249, 291 and 296 of IFNAR1 in situ.

The invention further provides anti-IFNAR1 antibodies which inhibit the anti-viral activity of IFN-α2, IFN-α8, IFN-α1, and IFN-α5, which do not inhibit the anti-viral activity of IFN-β, and which bind to amino acids 249, 291 and 296 of IFNAR1 in situ. Thus, the invention includes an anti-IFNAR1 antibody (1) which possesses any pattern of IFN-β-non-inhibiting and IFN-α2, IFN-α8, IFN-α1, and IFN-α5-inhibiting activity described above and (2) which binds to amino acids 249, 291 and 296 of IFNAR1 in situ.

In another embodiment, the invention provides any of the anti-IFNAR1 antibodies described above that additionally binds to a conformational epitope on IFNAR1. Such anti-IFNAR1 antibodies can be obtained by adding the above-described denatured IFNAR1 immunoblotting or immunoadsorption assay to the series of procedures used to screen for the other desired antibody properties described above. It will be appreciated that the denatured IFNAR1 immunoblotting or immunoadsorption assay can be performed before, after, or at any convenient point during the other selection procedures for the anti-IFNAR1 antibody of interest.

In a further embodiment, the invention provides anti-IFNAR1 antibodies that inhibit the anti-viral activity of a first type I interferon, do not inhibit the anti-viral activity of a second type I interferon, and bind to a conformational epitope of IFNAR1.

In yet another embodiment, the invention provides anti-IFNAR1 antibodies that inhibit the anti-viral activity of a first type I interferon selected from the group consisting of IFN-α2, IFN-α8, and IFN-α5, do not inhibit the anti-viral activity of a second type I interferon, and bind to a conformational epitope of IFNAR1.

In still another embodiment, the invention provides anti-IFNAR1 antibodies that inhibit the anti-viral activity of a first type I interferon, do not inhibit the anti-viral activity of a second type I interferon selected from the group consisting of IFN-α1, IFN-α21, and IFN-β, and bind to a conformational epitope of IFNAR1.

In a further embodiment, the invention provides anti-IFNAR1 antibodies that inhibit the anti-viral activity of a first type I interferon selected from the group consisting of IFN-α2, IFN-α8, and IFN-α5, do not inhibit the anti-viral activity of a second type I interferon selected from the group consisting of I Further provided herein are anti-IFNAR1 antibodies that inhibit the anti-viral activity of IFN-α2, IFN-α8, IFN-α1, and IFN-α5, do not inhibit the anti-viral activity of IFN-β, bind to one or more of amino acids 244–249 of IFNAR1 in situ, bind to one or more of amino acids 291–5 298 of IFNAR1 in situ, do not bind to a peptide consisting of the amino acid sequence of domain 1 (amino acids 1–200) of IFNAR1, and do not bind to a peptide consisting of the amino acid sequence of domain 2 (amino acids 204–404) of IFNAR1. Thus, the invention includes an anti-IFNAR1 antibody (1) which possesses any pattern of IFN-β-non-inhibiting and IFN-α2-, IFN-α8-, IFN-α1-, and IFN-α5-inhibiting activity described above (2) which binds to one or more of amino acids 244–249 of IFNAR1 in situ (3) which binds to one or more of amino acids 291–298 of IFNAR1 in situ (4) which does not bind to a peptide consisting of the amino acid sequence of domain 1 (amino acids 1–200) of IFNAR1 and (5) which does not bind to a peptide consisting of the amino acid sequence of domain 2 (amino acids 204–404) of IFNAR1.

Additionally provided herein are anti-IFNAR1 antibodies that inhibit the anti-viral activity of IFN-α2, IFN-α8, IFN-α1, and IFN-α5, do not inhibit the anti-viral activity of IFN-β, bind to amino acids 249, 291 and 298 in IFNAR1 in situ, do not bind to a peptide consisting of the amino acid sequence of domain 1 (amino acids 1–200) of IFNAR1, and do not bind to a peptide consisting of the amino acid sequence of domain 2 (amino acids 204–404) of IFNAR1.

Thus, the invention includes an anti-IFNAR1 antibody (1) which possesses any pattern of IFN-β-non-inhibiting and IFN-α2-, IFN-α8-, IFN-α1-, and IFN-α5-inhibiting activity described above (2) which binds to amino acids 249, 291 and 296 of IFNAR1 in situ (3) which does not bind to a peptide consisting of the amino acid sequence of domain 1 (amino acids 1–200) of IFNAR1 and (4) which does not bind to a peptide consisting of the amino acid sequence of domain 2 (amino acids 204–404) of IFNAR1.

In another embodiment, the invention provides the anti-IFNAR1 monoclonal antibody produced by hybridoma cell line 5A8 (ATCC Deposit No. HB 12129).

In yet another embodiment, the invention provides the anti-IFNAR1 monoclonal antibody produced by hybridoma cell line 2E8 (ATCC Deposit No. HB 12130).

In still another embodiment, the invention provides the anti-IFNAR1 monoclonal antibody produced by hybridoma cell line 2H6 (ATCC Deposit No. HB 12131).

In a further embodiment, the invention provides the anti-IFNAR1 monoclonal antibody produced by hybridoma cell line 4A7 (ATCC Deposit No. HB 12132).

In an additional embodiment, the invention provides the anti-IFNAR1 monoclonal antibody produced by hybridoma cell line 2E1 (ATCC Deposit No. HB 12133).

In still another-embodiment, the invention provides anti-IFNAR1 monoclonal antibodies that compete with 5A8 antibody, 2E8 antibody, 2H6 antibody, 4A7 antibody, or 2E1 antibody for binding to IFNAR1. Such competitor antibodies include antibodies that recognize an IFNAR1 epitope that is the same as or overlaps with the IFNAR1 epitope recognized by an antibody selected from the group consisting of the 5A8, 2E8, 2H6, 4A7 and 2E1 antibodies. Such competitor antibodies can be obtained by screening anti-IFNAR1 hybridoma supernatants for binding to immobilized IFNAR1 in competition with labeled 5A8 antibody, 2E8 antibody, 2H6 antibody, 4A7 antibody or 2E1 antibody. A hybridoma supernatant containing competitor antibody will reduce the amount of bound, labeled antibody detected in the subject competition binding mixture as compared to the amount of bound, labeled antibody detected in a control binding mixture containing irrelevant (or no) antibody. Any of the competition binding assays described in Section IV below is suitable for use in the foregoing procedure.

III. Methods of Constructing Recombinant Anti-IFNAR1 Antibodies

DNA encoding the hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding anti-IFNAR1 antibody derived from a hybridoma of the invention can also be modified, for example, by substituting the coding sequence for human heavy- and light-chain constant domains in place of homologous murine sequences derived from the hybridoma clone (e.g. as in the method of Morrison et al., *Proc. Natl. Acad. Sci. USA*, 81: 6851–6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

Typically, such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for IFNAR1 and another antigen-combining site having specificity for a different antigen.

Chimeric or hybrid antibodies also can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate.

a. Humanized Antibodies

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. It will be appreciated that variable domain sequences obtained from any non-human animal phage display library-derived Fv clone or from any non-human animal hybridoma-derived antibody clone provided as described herein can serve as the "import" variable domain used in the construction of the humanized antibodies of the invention. Humanization can be essentially performed following the method of Winter and co-workers (Jones et al., Nature, 321: 522 (1986); Riechmann et al., Nature, 332: 323 (1988); Verhoeyen et al., Science, 239: 1534 (1988)), by substituting non-human animal, e.g. rodent, CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human animal, e.g. rodent, antibodies.

The choice of human variable domains, both light and heavy, to be used in making the humanized antibodies is very important to reduce antigenicity. According to the so-called "best-fit" method, the sequence of the variable domain of a non-human animal, e.g. rodent, antibody is screened against the entire library of known human variable-domain sequences. The human sequence that is closest to that of the non-human animal is then accepted as the human framework (FR) for the humanized antibody (Sims et al., J. Immunol., 151: 2296 (1993); Chothia and Lesk, J. Mol. Biol., 196: 901 (1987)). Another method uses a particular framework derived from the consensus sequence of all human antibodies of a particular subgroup light or heavy chains. The same framework can be used for several different humanized antibodies (Carter et al., Proc. Natl. Acad. Sci USA, 89: 4285 (1992); Presta et al., J. Immunol., 151: 2623 (1993)).

It is also important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind to its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

b. Human Antibodies

Human anti-IFNAR1 antibodies of the invention can be constructed by combining Fv clone variable domain sequence(s) selected from human-derived phage display libraries with known human constant domain sequences(s) as described above. Alternatively, human monoclonal anti-IFNAR1 antibodies of the invention can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51–63 (Marcel Dekker, Inc., New York, 1987); and Boerner et al., J. Immunol., 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci USA, 90: 2551 (1993); Jakobovits et al., Nature, 362: 255 (1993); Bruggermann et al., Year in Immunol., 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

c. Bispecific Antibodies

Bispecific antibodies are monoclonal, preferably human or humanized, antibodies that have binding specificities for at least two different antigens. In the present case, one of the binding specificities is for IFNAR1 and the other is for any other antigen. Exemplary bispecific antibodies may bind to two different epitopes of the IFNAR1 protein. Bispecific antibodies may also be used to localize cytotoxic agents to cells that express IFNAR1. These antibodies possess an IFNAR1-binding arm and an arm which binds the cytotoxic agent (e.g saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities(Milstein and Cuello, *Nature*, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.*, 10: 3655 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986). According to another approach, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217–225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5): 1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444–6448 (1993) has provided an alternative mechanism for making bispecific antibody fragments. The fragments comprise a heavy-chain variable domain (VH) connected to a light-chain variable domain (VL) by a linker that is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

IV. Diagnostic Uses of Anti-IFNAR1 Antibodies

The anti-IFNAR1 antibodies of the invention are unique research reagents which provide anti-type I interferon activity templates for use in chemical library screening, wherein the practitioner can use a signal transduction assay as an initial, high volume screen for agents that exhibit an anti-type I interferon activity pattern that is similar to the anti-type I interferon activity pattern of an anti-IFNAR1 antibody of the invention. In this way, candidate agents likely to exhibit a desired type I interferon activity inhibition profile can be obtained with ease, avoiding prohibitively expensive and logistically impossible numbers of type I interferon induced viral inhibition assays or cell proliferation inhibition assays on large chemical libraries.

In one embodiment, the anti-IFNAR1 antibodies of the invention are used to screen chemical libraries in a Kinase Receptor Activation (KIRA) Assay as described in WO 95/14930 (published Jun. 1, 1995). The KIRA assay is suitable for use herein because ligand binding to the type I interferon receptor complex in situ in on the surface of host cells expressing the receptor induces a rapid increase in the phosphorylation of tyrosine residues in the intracellular domains of both IFNAR1 and IFNAR2 components of the receptor as taught in Platanias and Colamonici, *J. Biol. Chem.*, 269: 17761–17764 (1994). The level of tyrosine phosphorylation can be used as a measure of signal transduction. The effect of an anti-IFNAR1 antibody of the invention on the levels of tyrosine phosphorylation induced by various type I interferons in the KIRA assay can be used as a bench mark activity pattern for comparison to the activity patterns generated by the library compounds in the assay.

The KIRA assay suitable for use herein employs a host cell that expresses the type I interferon receptor (both IFNAR1 and IFNAR2 components of the receptor) and the particular series of type I interferons which define the inhibitor profile of interest. Cells which naturally express the human type I interferon receptor, such as the human Daudi cells and U-266 human myeloma cells described in Colamonici and Domanski, *J. Biol. Chem.*, 268: 10895–10899 (1993), can be used. In addition, cells which are transfected with the IFNAR1 and IFNAR2 components and contain intracellular signaling proteins necessary for type I interferon signal transduction, such as mouse L-929 cells as described in Domanski et al., *J. Biol. Chem.*, 270: 21606–21611 (1995), can be used. In the KIRA assay, the candidate antagonist is incubated with each type I interferon ligand to be tested, and each incubation mixture is contacted with the type I interferon receptor-expressing host cells. The treated cells are lysed, and IFNAR1 protein in the cell lysate is immobilized by capture with solid phase anti-IFNAR1 antibody. Signal transduction is assayed by measuring the amount of tyrosine phosphorylation that exists in the intracellular domain (ICD) of captured IFNAR1 and the amount of tyrosine phosphorylation that exists in the intracellular domain of any co-captured IFNAR2. Alternatively, cell lysis and immunoprecipitation can be performed under denaturing conditions in order to avoid co-capture of IFNAR2 and permit measurement of IFNAR1 tyrosine phosphorylation alone, e.g. in a manner similar to the procedure described in Platanias et al., *J. Biol. Chem.*, 271: 23630–23633 (1996). The level of tyrosine phosphorylation can be accurately measured with labeled anti-phosphotyrosine antibody that identifies phosphorylated tyrosine residues.

In another embodiment, a host cell coexpressing IFNAR2 and a chimeric construct containing IFNAR1 fused at its carboxy terminus to an affinity handle polypeptide is used in the KIRA assay. The chimeric IFNAR1 construct permits capture of the construct from cell lysate by use of a solid phase capture agent (in place of an anti-IFNAR1 antibody) specific for the affinity handle polypeptide. In a preferred embodiment, the affinity handle polypeptide is Herpes simplex virus glycoprotein D (gD) and the capture agent is an anti-gD monoclonal antibody as described in Examples 2 and 3 of WO 95/14930.

In this system, the anti-IFNAR1 antibody of the invention that possesses the type I interferon inhibition activity profile of interest is used as a standard for analysis of the tyrosine phosphorylation patterns generated by the members of the chemical library that is screened. The IFNAR1 ICD tyrosine phosphorylation pattern generated by the anti-IFNAR1 antibody standard is compared to the tyrosine phosphorylation patterns produced in the library screen, and patterns found to match that of the anti-IFNAR1 antibody standard identify candidate agents that are likely to have a type I interferon activity inhibition profile similar to that of the anti-IFNAR1antibody standard. Accordingly, the anti-IFNAR1 antibody of the invention provides a useful means to quickly and efficiently screen large chemical libraries for compounds likely to exhibit the particular type I interferon activity inhibition profile of the antibody.

The anti-IFNAR1 antibodies of the invention are useful in diagnostic assays for IFNAR1 expression in specific cells or tissues wherein the antibodies are labeled as described below and/or are immobilized on an insoluble matrix. Anti-IFNAR1 antibodies also are useful for the affinity purification of IFNAR1 from recombinant cell culture or natural sources.

Anti-IFNAR1 antibodies can be used for the detection of IFNAR1 in any one of a number of well known diagnostic assay methods. For example, a biological sample may be assayed for IFNAR1 by obtaining the sample from a desired source, admixing the sample with anti-IFNAR1antibody to allow the antibody to form antibody/IFNAR1 complex with any IFNAR1 present in the mixture, and detecting any antibody/IFNAR1 complex present in the mixture. The biological sample may be prepared for assay by methods known in the art which are suitable for the particular sample. The methods of admixing the sample with antibodies and the methods of detecting antibody/IFNAR1 complex are chosen according to the type of assay used. Such assays include competitive and sandwich assays, and steric inhibition assays. Competitive and sandwich methods employ a phase-separation step as an integral part of the method while steric inhibition assays are conducted in a single reaction mixture.

Analytical methods for IFNAR1 all use one or more of the following reagents: labeled IFNAR1 analogue, immobilized IFNAR1 analogue, labeled anti-IFNAR1 antibody, immobilized anti-IFNAR1 antibody and steric conjugates. The labeled reagents also are known as "tracers." The label used is any detectable functionality that does not interfere with the binding of IFNAR1 and anti-IFNAR1 antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleinmides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., *Nature*, 144: 945 (1962); David et al., *Biochemistry*, 13: 1014–1021 (1974); Pain et al., *J. Immunol. Methods*, 40: 219–230 (1981); and Nygren, *J. Histochem. and Cytochem.*, 30: 407–412 (1982). Preferred labels herein are enzymes such as horseradish peroxidase and alkaline phosphatase.

The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147–166.

Immobilization of reagents is required for certain assay methods. Immobilization entails separating the anti-IFNAR1 antibody from any IFNAR1 that remains free in solution. This conventionally is accomplished by either insolubilizing the anti-IFNAR1 antibody or IFNAR1 analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the anti-IFNAR1 antibody or IFNAR1 analogue afterward, e.g., by immunoprecipitation.

Other assay methods, known as competitive or sandwich assays, are well established and widely used in the commercial diagnostics industry.

Competitive assays rely on the ability of a tracer IFNAR1 analogue to compete with the test sample IFNAR1 for a limited number of anti-IFNAR1 antibody antigen-binding sites. The anti-IFNAR1 antibody generally is insolubilized before or after the competition and then the tracer and IFNAR1 bound to the anti-IFNAR1 antibody are separated from the unbound tracer and IFNAR1. This separation is accomplished by decanting (where the binding partner was preinsolubilized) or by centrifuging (where the binding partner was precipitated after the competitive reaction). The amount of test sample IFNAR1 is inversely proportional to the amount of bound tracer as measured by the amount of marker substance. Dose-response curves with known amounts of IFNAR1 are prepared and compared with the test results to quantitatively determine the amount of IFNAR1 present in the test sample. These assays are called ELISA systems when enzymes are used as the detectable markers.

Another species of competitive assay, called a "homogeneous" assay, does not require a phase separation. Here, a conjugate of an enzyme with the IFNAR1 is prepared and used such that when anti-IFNAR1 antibody binds to the IFNAR1 the presence of the anti-IFNAR1 antibody modifies the enzyme activity. In this case, the IFNAR1 or its immunologically active fragments are conjugated with a bifunctional organic bridge to an enzyme such as peroxidase. Conjugates are selected for use with anti-IFNAR1 antibody so that binding of the anti-IFNAR1 antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small IFNAR1 fragment so that antibody to hapten is substantially unable to bind the conjugate at the same time as anti-IFNAR1 antibody. Under this assay procedure the IFNAR1 present in the test sample will bind anti-IFNAR1 antibody, thereby allowing anti-hapten to bind the conjugate, resulting in a change in the character of the conjugate hapten, e.g., a change in fluorescence when the hapten is a fluorophore.

Sandwich assays particularly are useful for the determination of IFNAR1 or anti-IFNAR1 antibodies. In sequential sandwich assays an immobilized anti-IFNAR1 antibody is used to adsorb test sample IFNAR1, the test sample is removed as by washing, the bound IFNAR1 is used to adsorb a second, labeled anti-IFNAR1 antibody and bound material is then separated from residual tracer. The amount of bound tracer is directly proportional to test sample IFNAR1. In "simultaneous" sandwich assays the test sample is not separated before adding the labeled anti-IFNAR1. A sequential sandwich assay using an anti-IFNAR1 monoclonal antibody as one antibody and a polyclonal anti-IFNAR1 antibody as the other is useful in testing samples for IFNAR1.

The foregoing are merely exemplary diagnostic assays for IFNAR1. Other methods now or hereafter developed that use anti-IFNAR1 antibody for the determination of IFNAR1 are included within the scope hereof, including the bioassays described above.

V. Therapeutic Compositions and Administration of Anti-IFNAR1 Antibodies

Therapeutic formulations of the anti-IFNAR1 antibodies of the invention are prepared for storage by mixing antibody having the desired degree of purity with optional physiologically acceptable carriers, excipients, or stabilizers (*Remington: The Science and Practice of Pharmacy*, 19th Edition, Alfonso, R., ed, Mack Publishing Co. (Easton, Pa.: 1995)), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The anti-IFNAR1 antibody to be used for in vivo administration must be sterile. This is readily accomplished by filtration through sterile filtration membranes, prior to or following lyophilization and reconstitution. The anti-IFNAR1 antibody ordinarily will be stored in lyophilized form or in solution.

Therapeutic anti-IFNAR1 antibody compositions generally are placed into a container having a sterile access port, for example, an intravenous solution bag or vial having a stopper pierceable by a hypodermic injection needle.

The route of anti-IFNAR1 antibody administration is in accord with known methods, e.g. injection or infusion by intravenous, intraperitoneal, intracerebral, subcutaneous, intramuscular, intraocular, intraarterial, intracerebrospinal, or intralesional routes, or by sustained release systems as noted below. Preferably the antibody is given systemically.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers*, 22: 547–556 (1983)), poly (2-hydroxyethyl-methacrylate) (Langer et al., *J. Biomed. Mater. Res.*, 15: 167–277 (1981) and Langer, *Chem. Tech.*, 12: 98–105 (1982)), ethylene vinyl acetate (Langer et al., supra) or poly-D-(-)-3-hydroxybutyric acid (EP 133,988). Sustained-release anti-IFNAR1 antibody compositions also include liposomally entrapped antibody. Liposomes containing antibody are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal antibody therapy.

Anti-IFNAR1 antibody can also be administered by inhalation. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-IFNAR1 antibody can be aerosolized using a fluorocarbon formulation and a metered dose inhaler, or inhaled as a lyophilized and milled powder.

An "effective amount" of anti-IFNAR1 antibody to be employed therapeutically will depend, for example, upon the therapeutic objectives, the route of administration, the type of anti-IFNAR1 antibody employed, and the condition of the patient. Accordingly, it will be necessary for the therapist to titer the dosage and modify the route of administration as required to obtain the optimal therapeutic effect. Typically, the clinician will administer the anti-IFNAR1 antibody until a dosage is reached that achieves the desired effect. The progress of this therapy is easily monitored by conventional assays.

The patients to be treated with the anti-IFNAR1 antibody of the invention include preclinical patients or those with recent onset of immune-mediated disorders, and particularly autoimmune disorders. Patients are candidates for therapy in accord with this invention until such point as no healthy tissue remains to be protected from immune-mediated destruction. For example, a patient suffering from insulin-dependent diabetes mellitus (IDDM) can benefit from therapy with an anti-IFNAR1 antibody of the invention until the patient's pancreatic islet cells are no longer viable. It is desirable to administer an anti-IFNAR1 antibody as early as possible in the development of the immune-mediated or autoimmune disorder, and to continue treatment for as long as is necessary for the protection of healthy tissue from destruction by the patient's immune system. For example, the IDDM patient is treated until insulin monitoring demonstrates adequate islet response and other indicia of islet necrosis diminish (e.g. reduction in anti-islet antibody titers), after which the patient can be withdrawn from anti-IFNAR1antibody treatment for a trial period during which insulin response and the level of anti-islet antibodies are monitored for relapse.

In the treatment and prevention of an immune-mediated or autoimmune disorder by an anti-IFNAR1 antibody, the antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners. The "therapeutically effective amount" of antibody to be administered will be governed by such considerations, and is the minimum amount necessary to prevent, ameliorate, or treat the disorder, including treating chronic autoimmune conditions and immunosuppression maintenance in transplant recipients. Such amount is preferably below the amount that is toxic to the host or renders the host significantly more susceptible to infections.

As a general proposition, the initial pharmaceutically effective amount of the antibody administered parenterally will be in the range of about 0.1 to 50 mg/kg of patient body weight per day, with the typical initial range of antibody used being 0.3 to 20 mg/kg/day, more preferably 0.3 to 15 mg/kg/day. The desired dosage can be delivered by a single bolus administration, by multiple bolus administrations, or by continuous infusion administration of antibody, depending on the pattern of pharmacokinetic decay that the practitioner wishes to achieve.

As noted above, however, these suggested amounts of antibody are subject to a great deal of therapeutic discretion. The key factor in selecting an appropriate dose and scheduling is the result obtained, as indicated above.

The antibody need not be, but is optionally formulated with one or more agents currently used to prevent or treat the immune-mediated or autoimmune disorder in question. For example, in rheumatoid arthritis, the antibody may be given in conjunction with a glucocorticosteroid. The effective amount of such other agents depends on the amount of anti-IFNAR1 antibody present in the formulation, the type of disorder or treatment, and other factors discussed above. These are generally used in the same dosages and with administration routes as used hereinbefore or about from 1 to 99% of the heretofore employed dosages.

Further details of the invention can be found in the following example, which further defines the scope of the invention. All references cited throughout the specification, and the references cited therein, are hereby expressly incorporated by reference in their entirety.

EXAMPLE

Materials and Methods

Preparation of Soluble IFNAR1-IgG.

A cDNA encoding the human immunoglobulin fusion proteins (immunoadhesins) based on the ECD of the hIFNAR1 (pRK5 hIFNAR1-IgG clone 53.65) was generated using methods similar to those described by Haak-Frendscho et al., *Immunology* 79: 594–599 (1993) for the construction of a murine IFN-γ receptor immunoadhesin. Briefly, the plasmid $pRKCD4_2Fc_1$ was constructed as described in Example 4 of WO 89/02922 (PCT/US88/03414 published Apr. 6, 1989). The cDNA coding sequence for the 404 amino acid ECD of mature hIFNAR1 shown in FIG. 7 was obtained from the published sequence (Uze et al., *Cell*, 60: 225–234 (1990)). The CD4 coding sequence in the $pRKCD4_2Fc_1$ was replaced with the hIFNAR1 ECD encoding cDNA to form pRK5hIFNAR1-IgG clone 53.65. The nucleic acid sequence (SEQ ID NO. 21) and amino acid sequence (SEQ ID NO. 22) for the hIFNAR1 ECD-IgG encoding insert of clone 53.65 are shown in FIG. 7. hIFNAR1-IgG was expressed in human embryonic kidney 293 cells by transient transfection using a calcium phosphate precipitation technique. The immunoadhesin was purified from serum-free cell culture supernatants in a single step by affinity chromatography on a protein A-sepharose column as described in Haak-Frendscho et al. (1993), supra. Bound hIFNAR1-IgG was eluted with 0.1 M citrate buffer, pH 3.0, containing 20% (w/v) glycerol. The hIFNAR1-IgG purified was >95% pure, as judged by SDS-PAGE.

Production of hIFN-α Subtypes.

Standard cloning procedures described in Maniatis et al., *Molecular Cloning: A Laboratory Manual*, Cold Spring Harbor Laboratory Press, Cold Spring Harbor, N.Y. (1989) were used to construct plasmids that direct the translocation of the various species of hIFN-α into the periplasmic space of *E. coli*. PCR reactions were performed on cDNA clones of the various subspecies of hIFN-α disclosed in Goeddel et al., *Nature* 290: 20–26 (1981) with NsiI and StyI restriction sites added to the primers. These PCR products were then subcloned into the corresponding sites of the expression vector pB0720 described in Cunningham et al., *Science* 243:1330–1336 (1989). The resulting plasmids placed production of the hIFN-α subtypes under control of the *E. coli* phoA promoter and the heat-stable enterotoxin II signal peptide as described in Chang et al., *Gene* 55: 189–196 (1987). The correct DNA sequence of each gene was confirmed using the United States Biochemical Sequenase Kit version 2.0. Each plasmid was transformed into the *E. coli* strain 27C7 (ATCC #55244) and grown in 10 liter fermentors as described in Carter et al., *Bio/Technology* 10: 163–167 (1992). Human hIFNs were purified from *E. coli* paste containing each IFN-α by affinity chromatography. Bacterial cells were lysed, and the lysate was centrifuged at 10,000×g to remove debris. The supernatant was applied to an immunoaffinity column containing a mouse anti-hIFN-αB antibody (LI-1) that was obtained as described in Staehelin et al., *Proc. Natl. Acad Sci*. 78:1848–1852 (1981). LI-1 was immobilized on controlled pore glass by a modification of the method of Roy et al., *Journal of Chromatography*, 303: 225–228 (1984). The bound interferon was eluted from the column with 0.1 M citrate, pH 3.0, containing 20% (w/v) glycerol. The purified IFN was analyzed by SDS-PAGE and immunoblotting, and was assayed for bioactivity by the hIFN-induced anti-viral assay as described herein. hIFNβ was obtained from Sigma (St. Louis, Mo.) and IFN-α1/2 was obtained as described in Rehberg et al., *J. Biol. Chem.*, 257: 11497–11502 (1992) or Horisberger and Marco, *Pharmac. Ther.*, 66: 507–534 (1995).

Generation of mAbs to hIFNAR1.

Balb/c mice were immunized into each hind foot pad 11 times at two week intervals, with 2.5 μg of hIFNAR1-IgG fusion protein resuspended in MPL-TDM (Ribi Immunochem. Research Inc., Hamilton, Mont.). Three days after the final boost, popliteal iymph node cells were fused with murine myeloma cells, P3X63AgU.1 (ATCC CRL1597), using 35% polyethylene glycol. Hybridomas were selected in HAT medium. Ten days after the fusion, hybridoma culture supernatants were first screened for mAbs binding to the hIFNAR1-IgG fusion protein in a capture ELISA. The selected culture supernatants were then tested by flow cytometric analysis for their ability to recognize the hIFNAR1 on U266 cells as described in Chuntharapai et al., *J. Immunol.*, 152:1783–1789 (1994). The blocking mAbs were selected for their ability to inhibit the anti-viral cytopathic effect of IFN as described below.

The affinities of these mAbs were determined in a competitive binding radioimmunoprecipitation assay according to the method of Kim et al., *J. Immunol. Method*, 156: 9–17 (1992). Briefly, $^{125}$I-hIFNAR1-IgG (specific activity 11.6 μCi/μg) was prepared using a lactoperoxidase labeling method. mAbs were allowed to bind to $^{125}$I-hIFNAR1-IgG in the presence of various concentrations of unlabeled hIFNAR1-IgG for 1 hour at room temperature (RT). These mixtures were then incubated with goat anti-mouse IgG for 1 hour at RT in the presence of 5% human serum. The immune complexes were then precipitated by the addition of cold 6% polyethylene glycol (MW 8,000) followed by centrifugation at 200×g for 20 minutes at 4° C. Supernatants were removed and the radioactivity remaining in the pellet was determined using a gamma counter. The affinity of each mAb was determined according to the method of Munson et al., *Anal. Biochem*. 107: 220–239 (1980).

Capture ELISA.

Microtiter plates (Maxisorb; Nunc, Kamstrup, Denmark) were coated with 50 μl/well of 2 μg/ml of goat antibodies specific to the Fc portion of human IgG (Goat anti-hIgG-Fc, Cappel), in PBS, overnight at 4° C. and blocked with 2% BSA for 1 hour at room temperature. After washing the plates, 50 μl/well of 2 μg/ml of IFNAR1-IgG (or IFNAR1-IgG mutant) was added, and plates were incubated for 1 hour. After washing the plates, the remaining anti-Fc binding sites were blocked with PBS containing 3% human serum and 10 μg/ml of CD4-IgG for 1 hour. After washing, plates were then incubated with 50 μl/well of 2 μg/ml of anti-IFNAR1 mAbs (or hybridoma culture supernatants) for 1 hour. After washing, plates were then incubated with 50 μl/well of HRP-Goat anti-mouse IgG. The bound enzyme was detected by the addition of the substrate and the plates were read at 490 nM with an ELISA plate reader. Between each step, plates were washed in wash buffer (PBS containing 0.05% Tween 20).

During the IFNAR1-IgG mutant analysis, the concentrations of immunoadhesin molecules in 293 transfected culture supernatants were determined using CD4-IgG as a standard and were adjusted to be equal to the lowest concentration of immunoadhesin molecules. The degree of mAb binding to these mutants were then compared to the wild type of the same concentration.

Western Blot.

Reduced hIFNAR1 was prepared by treating the hIFNAR1-IgG fusion protein with 5 mM of 2-mercaptoethanol at 95° C. for 5 minutes. The ability of the mAbs to bind to the native and reduced hIFNAR1-IgG was determined by immunoblotting using 12% SDS-PAGE as described in Kim et al., *J. Immunol. Method* 156: 9–17 (1992).

Epitope Mapping Using a Competitive Binding ELISA.

To determine whether the mAbs recognized the same or different epitopes, a competitive binding ELISA was performed as described in Kim et al., (1992), supra, using biotinylated mAbs (Bio-mAb). mAbs were biotinylated using N-hydroxyl succinimide as described in *Antibodies (A Laboratory Manual)*, Harlow, E. and Lane, D., eds, Cold Spring Harbor (1988), p. 341. Microtiter wells were coated with 50 μl of Goat anti-hIgG-Fc and kept overnight at 4° C., blocked with assay buffer for 1 hour, and incubated with 25 Al/well of IFNAR1-IgG (1 μg/ml) for 1 hour at room temperature. After washing microtiter wells, a mixture of a predetermined optimal concentration of Bio-mAb and a thousand-fold excess of unlabeled mAb was added into each well. Following 1 hour incubation at room temperature, plates were washed and the amount of Bio-mAb was detected by the addition of HRP-streptavidin. After washing the microtiter wells, the bound enzyme was detected by the addition of the substrate, and the plates were read at 490 nm with an ELISA plate reader.

Electrophoretic Mobility Shift Assay (EMSA)

Briefly, α-IFNs (25 ng/ml) plus various concentrations (5–500 μg/ml) of anti-hIFNAR1 mAbs were incubated with 5x105 Hela cells in 200 μl of DMEM for 30 minutes at 37° C. Cells were washed in PBS and resuspended in 125 μl of buffer A (10 mM HEPES, pH 7.9, 10 mM KCL, 0.1 mM ETDA, 1 mM DTT, 1 mM phenylmethylsulfonyl fluoride, 10 μg/ml leupeptin, 10 μg/ml aprotinin) as described in Kurabayashi et al., *Mol. Cell Biol.*, 15: 6386 (1995). After a 15 minute incubation on ice, cells were lysed by the addition of 0.025% NP40. The nuclear pellet was obtained by centrifugation and was resuspended in 50 μl of buffer B (20 mM HEPES, pH 7.9, 400 mM NaCl, 0.1 mM EDTA, 1 mM DTT, 1 mM phenylmethylsulfonyl fluoride, 10 μg/ml leupeptin, 10 μg/ml aprotinin) and incubated on ice for 30 minutes. The nuclear fraction was clarified by centrifugation and the supernatant stored at −70° C. until use. Double-stranded probes were prepared from single-stranded oligonucleotides (ISG 15 top: 5'-GATCGGGAAAGGGAAACCGAAACTGAAGCC-3' (SEQ ID NO:23)), ISG115 bottom: 5'-GATCGGCTTCAGTTTCGGTTTCCCTTTCCC-3' (SEQ ID NO:24)) utilizing a DNA polymerase I Klenow fill-in reaction with $^{32}$P-dATP (3,000 Ci/mM, Amersham). Labeled oligonucleotides were purified from unincorporated radioactive nucleotides using BIO-Spin 30 columns (Bio-Rad). Binding reactions, containing 5 μl of nuclear extract, 25,000 cpm of labeled probe and 2 μg of non-specific competitor poly (dI-dC)-poly (dI-dC) in 15 μl of binding buffer (10 mM Tris-HCL, pH 7.5, 50 mM NaCl, 1 mM EDTA, 1 mM DTT, 1 mM phenylmethylsulfonyl fluoride and 15% glycerol) were incubated at room temperature for 30 minutes. DNA-protein complexes were resolved in 6% non-denaturing polyacrylamide gels (Novex) and analyzed by autoradiography. The specificity of the assay was determined by the addition of 350 ng of unlabeled ISG15 probe in separate reaction mixtures. Formation of an ISGF3 specific complex was confirmed by a super shift assay with anti-STAT1 antibody.

Assay for hIFN-α Induced Anti-viral Activity.

The assay was done as described in *Current Protocols in Immunol.*, Coligan, J. E., Kruisbeek, A. M., Margulies, D. H., Shevach, E. M., and Strober, W., eds, Greene Publishing Associates and Wiley-Interscience (1992), Vol. 1, Unit 6.9.1, using the human lung carcinoma cell line A549 challenged with encephalomyocarditis virus (EMC). Briefly, A549 cells seeded at 2x10$^5$ cells/100 μl were grown in DMEM containing 2 mM glutamine, antibiotics, and 5% FCS for 24 hours. Serial dilutions of mAbs in 50 μl DMEM were incubated with various units of type 1 IFNs in 50 μl DMEM for 1 hour at 37° C. These mixtures were then incubated with A549 cells (5x10$^5$ cells/100 μl of DMEM containing 4% FCS) for another 24 hours. Culture supernatants were removed and cells were challenged with 2x10$^5$ pfu of EMC virus in 100 μl for an additional 24 hours. At the end of the incubation, cell viability was determined by visual microscopic examination. The neutralizing antibody titer (EC50) was defined as the concentration of antibody that neutralizes 50% of the anti-viral cytopathic effect by 10 unit/ml of type 1 IFNs. The units of type 1 IFNs used in this study were determined using NIH reference recombinant human IFN-α2 (IFN-αA) as a standard. The specific activities of the various type 1 IFNs utilized were IFN-α2/1 (2x10$^7$ IU/mg), IFN-α1 (3x10$^7$ IU/mg), IFN-α2 (2x10$^7$ IU/mg), IFN-α5 (8x10$^7$ IU/mg), IFN-α8 (19x10$^7$ IU/mg) and IFN-β (1.5x 10$^5$ IU/mg).

Generation of Domain 1-IgG, Domain 2-IgG and Various Mutants to the hIFNAR1.

The cDNAs encoding domain 1 (I-200 residues) and domain 2 (204–404 residues) of IFNAR1 were separately constructed and expressed as immunoadhesins.

Single alanine substitution mutants were generated according to the method of Kunkel et al., *Methods Enzymol.* 154: 367–414 (1987), and Hebert et al., *J. Biol. Chem.*, 268: 18549–18553 (1993). The plasmid DNA was isolated using an RPM Kit (BIO 101 Inc., La Jolla, Calif.) and was sequenced by the Sanger method using an ABI 373A DNA sequencer to verify the mutation. Mutant receptor-IgGs were expressed transiently in human 293 cells as described above. Transfected 293 cells were grown overnight in F-12:DMEM (50:50) containing 10% FCS, 2 mM glutamine, 100 μg/ml of penicillin, 100 μg/ml of streptomycin, 10 μg/ml of glycine, 15 μg/ml of hypoxanthine, and 5 μg/ml of thymidine, and then were placed in serum-free media. Three days later, culture supernatants were collected and used in a capture ELISA. For the hIFNAR1-IgG mutant analysis, the concentrations of immunoadhesin molecules in 293 transfected culture supernatants were determined using CD4-IgG as a standard and were adjusted to be equal to the lowest concentration of immunoadhesin molecules. The degree of mAb binding to these mutants was then compared to the wild type of the same concentration.

RESULTS mAb Binding to Different Sites on hIFNAR1.

Five anti-hIFNAR1 mAbs (2E1, 2E8, 2H6, 4A7, and 5A8) producing hybridomas (generated as described above) that exhibited different binding epitopes and blocking activities described below were selected for further characterization. All of these mAbs are of the IgG2a isotype and recognized the IFNAR1 expressed on U266 human myeloma cells as determined by FACS analysis (Table I below). Western blot analysis determined that only mAbs 2H6, 4A7, and 5A8 bind to the reduced IFNAR1 as shown in Table I below. This indicated that mAbs 2E1 and 2E8 recognize conformational epitopes while mAbs 2H6, 4A7, and 5A8 recognize linear epitopes. The dissociation constants of these mAbs for IFNAR1-IgG were determined to be in the range of 52–3,120 pM as shown in Table I below, as determined by competitive radioimmunoprecipitation followed by Scatchard analysis.

TABLE I

General Characteristics of mAbs to hIFNAR1

| mAbs | FACS[a] | Immunoblot[b] | Kd$^{-1}$ (pM)[c] | epitope[d] | Blocking act.[e] |
|------|---------|---------------|-------------------|------------|------------------|
| 2E1  | ++      | −             | 66                | A1         | α2/1, α1, α2, α5, α8 |
| 2E8  | ++      | −             | 97                | A2         | None             |
| 2H6  | ++      | +             | 3120              | B          | None             |
| 4A7  | ++      | +             | 52                | C          | α2/1, α1, α2, α5, α8 |
| 5A8  | ++      | +             | 174               | D          | α8[f]            |

[a]. FACS staining was done using the human myeloma cell line U266.
[b]. The immunoblot was performed using reduced hIFNAR1.
[c]. The affinities of these mAbs for soluble hIFNAR1-IgG were determined by Scatchard analysis.
[d]. The epitopes recognized by these mAbs as determined by competitive binding ELISA were named arbitrarily.
[e]. Summary of results from anti-viral assay and ISGF3 EMSA.
[f]. The blocking activity was observed only in the EMSA.

To determine whether each mAb recognizes the same or different epitopes, competitive binding ELISAs were performed to detect the binding of each biotinylated mAb in the presence of excess unlabeled mAb. The results from the competitive binding ELISA (shown in FIG. 2) determined that these five mAbs could detect four different epitopes on IFNAR1. mAbs 2E1 and 2E8 can compete with each other, which indicates that they recognize the same or an overlapping epitope.

Ability of mAbs to Block Type 1 IFN Activity.

Figure 3:
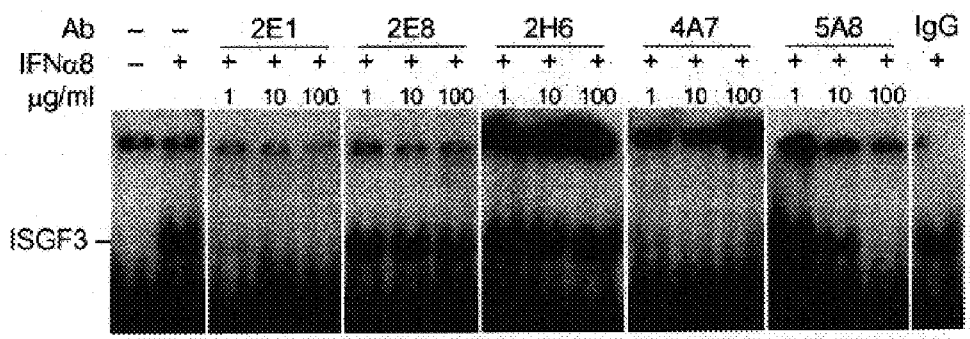
FIG. 3 is a collection of autoradiographs depicting the effect of mAbs 2E1, 2E8, 2H6, 4A7 and 5A8 on ISGF3 formation in Hela cells induced by IFN-α8 (IFN-αB) in an electrophoretic mobility shift assay (EMSA).

The blocking activities of mAbs to hIFNAR1 were determined using an ISGF3 electrophoretic mobility shift assay (EMSA) as well as an anti-viral assay. Type 1 IFNs induce the transcription of interferon-stimulated genes through the formation and activation of IFN-stimulating response element (ISRE) binding proteins. One of these binding proteins is ISGF3 which is a multi-subunit protein complex formed in the cytoplasm within minutes of type 1 IFN treatment (Schindler et al., Proc. Natl. Acad. Sci. (USA), 89: 7836 (1997); Fu et al., Proc. Natl. Acad. Sci. (USA), 89: 7840 (1997)). By investigating ISGF3 formation in Hela cells induced by the addition of 25 ng/ml of several human type 1 IFNs (IFN-α2/1, -α1, -α2, -α5, -α8 and IFN-β), the blocking activities of mAbs were detected in the range of 5–500 μg mAb/ml. FIG. 3 contains representative autoradiographs depicting ISGF3 formation induced by hIFN-α8 (IFN-αD). mAbs 2E1 and 4A7 inhibited ISGF3 formation induced by IFN-α8 at a concentration of 5 μg mAb/ml; mAb 5A8 completely inhibited the activity of IFN-α8 at a concentration of 500 μg mAb/ml and partially inhibited the activity of IFN-α8 at a concentration of 50 μg mAb/ml; mAbs 2E8 and 2H6 were unable to block the activity of IFN-α8. Results obtained with all type 1 IFNs tested are summarized in Table II below. Although there is some variation in the potency of blocking activities of mAbs 2E1 and 4A7 depending upon the subspecies of IFN-α, mAbs 2E1 and 4A7 inhibited the activities of all IFN-αs tested and mAb 2E1 was a more potent inhibitor. At a concentration of 500 μg mAb/ml, mAb 5A8 showed blocking activity on IFN-α8 and partial blocking activities on -α2/1 and -α2. mAbs 2E8 and 2H6 showed no blocking activity on any of these hIFN-αs. None of these mAbs to hIFNAR1 were able to block ISGF3 formation induced by IFN-β.

TABLE II

Effects of anti-hIFNAR1 mAbs on ISGF3 formation induced by type 1 IFNs

| Ab | μg/ml | IFNα2/1 | IFNα1 | IFNα2 | IFNα5 | IFNα8 | IFNβ |
|---|---|---|---|---|---|---|---|
| 2E1 | 5 | − | − | + | − | + | − |
|  | 50 | + | + | + | +/− | + | − |
|  | 500 | + | + | + | + | + | − |
| 2E8 | 5 | − | − | − | − | − | − |
|  | 50 | − | − | − | − | − | − |
|  | 500 | − | − | − | − | − | − |
| 2H6 | 5 | − | − | − | − | − | − |
|  | 10 | − | − | − | − | − | − |
|  | 100 | − | − | − | − | − | − |
| 4A7 | 5 | − | − | +/− | − | + | − |
|  | 50 | + | +/− | +/− | − | + | − |
|  | 500 | + | + | + | +/− | + | − |
| 5A8 | 5 | − | − | − | − | − | − |
|  | 50 | − | − | − | − | +/− | − |
|  | 500 | +/− | − | +/− | − | + | − |
| IgG | 5 | − | − | − | − | − | − |

ISGF3 EMSA was carried out using Hela cells treated with 25 ng/ml of IFNs plus 5–500 μg/ml of mAbs for 30 min. Results were expressed as complete blocking (+), partial blocking (+/−) and no blocking (−). A typical autoradiograph is shown in FIG. 2.

The neutralizing effect of these mAbs was also characterized by anti-viral assays (Table III below). Assays were done using serial dilutions of mAbs in the range of 0.1 to 30 μg mAb/ml and 10 units/ml of type 1 IFNs. The units of these IFNs were determined using NIH IFN-α2 (IFN-αA) as a standard. mAb 2E1 and mAb 4A7 blocked the activity of all IFN-αs. Abs 2E8, 2H6 and 5A8 showed no neutralizing activities in the anti-viral assay. None of these mAbs were able to neutralize the effect of IFN-β. Similar results were obtained using 100 units/ml of type 1 IFNs. Overall, the results obtained in the anti-viral assay correlated well with the results obtained in the EMSA assay.

TABLE III

Effects of anti-hIFNAR1 mAbs on the anti-viral effects of type 1 IFNs

| | EC50 of mAb (μg/ml) | | | | | |
|---|---|---|---|---|---|---|
| mAb | IFNα2/1 | IFNα1 | IFNα2 | IFNα5 | IFNα8 | IFNβ |
| 2E1 | 3 | 3 | 1 | 1 | 1 | NB |
| 2E8 | NB | NB | NB | NB | NB | NB |
| 2H6 | NB | NB | NB | NB | NB | NB |
| 4A7 | 20 | 10 | 10 | 6 | 3 | NB |
| 5A8 | NB | NB | NB | NB | NB | NB |

The neutralizing antibody titer (EC50) was defined as the concentration of antibody which neutralizes 50% of the anti-viral cytopathic effects induced by 10 units/ml of type 1 IFNs on A549 cells. The experiment was done using serial dilutions of mAbs in the range of 0.1–30 μg/ml in duplicate. mAbs found to exhibit no blocking effect at a concentration of 30 μg/ml in this assay were designated as nonblocking mAb (NB).

From the results of the ISGF3 formation assays (Table II) and the anti-viral assay (Table III), it was determined that mAbs 2E1 and 4A7 are blocking mAbs against all the IFN-αs tested, mAb 5A8 is a very weak blocking mAb, and mAbs 2E8 and 2H6 are nonblocking mAbs. None of these mAbs was able to block the activity of hIFN-β.

Both Domain 1 and 2 of the IFNAR1 May be Required for IFN Signaling.

Domain 1 (residues 1–200) and domain 2 (residues 204–404) of IFNAR1 were expressed separately as immunoadhesins, as shown in FIG. 4, and the binding capacity of the blocking mAbs was determined against the domain 1 and domain 2 adhesin molecules in a capture ELISA. The concentrations of domain 1-IgG and domain 2-IgG in the culture supernatant were determined by comparison to the known concentrations of CD4-IgG in an ELISA. mAbs 2H6 and 4A7 bound only to domain 1-IgG. mAb 5A8 bound to both domain 1-IgG and domain 2-IgG, while mAbs 2E1 and 2E8 were unable to bind to either of these domain-IgGs as shown in FIG. 5. These results indicate that three out of five mAbs bound to domain 1, and implicate the participation of domain 1 in IFN signaling. Also, mAbs 2E1 and 2E8 were determined to recognize conformational epitopes composed of regions in both domains 1 and 2, implicating the participation of both domains in the IFN signaling.

Determination of mAb Binding to Alanine Substitution Mutants of the hIFNAR1.

To define areas of IFNAR1 which play an important role in mAb binding, multiple alanine substitution mutants in the hydrophilic regions of IFNAR1 were generated. Residues 19–25, 69–74, 76–80, 103–111, 148–152, 157–162, 244–249, 291–298, 352–359, and 383–388 were selected for mutagenesis as shown in FIG. 4. After adjusting the concentrations (30–100 ng/ml) of the IFNAR1-IgG mutants in the culture supernatants of 293 transfectants to be equivalent, the binding abilities of the mAbs to these mutants were determined in a capture ELISA. The results shown in Table IV below were obtained using mAbs at a concentration of 10 μg/ml in the capture ELISA. The binding capacity of the most potent blocking mAb, 2E1, was significantly reduced or almost undetectable when the hydrophilic amino acids in residues 69–74 (domain 1), 244–249 (domain 2) or 291–298 (domain 2) were substituted with alanines as shown in Table 2 below. The binding to the alanine mutant of residues 69–74 was significantly reduced with all mAbs except mAb 5A8. The binding of mAb 5A8 to this mutant was 67% of binding to the wild type. Since mAb 5A8 was shown to bind to domain 1-IgG and domain 2-IgG separately (FIG. 6), some of the 67% binding to this 69–74 mutant by mAb 5A8 is believed to be due to binding with domain 2. Thus, the alanine substitution of residues 69–74 affected the binding of all mAbs, indicating that some structural change occurs in this portion of the receptor which interferes with the interaction between mAbs 2E1 and 2E8 and IFNAR1.

TABLE IV

The binding of mAbs to IFNAR1 multiple alanine mutants

| | | % wild type binding of mAbs | | | | |
|---|---|---|---|---|---|---|
| Mutant | Alanine substitution | 2E1 | 2E8 | 2H6 | 4A7 | 5A8 |
| 1 | 19–25 (RWNRSDE (SEQ ID NO. 1)-AWNASAA (SEQ ID NO. 2)) | 101 | 84 | 77 | 95 | 110 |
| 2 | 69–74 (EEIKLR (SEQ ID NO. 3)-AAIALA (SEQ ID NO. 4)) | 21 | 18 | 0 | 0 | 67 |
| 3 | 76–80 (RAEKE (SEQ ID NO. 5)-AAAAA (SEQ ID NO. 6)) | 97 | 69 | 48 | 92 | 109 |
| 4 | 103–111 (EVHLEAEDK (SEQ ID NO. 7)-AVALAAAAA (SEQ ID NO. 8)) | 66 | 33 | 39 | 80 | 34 |
| 5 | 148–152 (EERIE (SEQ ID NO. 9)-AAAIA (SEQ ID NO. 10)) | 87 | 43 | 68 | 90 | 80 |
| 6 | 157–162 (RHKIYK (SEQ ID NO. 11)-AAAIYA (SEQ ID NO. 12)) | 84 | 77 | 90 | 100 | 100 |
| 7 | 244–249 (HLYKWK (SEQ ID NO. 13)-ALYAWA (SEQ ID NO. 14)) | 0 | 77 | 105 | 106 | 110 |
| 8 | 291–298 (EEIKFDTE (SEQ ID NO. 15)-AAIAFATA (SEQ ID NO. 16)) | 6 | 0 | 64 | 96 | 75 |
| 9 | 352–359 (ERKIIEKK (SEQ ID NO. 17)-AAAIIAAA (SEQ ID NO. 18)) | 105 | 81 | 101 | 101 | 81 |
| 10 | 383–388 (DEKLNK (SEQ ID NO. 19)-AAALNA (SEQ ID NO. 20)) | 105 | 116 | 93 | 103 | 83 |

The level of binding determined in a capture ELISA.
The % binding was calculated by dividing the binding O.D. to each mutant-IgG by the binding O.D. to the wild type IFNAR1-IgG.

To determine which residues were important for the mAb binding in residues 69–74, 244–249, and 291–298, single alanine mutants were generated and examined for their ability to bind to mAbs in capture ELISA as described above. The results of these binding studies are shown in Table V below. In domain 1, Arg74 was determined to be the crucial residue for the binding of mAb 2H6. In domain 2, residues Glu291 and Asp296 were determined to play important roles in the binding of mAbs 2E1 and 2E8. In addition, Lys249 was also found to be important for the binding of mAb 2E1.

TABLE V mAb binding to IFNAR1 single alanine mutants

| | | % Wild type binding of mAbs | | | | |
|---|---|---|---|---|---|---|
| area | mutant | 2E1 | 2E8 | 2H6 | 4A7 | 5A8 |
| AA 69–74 | E69A | 72 | 72 | 64 | 69 | 91 |
| | E70A | 81 | 80 | 79 | 85 | 83 |
| | K72A | 90 | 89 | 89 | 91 | 110 |
| | R74A | 57 | 53 | 0 | 30 | 84 |
| AA 244–249 | H244A | 92 | 96 | 94 | 96 | 99 |
| | K247A | 74 | 66 | 88 | 86 | 93 |
| | K249A | 5 | 54 | 69 | 73 | 71 |
| AA 291–298 | E291A | 7 | 3 | 49 | 58 | 61 |
| | E292A | 34 | 29 | 55 | 58 | 66 |
| | K294A | 54 | 54 | 65 | 69 | 82 |
| | D296A | 5 | 3 | 49 | 53 | 70 |
| | E298A | 36 | 31 | 53 | 60 | 72 |

Inhibition of mAb Binding to Membrane hIFNAR1 by Soluble hIFNAR1-IgG.

The above-described epitope mapping studies were performed with soluble receptor proteins. In order to demonstrate that the binding of these mAbs to a soluble hIFNAR1-IgG reflects the behavior of the ECD displayed by a membrane associated hIFNAR1, the ability of mAbs to bind membrane hIFNAR in the presence of soluble hIFNAR-IgGs was determined. Fluoresceinated (F-) mAbs were incubated with wild type or mutant soluble hIFNAR1-IgGs at room temperature for 30 minutes. These mixtures were then added to U266 human myeloma cells. After incubation at 4° C. for 30 minutes, cells were washed and analyzed by FACS. In the presence of wild type hIFNAR1-IgG, the binding of F-2E1 to U266 cells was completely inhibited as shown in Table VI below.

TABLE VI

Inhibition of mAb binding to U266 cells by soluble hIFNAR1-IgG mutants as determined by Flow Cytometry

| | Mean Fluorescence Intensity | | | |
|---|---|---|---|---|
| soluble hIFNAR1 | F-2E1 | F-2E8 | F-4A7 | F-IgG |
| None | 7.60 | 7.96 | 9.49 | 2.99 |
| wild type | 2.83 | 3.16 | 2.45 | — |
| Mutant #7 | 7.82 | 3.27 | 2.95 | — |
| Mutant #8 | 7.65 | 7.60 | 3.16 | — |

Fluoresceinated mAbs (1 µg/100 µl) were incubated with 10 µg of soluble hIFNAR1-IgGs for 30 minutes at room temperature. These mixtures were then added to U266 cells ($10^5$ cells/25 µl) and incubated for 30 minutes at 4° C. After washing, cells were analyzed by FACScan. Mutant #7 and mutant #8 have multiple alanine substitutions at residues 244–249 (HLYKWK-ALYAWA) and residues 291–298 (EEIKFDTE-AAIAFATA) as shown in Table IV.

The same results were obtained with mAbs F-2E8 and F-4A7. These results demonstrated that wild type soluble hIFNAR1 can effectively inhibit the mAb binding to membrane hIFNAR1 on U266 cells and indicated that the structure of the soluble hIFNAR1-IgG indeed mimics the structure of the ECD of membrane hIFNAR1. In addition, inhibition experiments were performed with soluble hIFNAR1-IgG mutants (designated as Mutants #7 and #8 in Table IV). As expected, soluble mutant #7 (alanine substitutions in residues 244–249) inhibited the binding of mAbs F-2E8 and F-4A7 but did not inhibit the binding of F-2E1 while soluble mutant #8 (alanine substitutions in residues 291–298) inhibited the binding of mAbs F-4A7 but did not inhibit the binding of F-2E1 and F-2E8. From these results, it was determined that the soluble and membrane bound IFNAR1 epitopes recognized by mAb 2E1 include residues 244–249 and 291–298 and the soluble and membrane bound IFNAR1 epitopes recognized by mAb 2E8 include residues 291–298.

Discussion

The results obtained in these studies demonstrated that both domain 1 and domain 2 of hIFNAR1 are necessary to mediate an IFN-α signal. First, the blocking mAb 4A7 bound to the domain 1-IgG, which indicated the participation of domain 1 in IFN signaling. Second, the presence of domains 1 and 2 of hIFNAR1 and amino acid residue K249 in domain 2 was required for the binding of the most potent blocking mAb 2E1.

It was found that wild type and mutant soluble receptors effectively inhibited mAb binding to membrane hIFNAR1 in a specific manner. This result indicated that soluble hIFNAR1 retains the structure of the ECD of membrane hIFNAR1, at least in the antibody binding region.

Figure 6:
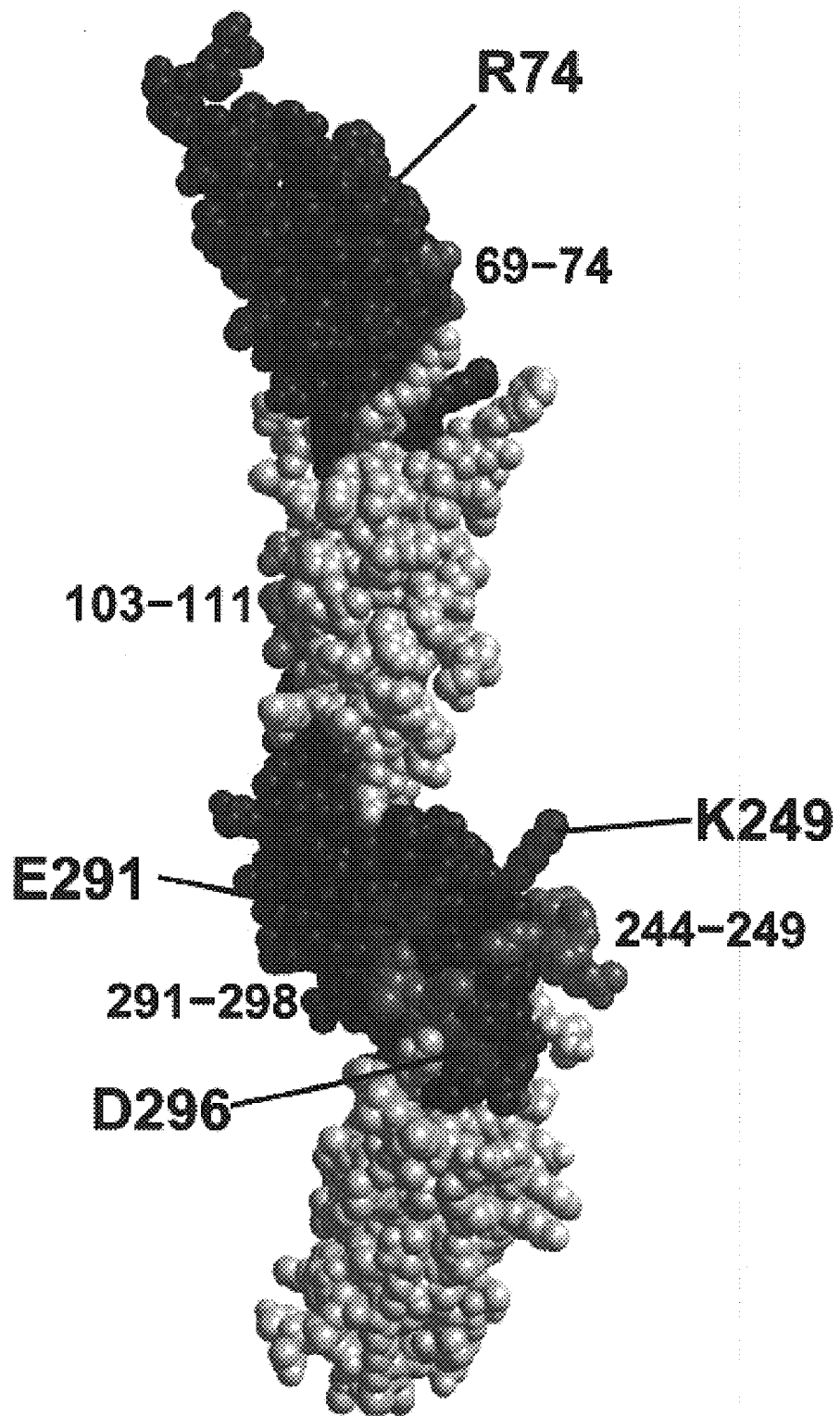
FIG. 6 is a model of hIFNAR1 displaying its protein sequence on the structural backbone of tissue factor. Subdomain SD100A of domain 1 and subdomain SD100A' of domain 2 are shown in dark gray. Subdomain SD100B of domain 1 and SD100B' of domain 2 are shown in light gray. Regions involved in the binding of anti-IFNAR1 mAbs are shown in orange. Amino acid residues involved in the binding of anti-IFNAR1 mAbs are shown in red.

The angle between the two subdomains is significantly different between members of class 1 and class 2 of the cytokine receptor family reported in Kossiakoff et al., *Protein Sci.* 3: 1697–1705 (1994). In class 1, the structures of the hGH receptor (reported in de Vos et al., *Science* 255: 306–312 (1992)) and the prolactin receptor (reported in Somers et al., *Nature* 372: 478–481 (1994)) display an angle of about 85°, whereas in class 2, the structures of tissue factor (reported in Muller et al., *J. Mol. Biol.* 256: 144–159 (1996)) and the IFN-γ receptor (reported in Walter et al., *Nature* 376: 230–235 (1995)) display an angle of about 120°. A model of the IFNAR1 structure was constructed by displaying the IFNAR1 sequence on the backbone of tissue factor; the orientation between domains 1 and 2 was modeled on that observed between subdomains. FIG. 6 shows a space-filling rendering of this model, with residues involved in the binding of mAbs depicted in red. Residues 69–74 and 103–111 are located in domain 1, in subdomains SD100A and SD100B, respectively, and residues 244–249 and 291–298 in SD100A' of domain 2. Residues 69–74 are situated far away from the other three, on top of the FIG. 6 model. Since substitutions in this region significantly affect binding of all mAbs except 5A8 (which was shown to bind both the domain 1 and domain 2 of hIFNAR1-IgG), it was determined that they cause a major structural change. The remaining three regions are clustered near each other in space and were determined to constitute part of the binding sites of the blocking mAbs 2E1 and 4A7.

mAbs 2E1 ($Kd^{-1}$=66 pM) and 2E8 ($Kd^{-1}$=97 pM) have been shown to exhibit similar high affinities to hIFNAR1-IgG and bind to the same epitope or overlapping epitopes according to the competitive binding ELISA results. However, mAb 2E1 is a potent blocking mAb while mAb 2E8 is a nonblocking mAb. The different blocking activity of these two mAbs is explained by the results of the mutant analysis as shown in Tables IV and V. The binding areas are indeed overlapping but different.

The following hybridomas have been deposited with the American Type Culture Collection, 12301 Parklawn Drive, Rockville, Md., USA (ATCC):

| Cell Lines | ATCC Accession No. | Deposit Date |
| --- | --- | --- |
| 5A8 | HB 12129 | Jun. 12, 1996 |
| 2E8 | HB 12130 | Jun. 12, 1996 |
| 2H6 | HB 12131 | Jun. 12, 1996 |
| 4A7 | HB 12132 | Jun. 12, 1996 |
| 2E1 | HB 12133 | Jun. 12, 1996 |

These deposits were made under the provisions of the Budapest Treaty on the International Recognition of the Deposit of Microorganisms for the Purpose of Patent Procedure and the Regulations thereunder (Budapest Treaty). This assures maintenance of a viable deposit for 30 years from the date of deposit. These cell lines will be made available by ATCC under the terms of the Budapest Treaty, and subject to an agreement between Genentech, Inc. and ATCC, which assures permanent and unrestricted availability of the cell lines to the public upon issuance of the pertinent U.S. patent or upon laying open to the public of any U.S. or foreign patent application, whichever comes first, and assures availability of the cell lines to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the deposited cell lines should be lost or destroyed when cultivated under suitable conditions, they will be promptly replaced on notification with a specimen of the same cell line. Availability of the deposited cell lines is not to be construed as a license to practice the invention in contravention of the rights granted under the authority of any government in accordance with its patent laws.

We claim:

1. An anti-IFNAR1 monoclonal antibody that inhibits the anti-viral activity of a first type I interferon selected from the group consisting of IFN-α1, IFN-α2/1, IFN-α2, IFN-α5, and IFN-α8 and does not inhibit the anti-viral activity of a second type I interferon selected from the group consisting of IFN-α1, IFN-α2/1, IFN-α5, and IFN-β.

2. The monoclonal antibody of claim 1 wherein the second type I interferon is IFN-β.

3. The monoclonal antibody of claim 2 wherein the first type I interferon is selected from the group consisting of IFN-α1 and IFN-α5.

4. The monoclonal antibody of claim 3 that inhibits the anti-viral activity of IFN-α1 and IFN-α5.

5. The monoclonal antibody of claim 4 that is designated 4A7, having ATCC Deposit No. HB12132.

6. The monoclonal antibody of claim 4, wherein the antibody recognizes a conformational epitope on IFNAR1.

7. The monoclonal antibody of claim 6, wherein the antibody does not bind to a peptide consisting of amino acids 1–200 of IFNAR1 having the sequence of SEQ ID NO:22 and does not bind to a peptide consisting of amino acids 204–404 of IFNAR1 having the sequence of SEQ ID NO:22.

8. The monoclonal antibody of claim 4 that binds to one or more amino acids in situ in the sequence of amino acids 244–249 of IFNAR1 having the sequence of SEQ ID NO:22 and binds to one or more amino acids in situ in the sequence of amino acids 291–298 of IFNAR1 having the sequence of SEQ ID NO:22.

9. The monoclonal antibody of claim 8 that binds to amino acids 249, 291 and 296 of IFNAR1 having the sequence of SEQ ID NO:22 in situ.

10. The monoclonal antibody of claim 9 that is designated 2E1, having ATCC Deposit No. HB 12133.

11. The monoclonal antibody of claim 1, wherein the second type I interferon is IFN-α1.

12. The monoclonal antibody of claim 1, wherein the second type I interferon is IFN-α2/1.

13. The monoclonal antibody of claim 1, wherein the second type I interferon is IFN-α5.

14. The monoclonal antibody of claim 3, wherein the first type I interferon is IFN-α1.

15. The monoclonal antibody of claim 3, wherein the first type I interferon is IFN-α5.

16. An anti-IFNAR1 monoclonal antibody that inhibits a type I interferon selected from the group consisting of IFN-α1, IFN-α2/1, IFN-α2, IFN-α5, and IFN-α8 from inducing formation of an IFN-stimulating response element binding protein but does not inhibit the anti-viral activity of a second type I interferon selected from the group consisting of IFN-α1, IFN-α2/1, IFN-α5, and IFN-β.

17. The monoclonal antibody of claim 1 wherein a said type I interferon is selected from the group consisting of IFN-α1, IFN-α2/1 and IFN-α5.

18. The monoclonal antibody of claim 16 therein said binding protein is the transcription factor ISGF3.

* * * * *

UNITED STATES PATENT AND TRADEMARK OFFICE
CERTIFICATE OF CORRECTION

| | | |
|---|---|---|
| PATENT NO. | : 6,713,609 B1 | Page 1 of 1 |
| APPLICATION NO. | : 09/056461 | |
| DATED | : March 30, 2004 | |
| INVENTOR(S) | : Chuntharapai et al. | |

It is certified that error appears in the above-identified patent and that said Letters Patent is hereby corrected as shown below:

Please delete item, [76] inventor, Richard B.Love

Column 3, line 50-51: "interferon-αcomprises" should read -- interferon-α comprises--

Column 6, line 46: "anti;bodies derived" should read --anitbodies derived--

Column 10, line 60: "and 3'ends of rearranged" should read --and 3' ends of rearranged--

Column 11, line 30: "with ail" should read --with all--

Column 22, line 10: "therapeutic,purposes" should read --therapuetic purposes--

Column 25, line 12 "anti-(FNAR1" should read --anti-IFNAR1--

Column 26, line 33: "I0 units/ml" should read --10 units/ml--

Column 49, line 52 "iymph node" should read --lymph node--

Column 76, line 57, claim 17: "wherein a said" should read --wherein said--

Column 76, line 61, claim 18: "therein said" should read --wherein said--

Signed and Sealed this

Twenty-second Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,713,609 B1  Page 1 of 1
APPLICATION NO. : 09/056461
DATED : March 30, 2004
INVENTOR(S) : Chuntharapai et al.

It is certified that error appears in the above-identified patent and that said Letters Patent is hereby corrected as shown below:

Column 3, line 50-51: "interferon-αcomprises" should read -- interferon-α comprises--

Column 6, line 46: "anti;bodies derived" should read --antibodies derived--

Column 10, line 60: "and 3'ends of rearranged" should read
--and 3' ends of rearranged--

Column 11, line 30: "with ail" should read --with all--

Column 22, line 10: "therapeutic,purposes" should read --therapeutic purposes--

Column 25, line 12: "anti-(FNARI" should read --anti-IFNAR1--

Column 26, line 33: "I0 units/ml" should read --10 units/ml--

Column 49, line 52: "iymph node" should read --lymph node--

Column 76, line 57, claim 17: "wherein a said" should read --wherein said--

Column 76, line 61, claim 18: "therein said" should read --wherein said--

Signed and Sealed this

Sixteenth Day of January, 2007

JON W. DUDAS
*Director of the United States Patent and Trademark Office*